US007741099B2

(12) United States Patent
Havenga et al.

(10) Patent No.: US 7,741,099 B2
(45) Date of Patent: Jun. 22, 2010

(54) ADENOVIRAL VECTORS AND USES THEREOF

(75) Inventors: Menzo Jans Emco Havenga, Alphen aan den Rijn (NL); Dan H. Barouch, Brookline, MA (US)

(73) Assignees: Beth Israel Deaconess Medical Center Inc., Brookline, MA (US); Crucell Holland B.V., Leiden (NL)

( * ) Notice: Subject to any disclaimer, the term of this patent is extended or adjusted under 35 U.S.C. 154(b) by 299 days.

(21) Appl. No.: 11/665,276

(22) PCT Filed: Oct. 12, 2005

(86) PCT No.: PCT/EP2005/055183

§ 371 (c)(1),
(2), (4) Date: Apr. 11, 2007

(87) PCT Pub. No.: WO2006/040330

PCT Pub. Date: Apr. 20, 2006

(65) Prior Publication Data

US 2008/0199939 A1 Aug. 21, 2008

Related U.S. Application Data

(60) Provisional application No. 60/697,724, filed on Jul. 8, 2005, provisional application No. 60/618,469, filed on Oct. 13, 2004.

(30) Foreign Application Priority Data

Oct. 13, 2004 (EP) .................................. 04105005

(51) Int. Cl.
*C12N 7/04* (2006.01)
*A61K 39/23* (2006.01)
(52) U.S. Cl. .................................... 435/236; 424/233.1
(58) Field of Classification Search ........................ None
See application file for complete search history.

(56) References Cited

FOREIGN PATENT DOCUMENTS

| WO | WO 98/32842 | 7/1998 |
|----|----|----|
| WO | WO 98/40509 | 9/1998 |
| WO | WO 00/03029 | 1/2000 |
| WO | WO 00/12738 | 3/2000 |
| WO | WO 00/70071 | 11/2000 |
| WO | WO 03/062400 A3 | 7/2003 |
| WO | WO 2004/037294 A2 | 5/2004 |

OTHER PUBLICATIONS

PCT International Preliminary Report on Patentability, PCT/EP2005/055183, dated Jan. 26, 2007.
U.S. Appl. No. 11/667,975, filed May 16, 2007, Havenga et al., Multivalent Vaccines Comprising recombinant Viral Vectors.
U.S. Appl. No. 11/786,409, filed Apr. 11, 2007, Vogels et al., Complementing Cell Lines.
U.S. Appl. No. 11/809,697, filed Jun. 1, 2007, Hateboer et al., Recombinant Protein Production in a Human Cell.
U.S. Appl. No. 11/899,572, filed Sep. 5, 2007, Vogels et al., Stable Adenoviral Vectors and Methods for Propagation Thereof.
U.S. Appl. No. 11/978,043, filed Oct. 25, 2007, Vogels et al., New Settings for Recombinant Adenoviral-Based Vaccines.
U.S. Appl. No. 11/980,222, filed Oct. 29, 2007, Bout et al., Serotypes of Adenovirus and Uses Thereof.
U.S. Appl. No. 12/225,259, filed Sep. 16, 2008, Barouch et al., Recombinant Adenoviruses Based on Seroytype 26 and 48, and Use Thereof.
U.S. Appl. No. 12/225,673, filed Sep. 26, 2008, Havenga et al., Compositions Comprising a Recombinant Adenovirus and an Adjuvant.
Barouch et al., Immunogenicity of Recombinant Adenovirus Serotype 35 Vaccine in the Presence of Pre-Existing Anti-Ad5 Immunity, Journal of Immunology, May 15, 2004, pp. 6290-6297, vol. 172, No. 10.
Crawford-Miksza et al., Analysis of 15 Adenovirus Hexon Proteins Reveals the Location and Structure of Seven Hypervariable Regions Containing Serotype-Specific Residues, Journal of Virology, Mar. 3, 1996, pp. 1836-1844, vol. 70, No. 3, The American Society of Microbiology, United States.
Gall et al., Construction and Characterization of Hexon-Chimeric Adenoviruses: Specification of Adenovirus Serotype, Journal of Virology, Dec. 1998, pp. 10260-10264, vol. 72, No. 12.
Ganesh et al., Adenovirus 35 Vectors with Fiber Chimeras Exhibit Altered Tropism In Vivo, Molecular Therapy, May 2003, pp. S53 vol. 7, No. 5, San Diego, USA.
Roberts et al., Hexon-chimaeric adenovirus serotype 5 vectors circumvent pre-existing anti-vector immunity, Nature, May 11, 2006, pp. 239-243, vol. 441, No. 7090.
Roy et al., Circumvention of Immunity to the Adenovirus Major Coat Protein Hexon, Journal of Virology, Aug. 1998, pp. 6875-6879, vol. 72, No. 8, The American Society for Microbiology, United States.
Rux et al., Type-Specific Epitope Locations Revealed by X-Ray Crystallographic Study of Adenovirus Type 5 Hexon, Molecular Therapy: The Journal of the American Society of Gene Therapy, Jan. 2000, pp. 18-30, vol. 1, No. 1.
Rux et al., Structural and Phylogenetic Analysis of Adenovirus Hexons by Use of High-Resolution X-Ray Crystallographic, Molecular, Modeling, and Sequence-Based Methods, Journal of Virology, Sep. 2003, pp. 9553-9566, vol. 77, No. 17.
Sakurai et al., Efficient Gene Transfer into Human CD34+ Cells by an Adenovirus Type 35 Vector, Gene Therapy, Jun. 2003, pp. 1041-1048, vol. 10, No. 12.
Seshidhar et al., Development of Adenovirus Serotype 35 as a Gene Transfer Vector, Virology, Jul. 5, 2003, pp. 384-393, vol. 311, No. 2, Academic Press, Orlando, US.

(Continued)

*Primary Examiner*—Bo Peng
(74) *Attorney, Agent, or Firm*—TraskBritt

(57) ABSTRACT

The present invention relates to recombinant adenoviral vectors based on adenoviruses that encounter pre-existing immunity in a minority of the human population and which harbor a chimeric capsid. The chimeric capsid comprises fiber proteins that have at least the knob domain of a human adenovirus that binds to the Coxsackievirus and Adenovirus Receptor (CAR) and a hexon protein from an adenovirus serotype that encounters pre-existing immunity in a low percentage of the human population.

12 Claims, 29 Drawing Sheets

OTHER PUBLICATIONS

Shayakhmetov et al., The Interaction between the Fiber Knob Domain and the Cellular Attachment Receptor Determines the Intracellular Trafficking Route of Adenoviruses, Journal of Virology, Mar. 2003, pp. 3712-3723, vol. 77, No. 6.

Sumida et al., Neutralizing Antibodies to Adenovirus Serotype 5 Vaccine Vectors Are Directed Primarily against the Adenovirus Hexon Protein, Journal of Immunology, Jun. 2005, pp. 7179-7185, vol. 174, No. 11.

Vigne et al., RCD Inclusion in the Hexon Monomer Provides Adenovirus Type 5-Based Vectors with a Fiber Knob-Independent Pathway for Infection, Journal of Virology, Jun. 1999, pp. 5156-5161, vol. 73, No. 6, The American Society for Microbiology, US.

Vogels et al, Replication-Deficient Human Adenovirus Type 35 Vectors for Gene Transfer and Vaccination: Efficient Human Cell Infection and Bypass of Preexisting Adenovirus Immunity, Journal of Virology, Aug. 2003, pp. 8263-8271, vol. 70, No. 15, The American Society for Microbiology, US.

Youil et al., Hexon Gene Switch Strategy for the Generation of Chimeric Recombinant Adenovirus, Human Gene Therapy, Jan. 20, 2002, pp. 311-320, vol. 13, No. 2.

International Preliminary Report on Patentability, PCT/EP2005/055183, dated Jan. 26, 2007.

International Search Report, PCT/EP2005/055183, dated Jul. 10, 2006.

U.S. Appl. No. 12/445,086, filed May 28, 2009, Vogels et al., Gene Delivery Vectors Provided With a Tissue Tropism for Smooth Muscle Cells, and/or Endothelial Cells.

U.S. Appl. No. 12/460,678, filed Jul. 23, 2009, Vogels et al., Serotype of Adenovirus and Uses Thereof.

U.S. Appl. No. 12/583,628, filed Aug. 24, 2009, Havenga et al., New Settings for Recombinant Adenoviral-Based Vaccines.

Fig. 2A.

```
ATGACCAAGAGAGTCCGGCTCAGTGACTCCTTCAACCCTGTCTACCCGTACGAAGAT
GAAAGCACCTCCCAACACCCCTTTATAAACCCAGGGTTTATTTCCCCAAATGGCTTC
ACACAAAGCCCAGACGGAGTTCTTACTTTAAAATGTTTAACCCCACTAACAACCACA
GGCGGATCTCTACAGCTAAAAGTGGGAGGGGACTTACAGTGGATGACACTGATGGT
ACCTTACAAGAAAACATACGTGCTACAGCACCCATTACTAAAAATAATCACTCTGTA
GAACTATCCATTGGAAATGGATTAGAAACTCAAAACAATAAACTATGTGCCAAATTG
GGAAATGGGTTAAAATTTAACAACGGTGACATTTGTATAAAGGATAGTATTAACACT
TTGTGGACCACACCAGCTCCATCTCCTAACTGTAGACTAAATGCAGAGAAAGATGCT
AAACTCACTTTGGTCTTAACAAAATGTGGCAGTCAAATACTTGCTACAGTTTCAGTT
TTGGCTGTTAAAGGCAGTTTGGCTCCAATATCTGGAACAGTTCAAAGTGCTCATCTT
ATTATAAGATTTGACGAAAATGGAGTGCTACTAAACAATTCCTTCCTGGACCCAGAA
TATTGGAACTTTAGAAATGGAGATCTTACTGAAGGCACAGCCTATACAAACGCTGTT
GGATTTATGCCTAACCTATCAGCTTATCCAAAATCTCACGGTAAAACTGCCAAAAGT
AACATTGTCAGTCAAGTTTACTTAAACGGAGACAAAACTAAACCTGTAACACTAACC
ATTACACTAAACGGTACACAGGAAACAGGAGACACAACTCCAAGTGCATACTCTATG
TCATTTTCATGGGACTGGTCTGGCCACAACTACATTAATGAAATATTTGCCACATCC
TCTTACACTTTTTCATACATTGCCCAAGAATAAGCTAGC
```

```
ATGACCAAGAGAGTCCGGCTCAGTGACTCCTTCAACCCTGTCTACCCgtacgACACG
GAAACCGGTCCTCCAACTGTGCCTTTTCTTACTCCTCCCTTTGTATCCCCCAATGGG
TTTCAAGAGAGTCCCCCTGGGGTACTCTCTTTGCGCCTATCCGAACCTCTAGTTACC
TCCAATGGCATGCTTGCGCTCAAAATGGGCAACGGCCTCTCTCTGGACGAGGCCGGC
AACCTTACCTCCCAAAATGTAACCACTGTGAGCCCACCTCTCAAAAAAACCAAGTCA
AACATAAACCTGGAAATATCTGCACCCCTCACAGTTACCTCAGAAGCCCTAACTGTG
GCTGCCGCCGCACCTCTAATGGTCGCGGGCAACACACTCACCATGCAATCACAGGCC
CCGCTAACCGTGCACGACTCCAAACTTAGCATTGCCACCCAAGGACCCCTCACAGTG
TCAGAAGGAAAGCTAGCCCTGCAAACATCAGGCCCCCTCACCACCACCGATAGCAGT
ACCCTTACTATCACTGCCTCACCCCCTCTAACTACTGCCACTGGTAGCTTGGGCATT
GACTTGAAAGAGCCCATTTATACACAAAATGGAAAACTAGGACTAAAGTACGGGGCT
CCTTTGCATGTAACAGACGACCTAAACACTTTGACCGTAGCAACTGGTCCAGGTGTG
ACTATTAATAATACTTCCTTGCAAACTAAAGTTACTGGAGCCTTGGGTTTTGATTCA
CAAGGCAATATGCAACTTAATGTAGCAGGAGGACTAAGGATTGATTCTCAAAACAGA
CGCCTTATACTTGATGTTAGTTATCCGTTTGATGCTCAAAACCAACTAAATCTAAGA
CTAGGACAGGGCCCTCTTTTTATAAACTCAGCCCACAACTTGGATATTAACTACAAC
AAAGGCCTTTACTTGTTTACAGCTTCAAACAATTCCAAAAAGCTTGAGGTTAACCTA
AGCACTGCCAAGGGGTTGATGTTTGACGCTACAGCCATAGCCATTAATGCAGGAGAT
GGGCTTGAATTTGGTTCACCTAATGCACCAAACACAAATCCCCTCAAAACAAAAATT
GGCCATGGCCTAGAATTTGATTCAAACAAGGCTATGGTTCCTAAACTAGGAACTGGC
CTTAGTTTTGACAGCACAGGTGCCATTACAGTAGGAAACAAAAATAATGATAAGCTA
ACTTTGTGGACCACACCAGCTCCATCTCCTAACTGTAGACTAAATGCAGAGAAAGAT
GCTAAACTCACTTTGGTCTTAACAAAATGTGGCAGTCAAATACTTGCTACAGTTTCA
GTTTTGGCTGTTAAAGGCAGTTTGGCTCCAATATCTGGAACAGTTCAAAGTGCTCAT
CTTATTATAAGATTTGACGAAAATGGAGTGCTACTAAACAATTCCTTCCTGGACCCA
GAATATTGGAACTTTAGAAATGGAGATCTTACTGAAGGCACAGCCTATACAAACGCT
GTTGGATTTATGCCTAACCTATCAGCTTATCCAAAATCTCACGGTAAAACTGCCAAA
AGTAACATTGTCAGTCAAGTTTACTTAAACGGAGACAAAACTAAACCTGTAACACTA
ACCATTACACTAAACGGTACACAGGAAACAGGAGACACAACTCCAAGTGCATACTCT
ATGTCATTTTCATGGGACTGGTCTGGCCACAACTACATTAATGAAATATTTGCCACA
TCCTCTTACACTTTTTCATACATTGCCCAAGAATAA
```

Fig. 2D

MTKRVRLSDSFNPVYPYDTETGPPTVPFLTPPFVSPNGFQESPPGVLSLRLSEPLVT

SNGMLALKMGNGLSLDEAGNLTSQNVTTVSPPLKKTKSNINLEISAPLTVTSEALTV

AAAAPLMVAGNTLTMQSQAPLTVHDSKLSIATQGPLTVSEGKLALQTSGPLTTTDSS

TLTITASPPLTTATGSLGIDLKEPIYTQNGKLGLKYGAPLHVTDDLNTLTVATGPGV

TINNTSLQTKVTGALGFDSQGNMQLNVAGGLRIDSQNRRLILDVSYPFDAQNQLNLR

LGQGPLFINSAHNLDINYNKGLYLFTASNNSKKLEVNLSTAKGLMFDATAIAINAGD

GLEFGSPNAPNTNPLKTKIGHGLEFDSNKAMVPKLGTGLSFDSTGAITVGNKNNDKL

TLWTTPAPSPNCRLNAEKDAKLTLVLTKCGSQILATVSVLAVKGSLAPISGTVQSAH

LIIRFDENGVLLNNSFLDPEYWNFRNGDLTEGTAYTNAVGFMPNLSAYPKSHGKTAK

SNIVSQVYLNGDKTKPVTLTITLNGTQETGDTTPSAYSMSFSWDWSGHNYINEIFAT

SSYTFSYIAQE

Fig. 2E

```
ATGACCAAGAGAGTCCGGCTCAGTGACTCCTTCAACCCTGTCTACCCGTACGAAGAT
GAAAGCACCTCCCAACACCCCTTTATAAACCCAGGGTTTATTTCCCCAAATGGCTTC
ACACAAAGCCCAGACGGAGTTCTTACTTTAAAATGTTTAACCCCACTAACAACCACA
GGCGGATCTCTACAGCTAAAAGTGGGAGGGGGACTTACAGTGGATGACACTGATGGT
ACCTTACAAGAAAACATACGTGCTACAGCACCCATTACTAAAAATAATCACTCTGTA
GAACTATCCATTGGAAATGGATTAGAAACTCAAAACAATAAACTATGTGCCAAATTG
GGAAATGGGTTAAAATTTAACAACGGTGACATTTGTATAAAGGATAGTATTAACACC
CTGTGGACAACCCCTGACACATCTCCAAATTGCAAATGAGTACAGAAAAGGATTCT
AAACTTACGTTGACACTTACAAAGTGTGGAAGTCAGGTTCTGGGAAATGTATCTTTA
CTTGCAGTTACAGGTGAATATCATCAAATGACTGCTACTACAAAGAAGGATGTAAAA
ATATCTTTACTATTTGATGAGAATGGAATTCTATTACCATCTTCGTCCCTTAGCAAA
GATTATTGGAATTACAGAAGTGATGATTCTATTGTATCTCAAAAATATAATAATGCA
GTTCCATTCATGCCAAACCTGACAGCTTATCCAAAACCAAGCGCTCAAAATGCAAAA
AACTATTCAAGAACTAAAATCATAAGTAATGTCTACTTAGGTGCTCTTACCTACCAA
CCTGTAATTATCACTATTGCATTTAATCAGGAAACTGAAAATGGATGTGCTTATTCT
ATAACATTTACCTTCACTTGGCAAAAAGACTATTCTGCCCAACAGTTTGATGTTACA
TCTTTTACCTTCTCATATCTTACCCAAGAGAACAAAGACAAAGACTAA
```

Fig. 2F

| M | T | K | R | V | R | L | S | D | S | F | N | P | V | Y | P | Y | E | D |
|---|---|---|---|---|---|---|---|---|---|---|---|---|---|---|---|---|---|---|
| E | S | T | S | Q | H | P | F | I | N | P | G | F | I | S | P | N | G | F |
| T | Q | S | P | D | G | V | L | T | L | K | C | L | T | P | L | T | T | T |
| G | G | S | L | Q | L | K | V | G | G | G | L | T | V | D | D | T | D | G |
| T | L | Q | E | N | I | R | A | T | P | I | T | K | N | N | H | S | V | |
| E | L | S | I | G | N | G | L | E | T | Q | N | N | K | L | C | A | K | L |
| G | N | G | L | K | F | N | N | G | D | I | C | I | K | D | S | I | N | T |
| L | W | T | T | P | D | T | S | P | N | C | K | M | S | T | E | K | D | S |
| K | L | T | L | T | L | T | K | C | G | S | Q | V | L | G | N | V | S | L |
| L | A | V | T | G | E | Y | H | Q | M | T | A | T | T | K | K | D | V | K |
| I | S | L | L | F | D | E | N | G | I | L | L | P | S | S | S | L | S | K |
| D | Y | W | N | Y | R | S | D | D | S | I | V | S | Q | K | Y | N | N | A |
| V | P | F | M | P | N | L | T | A | Y | P | K | P | S | A | Q | N | A | K |
| N | Y | S | R | T | K | I | I | S | N | V | Y | L | G | A | L | T | Y | Q |
| P | V | I | I | T | I | A | F | N | Q | E | T | E | N | G | C | A | Y | S |
| I | T | F | T | F | T | W | Q | K | D | Y | S | A | Q | Q | F | D | V | T |
| S | F | T | F | S | Y | L | T | Q | E | N | K | D | K | D | | | | |

Fig. 2G

```
ATGACCAAGAGAGTCCGGCTCAGTGACTCCTTCAACCCTGTCTACCCGTACGAAGAT
GAAAGCACCTCCCAACACCCCTTTATAAACCCAGGGTTTATTTCCCCAAATGGCTTC
ACACAAAGCCCAGACGGAGTTCTTACTTTAAAATGTTTAACCCCACTAACAACCACA
GGCGGATCTCTACAGCTAAAAGTGGGAGGGGGACTTACAGTGGATGACACTGATGGT
ACCTTACAAGAAAACATACGTGCTACAGCACCCATTACTAAAAATAATCACTCTGTA
GAACTATCCATTGGAAATGGATTAGAAACTCAAAACAATAAACTATGTGCCAAATTG
GGAAATGGGTTAAAATTTAACAACGGTGACATTTGTATAAAGGATAGTATTAACACC
CTTTGGACAACTCCAGACCCATCTCCAAACTGCAAAGTTTCAGAAGAGAAGGATTCC
AAGCTTACTCTAGTTTTAACAAAGTGCGGAAGTCAGATTCTGGCCAGTGTATCATTG
CTTGTTGTTAAAGGGAAGTTTGCCAATATTAACAATAAAACAAACCCAGGCGAGGAC
TATAAAAAATTTTCAGTTAAATTATTGTTTGATGCCAATGGTAAATTATTGACAGGA
TCAAGCCTAGATGGAAATTATTGGAATTATAAAAACAAGGATAGTGTGATTGGGTCT
CCTTATGAAAATGCCGTTCCTTTTATGCCTAATTCCACAGCTTATCCTAAAATCATC
AATAATGGAACAGCTAATCCTGAAGATAAAAAAGTGCAGCCAAAAAAACTATTGTC
ACTAATGTGTACCTAGGGGAGATGCAGCTAAACCCGTGGCTACCACTATTAGTTTC
AACAAAGAAACTGAATCTAATTGTGTTTATTCTATAACCTTTGACTTTGCTTGGAAC
AAAACTTACAAAAATGTTCCATTTGATTCATCTTCGCTAACATTTTCATATATTGCC
CAAGATGCCGAAGACAAAAACGAATAA
```

Fig. 7A          Ad5
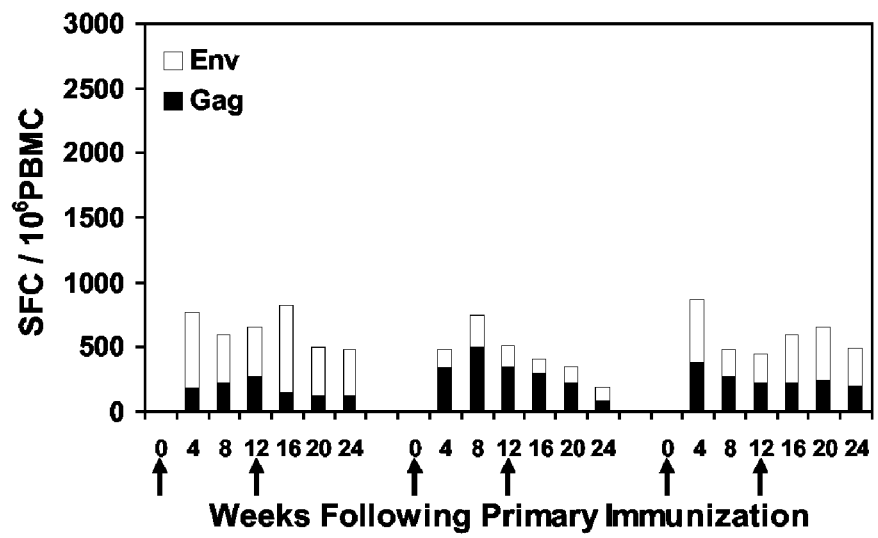
Fig. 7B          Ad5
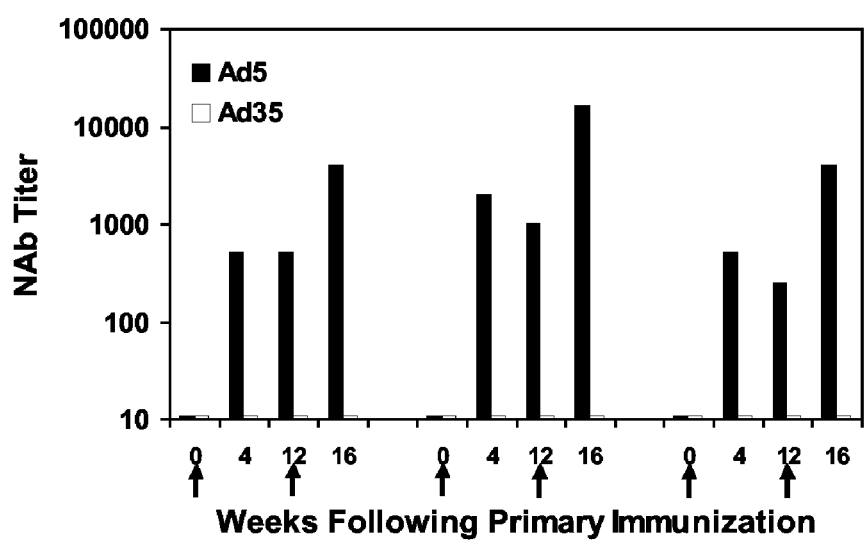

Fig. 7C  Ad35
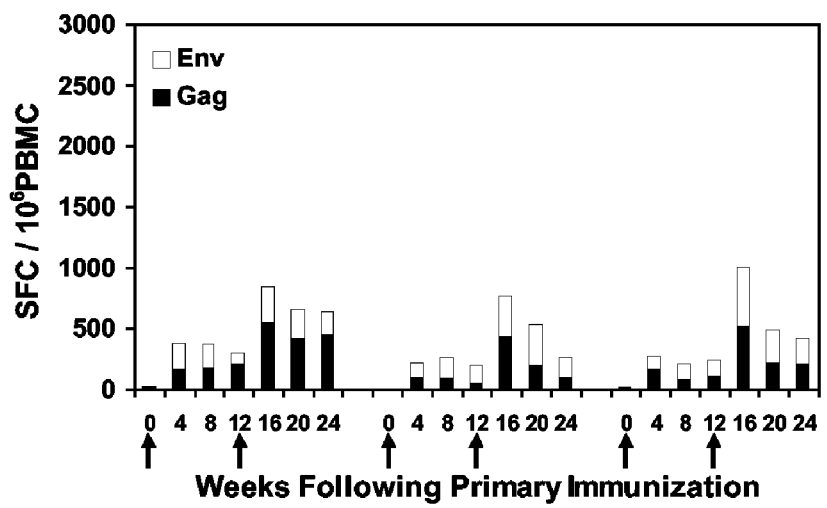
Fig. 7D  Ad35
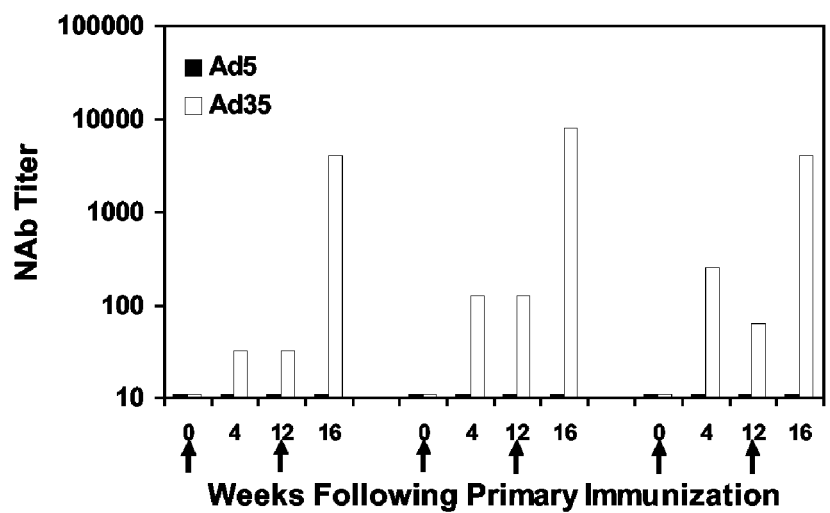

Fig. 7E    Ad35k5
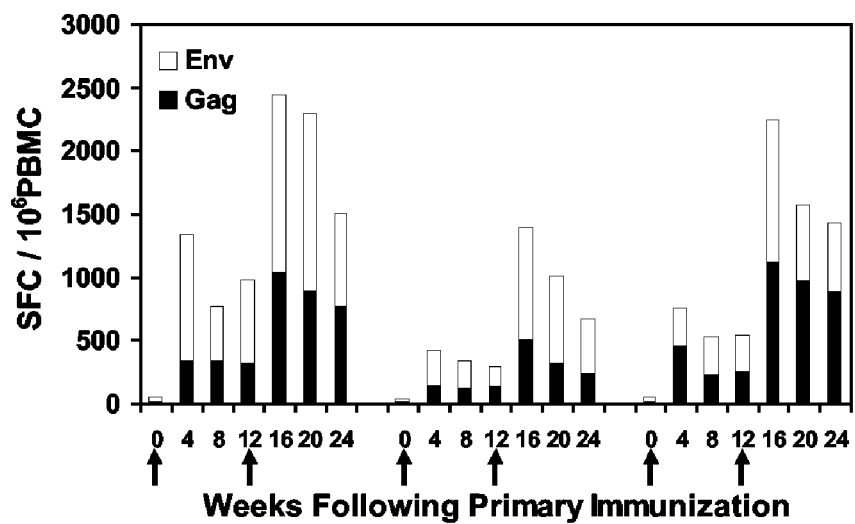
Fig. 7F    Ad35k5
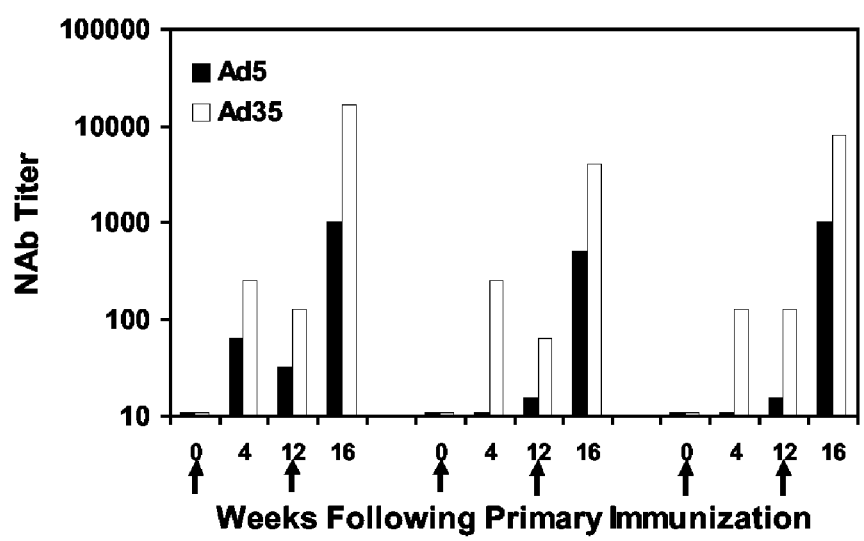

Fig. 11

Ad5HVR48(1-7) Hexon Protein Sequence (SEQ ID NO:12)

Ad5HVR35(1-7) Hexon Protein Sequence (SEQ ID NO:13)

Ad5HVR11(1-7) Hexon Protein Sequence (SEQ ID NO:14)

Ad5HVR26(1-7) Hexon Protein Sequence (SEQ ID NO:15)

Ad5HVRPan9(1-7) Hexon Protein Sequence (SEQ ID NO:16)

Ad5HVR48(1-7)* Hexon Protein Sequence (SEQ ID NO:84)
HVR1* is deleted (indicated by brackets), HVR2* is
replaced with a QG spacer, HVR3* - HVR7* are replaced
according to the sequences provided in Table IV.

Ad5HVR35(1-7)* Hexon Protein Sequence (SEQ ID NO:85)
HVR1* is deleted (indicated by brackets), HVR2* is
replaced with a QG spacer, HVR3* - HVR7* are replaced
according to the sequences provided in Table IV.

Ad5HVR26(1-7)* Hexon Protein Sequence (SEQ ID NO:86)
HVR1* is deleted (indicated by brackets), HVR2* is
replaced with a QG spacer, HVR3* - HVR7* are replaced
according to the sequences provided in Table IV.

Ad5HVR49(1-7)* Hexon Protein Sequence (SEQ ID NO:87)
HVR1* is deleted (indicated by brackets), HVR2* is
replaced with a QG spacer, HVR3* - HVR7* are replaced
according to the sequences provided in Table IV.

```
M A T P S M M P Q W S Y M H I S G Q D A S E Y
L S P G L V Q F A R A T E T Y F S L N N K F R
N P T V A P T H D V T T D R S Q R L T L R F I
P V D R E D T A Y S Y K A R F T L A V G D N R
V L D M A S T Y F D I R G V L D R G P T F K P
Y S G T A Y N A L A P K G A P N P C E W D()T H
V F G Q A P Y S G I N I T K E G I Q I G Q G K
Y A D K T F Q P E P Q I G E S Q W Y N T E I N
H A A G R V L K K T T P M K P C Y G S Y A K P
T N E N G G Q G I L V K T G E N G K P T E E S
Q V E M Q F F S L R Q N D T G G N N N Q P K V
V L Y S E D V D I E T P D T H I S Y M P T T S
D G N S R E L M G Q Q S M P N R P N Y I A F R
D N F I G L M Y Y N S T G N M G V L A G Q A S
Q L N A V V D L Q D R N T E L S Y Q L L L D S
I G D R T R Y F S M W N Q A V D S Y D P D V R
I I E N H G T E D E L P N Y C F P L G G V I N
T E T L T K V K P D T T V A G T N D K W K V N
A K F S D K N E I R V G N N F A M E I N L N A
N L W R N F L Y S N I A L Y L P D K L K Y S P
S N V K I S D N P N T Y D Y M N K R V V A P G
L V D C Y I N L G A R W S L D Y M D N V N P F
N H H R N A G L R Y R S M L L G N G R Y V P F
H I Q V P Q K F F A I K N L L L P G S Y T Y
E W N F R K D V N M V L Q S S L G N D L R V D
G A S I K F D S I C L Y A T F F P M A H N T A
S T L E A M L R N D T N D Q S F N D Y L S A A
N M L Y P I P A N A T N V P I S I P S R N W A
A F R G W A F T R L K T K E T P S L G S G Y D
P Y Y T Y S G S I P Y L D G T F Y L N H T F K
K V A I T F D S S V S W P G N D R L L T P N E
F E I K R S V D G E G Y N V A Q C N M T K D W
F L V Q M L A N Y N I G Y Q G F Y I P E S Y K
D R M Y S F F R N F Q P M S R Q V V D D T K Y
K D Y Q Q V G I L H Q H N N S G F V G Y L A P
T M R E G Q A Y P A N F P Y P L I G K T A V D
S I T Q K K F L C D R T L W R I P F S S N F M
S M G A L T D L G Q N L L Y A N S A H A L D M
T F E V D P M D E P T L L Y V L F E V F D V V
R V H R P H R G V I E T V Y L R T P F S A G N
A T T
```

ADENOVIRAL VECTORS AND USES THEREOF

CROSS-REFERENCE TO RELATED APPLICATIONS

This application is the national phase of PCT/EP2005/055183, filed Oct. 12, 2005 designating the United States, and published, in English, on Apr. 20, 2006, as WO 2006/040330 A2, and claims the benefit, under 35 U.S.C. §119(e), of U.S. provisional patent application 60/618,469, filed Oct. 13, 2004, and U.S. provisional patent application 60/697,724 filed Jul. 8, 2005, and further claims priority to EP 04105005.5 filed Oct. 13, 2004.

FIELD OF THE INVENTION

The invention relates to the field of medicine, more in particular to the field of therapeutic and prophylactic treatment, by using recombinant chimeric adenoviral vectors comprising a therapeutic nucleic acid in vaccine compositions.

BACKGROUND OF THE INVENTION

Recombinant adenoviral vectors are widely applied for gene therapy applications and vaccines. To date, 51 different adenovirus serotypes have been identified. The subgroup C adenoviruses have been most extensively studied for applications such as gene therapy; especially serotype 2 and 5 (Ad2 and Ad5) are widely used in the art. Recombinant Ad5 is used in a variety of different purposes, including vaccination. Importantly, Ad5 vector-based vaccines have been shown to elicit potent and protective immune responses in a variety of animal models. Moreover, large-scale clinical trials for HIV vaccination are ongoing in which Ad5-based recombinant vectors are being used (WO 01/02607; WO 02/22080; Shiver et al. 2002; Letvin et al. 2002; Shiver and Emini. 2004). However, the utility of recombinant Ad5 vector-based vaccines for HIV and other pathogens will likely be significantly limited by the high seroprevalence of Ad5-specific neutralizing antibodies (NAbs) in human populations. The existence of anti-Ad5 immunity has been shown to suppress substantially the immunogenicity of Ad5-based vaccines in studies in mice and rhesus monkeys. Early data from phase-1 clinical trials show that this problem may also occur in humans (Shiver 2004).

One promising strategy to circumvent the existence of pre-existing immunity in individuals previously infected with the most common human adenoviruses (such as Ad5), involves the development of recombinant vectors from adenovirus serotypes that do not encounter such pre-existing immunities. Human adenoviral vectors that were identified to be particularly useful are based on serotypes 11, 26, 34, 35, 48, 49, and 50 as was shown in WO 00/70071, WO 02/40665 and WO 2004/037294 (see also Vogels et al. 2003). Others have found that also adenovirus 24 (Ad24) is of particular interest as it is shown to be a rare serotype (WO 2004/083418).

A similar strategy is based on the use of simian adenoviruses since these do typically not infect humans. They exhibit a low seroprevalence in human samples. They are however applicable for human use since it was shown that these viruses could infect human cells in vitro (WO 03/000283; WO 2004/037189).

It was shown that adenovirus serotype 35 (Ad35) vector-based vaccines could elicit potent cellular immune responses that were not significantly suppressed by anti-Ad5 immunity (Barouch et al. 2004; Vogels et al. 2003). Similarly, chimpanzee adenoviruses have been shown to elicit immune responses that were minimally affected by anti-Ad5 immunity (Farina et al. 2001; Pinto et al. 2003). It was recently demonstrated that neutralizing antibodies (NAbs) and CD8+ T lymphocyte responses both contribute to anti-Ad5 immunity, whereas Ad5-specific NAbs appear to play the primary role (Sumida et al. 2004). Although this development appears to be a very useful approach, it was also demonstrated in mice that Ad35 vector-based vaccines proved less immunogenic than Ad5 vector-based vaccines in studies in which there was no pre-existing Ad5-immunity (Barouch et al. 2004).

Clearly, there is a need in the field for alternative adenoviral vectors that do not encounter pre-existing immunities in the host, but that are still immunogenic and capable of inducing strong immune responses against the proteins encoded by the heterologous nucleic acids inserted in the nucleic acid carried by the vector.

BRIEF DESCRIPTION OF THE DRAWINGS

FIG. 2(A) shows the nucleic acid sequence encoding the Ad35k5 fiber protein (SEQ ID NO:1; the part encoding the Ad5 fiber knob is underlined); (B) shows the amino acid sequence of the Ad35k5 fiber protein (SEQ ID NO:2; the part representing the Ad5 fiber knob is underlined); (C) shows the nucleic acid sequence encoding the Ad35f5 fiber protein (SEQ ID NO:4; the part encoding the remaining Ad35 fiber fragment is underlined, while the BsiWI cloning site is represented in small caps); (D) shows the amino acid sequence of the Ad35f5 fiber protein (SEQ ID NO:5; the part representing the remaining Ad35 fiber fragment is underlined); (E) shows the nucleic acid sequence encoding the Ad35k26 fiber protein (SEQ ID NO:80; the part encoding the Ad26 fiber knob is underlined); (F) shows the amino acid sequence of the Ad35k26 fiber protein (SEQ ID NO:81; the part representing the Ad26 fiber knob is underlined); (G) shows the nucleic acid sequence encoding the Ad35k49 fiber protein (SEQ ID NO:82; the part encoding the Ad49 fiber knob is underlined); (H) shows the amino acid sequence of the Ad35k49 fiber protein (SEQ ID NO:83; the part representing the Ad49 fiber knob is underlined).

FIG. 7 shows the immunogenicity of Ad5, Ad35k5, and Ad35 vectors in rhesus monkeys primed at week 0 with $10^{11}$ vp Ad5-Gag (A,B), Ad35-Gag (C,D), and Ad35k5-Gag (E,F). At week 12, all monkeys received a homologous boost immunization. Env- and Gag-specific cellular immune responses were assessed by pooled peptide IFN-γ ELISPOT assays at multiple time points following immunization (A,C,E). Vector-specific NAb titers were assessed by Ad5 and Ad35 virus neutralization assays (B,D,F).

FIG. 11 shows the amino acid sequence (SEQ ID NO:12) of the Ad5-based hexon protein, with the incorporation of the seven HVR's for the seven corresponding HVR's (underlined) from Ad48 (Ad5HVR48 (1-7)).

FIG. 12 shows the amino acid sequence (SEQ ID NO:13) of the Ad5-based hexon protein, with the incorporation of the seven HVR's for the seven corresponding HVR's (underlined) from Ad35 (Ad5HVR35(1-7)).

FIG. 13 shows the amino acid sequence (SEQ ID NO:14) of the Ad5-based hexon protein, with the incorporation of the seven HVR's for the seven corresponding HVR's (underlined) from Ad11 (Ad5HVR11(1-7)).

FIG. 14 shows the amino acid sequence (SEQ ID NO:15) of the Ad5-based hexon protein, with the incorporation of the seven HVR's for the seven corresponding HVR's (underlined) from Ad26 (Ad5HVR26(1-7)).

FIG. 15 shows the amino acid sequence (SEQ ID NO:16) of the Ad5-based hexon protein, with the incorporation of the seven HVR's for the seven corresponding HVR's (underlined) from Pan9 adenovirus (Ad5HVRPan9 (1-7)).

FIG. 17 shows the amino acid sequence of the hexon protein in Ad5HVR48(1-7)* (SEQ ID NO:84) in which the HVR1 sequence as defined in Table IV is deleted, the HVR2 sequence according to Table IV is replaced with a QG linker and HVR3-HVR7 according to the definition of Table IV have been replaced between Ad5 and Ad48.

FIG. 18; as FIG. 17, now for Ad5HVR35(1-7)* (SEQ ID NO:85).

FIG. 19; as FIG. 17, now for Ad5HVR26(1-7)* (SEQ ID NO:86).

FIG. 20; as FIG. 17, now for Ad5HVR49(1-7)* (SEQ ID NO:87).

SUMMARY OF THE INVENTION

Figure 1A:
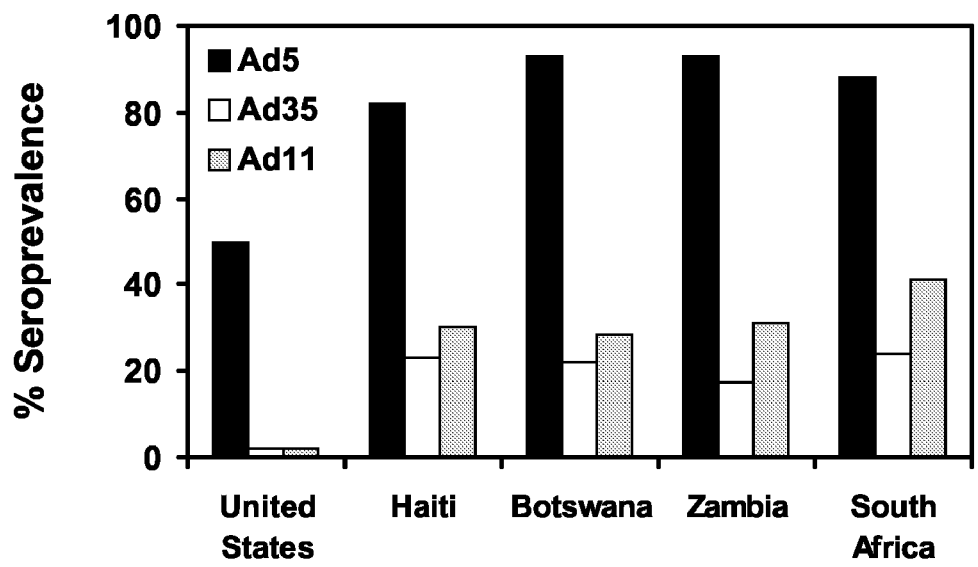
FIG. 1(A) shows the percentage of seroprevalence of Ad5, Ad11 and Ad35 in samples from the United States, Haiti, Botswana, Zambia and South Africa; (B) shows the neutralizing antibody titer against Ad5, Ad11 and Ad35 in the samples from the US and those from Africa.

Newly developed recombinant adenoviral vectors for improved gene delivery, vaccination, and gene therapy are disclosed herein. In one preferred embodiment the vector is a recombinant adenovirus based on adenovirus serotype 35 (Ad35) wherein at least the Ad35 fiber knob has been replaced by the fiber knob of a serotype that binds to the Coxsackievirus and Adenovirus Receptor (CAR). More preferably, this serotype is an Ad5 fiber knob (resulting in a vector termed Ad35k5, wherein only the knob has been replaced, or in a vector termed Ad35f5, wherein the knob, shaft and part of the tail have been replaced). The shaft and tail of the fiber may be of the carrying backbone serotype, i.e. Ad35, whereas the invention also relates to vectors in which the shaft domain is of the same serotype as fiber knob serotype. In Ad35f5 the part of the tail region left from the backbone serotype ensures a proper interaction with the remaining part of the capsid for the production of stable vectors. The vectors of the present invention comprise a therapeutic nucleic acid of interest, preferably a nucleic acid that is applicable for vaccination purposes.

The invention relates to recombinant adenoviral vectors that encounter low pre-existing immunity in most of the human population, while still being able to induce a strong immune response against the antigen encoded by a nucleic acid comprised by the vector. This is achieved by producing recombinant vectors based on adenovirus serotypes, such as Ad11, Ad24, Ad26, Ad34, Ad35, Ad48, Ad49, Ad50, or simian adenoviruses, carrying a chimeric capsid. The chimeric capsid comprises fiber proteins that are partly based on fiber proteins from human adenovirus serotypes different from the backbone vector, and that in a most preferred embodiment bind (through their knob domain) to the CAR receptor. Many different adenoviruses that preferentially bind CAR can be used for providing the fiber knob, such as human adenoviruses from subgroup A, C, D, E, and F, and ovine adenoviruses that also bind CAR. Preferred adenovirus serotypes that are used for their fiber knob domains are the human adenoviruses from subgroup C, more preferably Ad2 and Ad5.

In another embodiment the virus produced according to the invention is a recombinant adenovirus based on a subgroup C adenovirus, preferably Ad5, which is made replication-defective by a functional deletion of the E1 region and wherein the hexon protein in the viral capsid is a chimeric protein such that one or more of the hyper variable regions (HVR's) have been replaced by the HVR's derived from a rare adenovirus serotype. Such rare serotypes do not encounter NAbs in most of the individuals in the human population. Preferred serotypes that are used to provide the HVR's are Ad35 and Ad48. Preferably, the recombinant virus comprises a heterologous nucleic acid of interest that is to be delivered to the host for prophylactic or therapeutic purposes.

DETAILED DESCRIPTION

As discussed above, Ad5-based recombinant vectors are hampered in their use by the existence of neutralizing antibodies (NAbs) that are present in most of the human individuals due to a prior infection with wild type virus. Although the different capsid proteins present in the viral coat induce antibodies in the host, it has been demonstrated that the primary target of Ad5-specific NAbs is the Ad5 hexon protein (Sumida et al. 2005). This led to the idea that, by changing the hexon protein such that it could no longer be seen by the pre-existing NAbs, improved adenoviral vectors could be produced that would be beneficial in humans that either already have NAbs against Ad5, or that were previously immunized with previous vaccines based on Ad5, or that were primed with Ad5 based vectors in a prime/boost vaccination regime. However, altering the hexon protein turned out not to be an easy task. Complete hexon changes have generally only been possible between adenoviruses within the same Ad subgroup and resulted in poorly viable virus (Youil et al. 2002; Gall et al. 1998; Roy et al. 1998). If this would be the limitation then a vector based on Ad5 had to contain a hexon protein from another subgroup C adenoviruses. However, most of these, if not all, are useless in the sense that those serotypes are not considered rare. Most individuals in the human population have once encountered the serotypes from subgroup C. It would be preferred to use a hexon from a serotype that should not encounter NAbs already present. Those rare serotypes are predominantly found in subgroup B (Ad11, Ad34, Ad35, Ad50) and D (Ad24, Ad26, Ad48 and Ad49).

The inventors of the present invention have now for the first time shown that by (re-)defining specific parts of the hexon and by using a conservative approach and available structure and sequence data, certain regions could be identified and could be swapped resulting in producible recombinant viruses that are viable and could be produced to high enough titres. The preferred serotypes that are used to provide their hexon protein, or the relevant parts thereof, are Ad11, Ad24, Ad26, Ad34, Ad35, Ad48, Ad49 and Ad50, as these serotypes are known to encounter low pre-existing immunity (see WO 00/70071). More preferred are Ad11, Ad26, Ad35 and Ad48, whereas Ad48 is the most preferred serotype. Also non-human adenoviruses are interesting in this respect. One preferred example is the chimpanzee adenovirus Pan9.

The regions that were identified are the 7 surface loops also known as the hexon Hypervariable Regions (HVR's). The hexon variability among adenovirus serotypes is concentrated in these 7 loops (Crawford-Miksza and Schnurr. 1996). It is to be understood that the invention is not limited to the use of the HVR's of Ad48 as outlined in the examples. This is further substantiated by the identification of HVR's in Ad5, Ad11, Ad26, Ad34, Ad35, Ad48, Ad49 and Ad50 in a somewhat broad definition (see Table II) and in a somewhat more limited, a more minimalistic definition (see Table IV). Ad48 serves as an example for all other serotypes that also encounter low-pre-existing immunity and that are also useful in making chimeric adenovirus that benefit from the known advantages of the subgroup C adenovirus, exemplified by Ad5 (strong immunogenicity, easy to produce, etc.) with the benefits of the rare serotypes (low pre-existing immunity). Clearly, if one would contemplate the use of a prime/boost vaccination regimen in which it is preferred to use another serotype backbone, such as Ad35, then it would be beneficial to boost with a vector that does not encounter the raised NAbs against the priming vector. Thus, combinations such as Ad11, Ad24, Ad26, Ad35, Ad48 Ad49, Ad50, etc. with the HVR's of another rare serotype (such as any of the rare serotypes mentioned above) are also part of the present invention. Non-limiting examples of such vectors are Ad5HVR48, Ad5HVR35, Ad35HVR11, Ad35HVR48, Ad11HVR35, and Ad11HVR48, having at least one, more preferably six, and most preferably seven HVR's exchanged between serotypes. So, preferably at least one HVR from a rare serotype is taken and inserted into the hexon of the backbone serotype. It has been shown by the inventors of the present invention that replacing all seven HVR's from Ad5 by the corresponding HVR's from Ad48 resulted in a viable and producible vector that encountered hardly any pre-existing immunity in mice immunized with empty Ad5 viruses. However, if only the first HVR (seen from the left ITR to the right ITR in the viral genome) was replaced no effect was seen. This does not mean that one replacement could not be enough. It is thought that one region is more immunogenic than others, and it remains to be investigated which of the 7 identified regions contributes most and which of the HVR's do not have to be replaced in a certain setting or for a specific application. It may be that certain individuals raise different immune responses towards different HVR's in comparison to other individuals. Moreover, chimeric hexon containing vectors may prove beneficial in settings where there is only a moderate NAb activity in the host. The pre-existing immunity raised according to the provided examples is very high, due to 2 consecutive doses of $10^{10}$ vp of the empty Ad5 vector. Nevertheless, it is most preferred that all HVR's within the hexon protein are replaced as this would provide the best chance of yielding a vector not detected by the pre-existing NAbs present in the host.

To develop improved adenoviral vectors, first the Ad5-specific neutralizing antibody (NAb) epitopes were mapped. It was revealed that Ad5 seroprevalence and titers were very high in human populations (approximately 50% in the United States and 90% in parts of the developing world). Moreover, as disclosed herein, functionally significant Ad5-specific NAbs were found to be directed almost exclusively against the hexon protein (see also Sumida et al. 2005). In contrast, Ad5-specific antibodies directed against the fiber protein do not significantly suppress Ad5 vaccine immunogenicity under relevant natural existing circumstances, i.e. which circumstances relate to anti-Ad5 NAbs titers found in humans. In contrast to Ad5, Ad35 and Ad11 seroprevalence and titers are found to be very low in human populations in many different parts of the world.

The present invention relates to novel adenoviral vectors that carry the hexon of a rare (or at least rarely neutralized) Ad serotype such as Ad11, Ad24, Ad26, Ad34, Ad35, Ad48, Ad49 and Ad50 and preferably at least the fiber knob domain from a serotype that interacts with the CAR receptor, such as most human adenovirus serotypes from subgroup A, C, D, E, and F and the ovine adenoviruses. Preferred serotypes that are used as a backbone vector and thus carry their own hexon protein towards which rarely NAbs are found in the human population are Ad11 and Ad35. A preferred serotype that is used as a backbone vector and for its fiber is Ad5. It is well recognized in the art that cells that play a major role in immune responses are dendritic cells, since these are cells that are able to efficiently present immunogenic peptides on their surface thereby eliciting a strong immune response against such a peptide. Vectors that have been preferred in the art are because of their ability to infect dendritic cells very efficiently are those from adenovirus subgroup B, or vectors that carry fiber proteins from adenoviruses that recognize and infect dendritic cells in an efficient manner, see for example WO 02/24730 and WO 00/70071. These vectors presumably use CD46 as receptor. Surprisingly, as shown herein, it was now found by the inventors of the present invention that a vector carrying at least a fiber knob of an adenoviral vector known to interact through CAR, namely Ad5, when cloned on top of a vector that encounters low levels of pre-existing immunity, behaves such that immune responses are improved. This is highly unexpected taking the desired immune response route via dendritic cells into account.

It should be understood that the knob domain, which domain can easily be distinguished from the rest of the fiber protein by those of general skill in the art (through sequence comparisons and general knowledge about receptor interactions) is the domain that is predominantly involved in the recognition of specific cellular receptors to which the adenoviral vector binds. It was previously shown that the Ad5 fiber knob interacts with CAR on the surface of cells and mediates efficient viral attachment prior to viral entry that is further facilitated by the penton base and cellular integrins (Bergelson et al. 1997; Bewley et al. 1999; Roelvink et al. 1998 and 1999; Wickham et al. 1993), while the B group viruses, such as Ad11 and Ad35 interact through CD46 (Gagger et al. 2003). The present invention relates to adenoviral vectors in which at least the receptor-binding domain (defined by the knob domain) is swapped. The latter vectors thus still may comprise fiber domains such as parts of the shaft and/or the tail from the backbone vector. It is actually desired to use at least a part of the tail region of the backbone vector to ensure a proper stable interaction with other capsid proteins, resulting in stable recombinant vectors.

The chimeric adenoviral vectors of the present invention are more efficient for vaccines and gene therapy than vectors solely based on Ad5 or Ad35 without chimeric fibers. Chimeric adenoviruses carrying chimeric Ad5-Ad35 fibers are known in the art. Ad5 vectors carrying chimeric fibers in which at least the knob domain was derived from Ad35, were disclosed (WO 00/31285, WO 00/52186; WO 02/24730; Shayakhmetov et al. 2003; Rea et al. 2001). Smith et al. (2003) disclosed a chimeric fiber in which the tail and shaft are from Ad35, while the knob domain is from Ad5. All the vectors from these cited references are based on Ad5, implying the fact that the vectors would still encounter pre-existing immunity due to the presence of the Ad5 hexon in the viral vector capsid. The data provided by Ophorst et al. (2004) confirmed this phenomenon. Recombinant replication-defective Ad35 vectors and methods for producing them are also known in the art (WO 00/70071; WO 02/40665), whereas Ganesh et al. (2003) disclosed the use of an Ad35-based vector which comprises a fiber in which the fiber knob of Ad35 has been replaced by that of Ad5. However, the vector carried a marker gene (Green Fluorescence Protein, GFP) and apparently exhibited low transduction efficiencies. Consequently, Ganesh et al. do not disclose or suggest vaccines based on vectors wherein at least the knob of Ad35 was replaced by the knob of Ad5, let alone advantages associated with their use. Ganesh et al. disclose also a vector based on Ad35 with a complete Ad5 fiber. It must be noted that this vector comprises a full Ad5 fiber and not a chimeric fiber and thus differs from the vectors disclosed herein. Ganesh et al. warn that low transduction efficiencies were found with the partial fiber swap. The vectors according to the invention have good transduction efficiencies, while the chimeric fibers ensure a stable anchoring in the remaining capsid. The person skilled in the art would not have an incentive for vaccination purposes to replace the fiber knob of serotypes that are known to infect dendritic cells very efficiently (such as those of subgroup B, for instance Ad11, Ad34 and Ad35) by a fiber knob from a serotype that infects cells primarily through CAR.

Because the neutralizing activity from the host towards the adenoviral vectors is primarily due to NAbs against the hexon protein, adenoviral vectors may also be based on highly neutralized serotypes, exemplified by Ad5, wherein the hexon is swapped against the hexon of a rarely neutralized serotype, such as Ad11, Ad24, Ad26, Ad34, Ad35, Ad48, Ad49 and Ad50. An example of such a vector is referred to as Ad5h35 (Ad5-based vector comprising the hexon protein from Ad35 in place of the Ad5 hexon). A person skilled in the art is able to envision and to make the different possible combinations based on the information disclosed herein and based on knowledge available in the art. It became clear that exchanging entire hexons proved difficult (Gall et al. 1998; Youil et al. 2002). One new and useful way of constructing chimeric hexon protein is disclosed in the examples. Another way of cloning vectors comprising chimeric capsid using hexon proteins from other serotypes has been disclosed in example 8 of WO 00/03029.

The recombinant adenoviral vectors of the present invention, namely those based on serotypes that encounter generally low pre-existing activities in the human population (Ad11, Ad24, Ad26, Ad34, Ad35, Ad48, Ad49 and Ad50, as well as certain simian adenoviruses) carrying the knob domain of an adenovirus that generally elicit a high immune response, represent an improvement over both the adenovirus that generally elicits a high immune response as well as over the adenovirus that evades pre-existing neutralizing activity because it carries a hexon protein that is not detected by the pre-existing immunity in a high percentage of the world population. In other words and as exemplified herein, Ad35fib5 and Ad35k5 both represent improvements over both the Ad5 and the Ad35 vector.

Given the high levels of anti-Ad5 immunity in human populations, Ad5 vectors are likely to be substantially suppressed by anti-vector immunity, at least based on experiments done in mice and monkeys. Given the low levels of anti-Ad35 immunity in human populations, Ad35 and Ad35-related vectors have a substantial advantage over Ad5 vectors in this regard. In other words, Ad35, Ad35fib5 and Ad35k5 vectors are not substantially suppressed by anti-vector immunity. However, Ad35 vector-based vaccines are less immunogenic than Ad5 vector-based vaccines in terms of antibodies against the antigenic insert.

Importantly, it is now for the first time shown by the inventors of the present invention that low-neutralized vectors carrying at least a (heterologous) knob domain of a different, but highly immunogenic vector are substantially more potent in inducing an immune response than the backbone vector with its native fiber. Thus, such vectors represent a technical and practical advance over currently available adenoviral vectors. A person skilled in the art will be able to utilize the knowledge herewith provided to clone other adenoviral vectors based on the same principle. For instance, the invention also relates to recombinant simian adenoviruses that carry a knob domain of a fiber of an immunogenic human adenovirus. Besides recombinant simian adenoviruses other non-human adenoviruses, such as recombinant bovine and canine adenoviruses are encompassed by the present invention. It also relates to other low-neutralized human adenoviruses that can be employed as backbone vectors that carry at least a knob domain of other immunogenic adenoviruses. The different combinations are numerous, but limited to the extent that at least the hexon protein of the adenovirus should not encounter a high level of pre-existing immunity, while at least the knob domain delivers the recognition of the CAR receptor, thereby ensuring a high immune response in the host to which the vector is administered. A person of general skill in the art will be able to distinguish the described features by using the general knowledge in the art for determining pre-existing immunity, determining the level of immune responses elicited and the strategies for obtaining recombinant (chimeric) vectors as outlined by the present invention.

The potent immunogenicity of Ad35k5 vaccine vectors suggests a functionally relevant role of the Ad5 fiber protein. The Ad5 fiber knob determines binding to the high-affinity receptor CAR and also plays an important role in the efficient intracellular trafficking of viral particles to the nucleus. The enhanced immunogenicity of Ad35k5 vectors likely reflects the known biologic functions of the Ad5 fiber knob, although the precise mechanisms have not yet been determined. The recombinant Ad35k5 vectors exhibit primarily the neutralization profile of the recombinant Ad35 vector and effectively evaded low/moderate levels of anti-Ad5 immunity, as shown herein. These observations are consistent with previous studies demonstrating that Ad5-specific NAbs are primarily directed against the Ad5 hexon protein. Supporting this model is also the observation that Ad5 vectors containing the Ad35 fiber protein were unable to circumvent anti-Ad5 immunity (Ophorst et al. 2004). However, high levels of anti-Ad5 immunity were in fact able to reduce the immunogenicity of Ad35k5 vectors, as shown herein, likely reflecting the lower titer but clearly detectable NAbs directed against the Ad5 fiber protein. It is to be noted that the reduction of Ad35k5 immunogenicity by anti-Ad5 immunity was only partial and was detectable only at particularly high Ad5-specific NAb titers.

Another limitation of Ad35k5 vectors may be their relatively high vp/pfu ratios, which were approximately 10-fold higher than those typically observed with Ad35 vectors. This observation suggests that viral integrity and stability may be compromised by the inclusion of a chimeric fiber protein, although this yet needs to be investigated and confirmed.

As outlined herein, the rhesus monkey studies comparing the immunogenicity of Ad5, Ad35k5, and Ad35 vectors confirmed the results obtained in mice. This is relevant since mice lack the optimal Ad35 receptor CD46 and may therefore underestimate the immunogenicity of Ad35 vectors. In rhesus monkeys, Ad5 vectors elicited rapid and high titers of vector-specific NAbs, which effectively prevented a homologous boost immunization as expected. In contrast, both Ad35 and Ad35k5 vectors elicited lower vector-specific NAb titers as compared with Ad5 vectors, which facilitated boosting of these responses following re-administration of homologous vectors. It is speculated that the robust immune responses observed in the monkeys that received Ad35k5 vectors likely reflected the fact that these vectors both primed robust responses and could be boosted effectively.

The present invention demonstrates that capsid chimeric recombinant Ad vectors can be constructed to combine beneficial immunologic and serologic properties of different Ad serotypes. The generation of chimeric Ad vectors represents a novel strategy that leads to improved second-generation Ad vectors for both vaccination and gene therapy.

According to a preferred embodiment, the present invention relates to a replication-defective recombinant adenovirus serotype 35 (Ad35) vector comprising a chimeric fiber protein comprising at least a knob domain from a CAR-binding adenovirus serotype, wherein said recombinant vector further comprises a therapeutic nucleic acid of interest. A therapeutic nucleic acid is defined as a nucleic acid, which encodes a therapeutic proteinaceous substance, such as a protein, a peptide or a polypeptide, which is useful in the diagnostic, therapeutic and/or prophylactic treatment of mammals, preferably humans. Examples of therapeutic proteins are proteins that elicit immune responses in tumor vaccination. Other examples are proteins that are useful in therapy of genetic disorders, such as those used in gene therapy. Preferred therapeutic proteins are proteins derived or based on or (directly) cloned from bacteria, parasites or infectious entities such as viruses. Adenoviral vectors are highly applicable for vaccination purposes against viruses such as Human Immunodeficiency Virus (HIV), SIV, Ebola virus, rabies virus, Herpes Simplex Virus (HSV), Hepatitis C virus (HCV), etc. Examples of HIV-derived antigens that may be encoded in the adenoviral nucleic acid are nef, gag, pol and env. An example of an HSV antigen is antigen 9D. Therapeutic proteins from parasites such as those that cause malaria may also be used in the vectors of the present invention. Particularly preferred proteins that may be cloned in these vectors are those from *Plasmodium falciparum*, such as the circumsporozoite (CS) protein and LSA-1. Other preferred proteins may be those from *Mycobacterium* strains, particularly those that cause tuberculosis, such as *Mycobacterium tuberculosis*. Preferred antigens from this bacterium are the 10.4, 85A, 85B and 85C antigens, which may thus also be used in the vectors of the present invention. Proteins used as markers for in vitro studies are typically not seen as therapeutic proteins, so GFP, luciferase, or CAT are not regarded therapeutic.

Suitable promoters and poly(A) sequences that may be used to express the antigens are well known in the art and include, but are not limited to CMV, Ad2 MLP, SV40, etc. Suitable transcription termination sequences may for example be derived from SV40 or BGH. The coding sequences of the antigens may be codon-optimized for optimal expression in mammals, preferably humans. Methods for codon-optimization are well known in the art.

The invention relates to a replication-defective recombinant adenovirus selected from the group consisting of adenovirus serotypes 11, 24, 26, 34, 35, 48, 49 and 50, said adenovirus comprising a chimeric fiber protein comprising at least a knob domain from a CAR-binding adenovirus serotype, and wherein said recombinant vector further comprises a heterologous nucleic acid coding for a therapeutic or an antigenic protein of interest. A preferred serotype is a subgroup B serotype, more preferably serotype 11, 34 and 35, most preferably serotype 35 (Ad35). The invention relates to these serotypes since they encounter neutralizing pre-existing immunity in a significantly low percentage of human sera samples that are taken from healthy individuals worldwide. Chimeric fiber proteins as used herein refers to fibers that comprise parts from at least two different adenovirus serotypes, wherein the knob domain is from an adenovirus that binds to CAR. It is preferred that the tail domain of the fiber protein is of the backbone vector as this adds to the stability of the vector through a proper interaction with the capsid of the vector. In a preferred embodiment the knob domain that binds to CAR is from a fiber of an adenovirus serotype of subgroup C, more preferably from serotype Ad5.

A therapeutic protein of interest as used herein relates to proteins that are useful in mammalian therapeutic treatment, such a gene therapy. An antigenic protein of interest as used herein relates to a protein of interest towards which an immune response is invoked upon expression in the host, or in the host cells. This immune response is required for different kinds of vaccination settings: One example is tumour vaccination in which the immune response towards the antigenic protein of interest adds to the removal of tumour cells that express the protein, while another preferred application is in prophylactic treatment such as vaccination to prevent or to significantly inhibit the infection of the host by pathogens, such as viruses, bacteria, yeast, or parasites. Thus, preferably, said antigenic protein of interest comprises a protein from a virus, a bacterium, a parasite or yeast. The use of recombinant adenoviruses according to the invention may also be used in invoking immune responses towards the antigenic proteins of interest in the course of a treatment of an infection that has already occurred, thus to prevent replication, packaging, etc. In other words, the vectors may also be used to prevent the spreading of the virus from the already-infected host to the next.

In one embodiment, the recombinant adenovirus according to the invention comprises a heterologous nucleic acid, which is under the control of a heterologous promoter.

In a preferred aspect of the invention, said antigenic protein comprises a protein from a virus, wherein said virus is a retrovirus, HSV or an Ebola virus, whereas it is preferred that if the antigenic protein is of a retrovirus, said virus is a simian or a human immunodeficiency retrovirus, wherein said heterologous nucleic acid preferably comprises one or more genes selected from the genes encoding the group of immunodeficiency virus proteins consisting of: gag, pol, env and nef.

In another aspect of the invention, said antigenic protein of interest is from a malaria-causing parasite, wherein said protein is preferably a circumsporozoite protein, or a Liver Specific Antigen (LSA-1, LSA-3), or an immunogenic part thereof, from a *Plasmodium* species, more preferably *Plasmodium falciparum*.

The invention relates to novel replication-defective recombinant adenoviruses comprising a heterologous nucleic acid and a chimeric fiber, wherein said adenovirus is selected from the group consisting of adenovirus serotypes 11, 24, 26, 34, 35, 48, 49 and 50, for use as a medicament.

The invention furthermore relates to the use of a recombinant adenoviral vector according to the invention in the manufacture of a medicament for the prophylactic or therapeutic treatment of a malaria-, an Ebola-, an HSV-, an HCV-, or an HIV infection.

In one particularly preferred embodiment, the invention relates to a chimeric replication-defective recombinant adenovirus comprising the knob domain from the fiber of Ad5, having the amino acid sequence as underlined in FIG. 2B, and a hexon protein from a serotype different from Ad5, wherein it is further preferred that said hexon protein is from a low-neutralized adenoviral serotype. Low-neutralized serotypes are those serotypes that encounter pre-existing neutralizing activity in the form of NAbs in the minority of samples from healthy individuals. In one specific embodiment, the invention relates to a chimeric replication-defective recombinant Ad35 vector comprising an Ad35 hexon and a chimeric fiber protein, said chimeric fiber protein having the amino acid sequence of SEQ ID NO:2.

Hexon HVR Swaps

Since dominant Ad5-specific NAbs are primarily directed against the Ad5 hexon protein, it was reasoned that novel recombinant Ad5 vectors containing targeted mutational swaps in hexon may be able to evade dominant Ad5 hexon-specific NAbs. This is not a new thought and several attempts in the art were made to produce such 'stealth' adenoviral vectors. However, none of them proved successful, as outlined below.

More than 99% of amino acid variability among hexon proteins from different serotypes seems to be concentrated in seven relatively short hyper variable regions (HVR's) that are located on the exposed surface of the hexon as identified by Crawford-Miksza and Schnurr (1996). These authors compared the hexon proteins of 15 different adenoviruses (Ad1, Ad2, Ad5, Ad6, Ad8, Ad9, Ad12, Ad15, Ad16, Ad31, Ad40, Ad41, Ad48, BAV3 and MAV1). The seven HVR's were identified among the 250 variable residues in loops 1 and 2 (also referred to as l1 and l2), wherein HVR1-HVR6 are in loop 1 and HVR7 is in loop 2. Crystal and co-workers (see WO 98/40509; U.S. Pat. No. 6,127,525; U.S. Pat. No. 6,153,435) replaced the entire loop 1 and 2 of the backbone vector (Ad5) with loops 1 and 2 of Ad2 (Gall et al. 1998) based on the findings of Crawford-Miksza et al. (1996). Also a vector was made in which only loop 2 was replaced. Viable viruses were produced. Ad2 and Ad5 are both subgroup C adenoviruses and cross-neutralization was still present, even after replacement of both loops, indicating that such swaps would not result in vectors that would have a decreased ability or inability to be recognized by a neutralizing antibody directed against the wild type adenovirus hexon protein, at least not when the swaps are within the same subgroup. To nevertheless try to obtain such vectors, they also tried to exchange the loops of Ad5 and replace them with the loops of Ad7. These attempts failed, no viable virus was produced, indicating that swaps from one subgroup to another were impossible to make, at least based on the identification of HVR's by Crawford-Miksza. Of course, with the knowledge of the viral genomic structure at hand, the necessary genetic modification can be achieved via general molecular biology techniques, resulting in plasmids/cosmids that should encode for the entire recombinant (chimeric) virus. However, for unknown reasons, but most likely due to the rather critical aspects of the complex hexon structure and its role in capsid formation, viable viruses were not obtained when the hexon-coding region was modified (Rux et al. 2003). Gall et al. (1998) suggested exchanging only the external loops instead of exchanging the entire hexon. It was also mentioned that the other capsid proteins, such as penton may have significant neutralization epitopes to explain the failure with the Ad5-Ad2 swaps.

The inventors of the present invention also tried to generate chimeric adenoviruses based on Ad5 carrying chimeric hexon proteins comprising the HVR's of Ad35 or Ad48 in place of the Ad5 HVR's, as guided by Crawford-Miksza and Schnurr (1996) and as further outlined by Rux and Burnett (2000). These attempts failed. This was in concert with the findings of Crystal et al. who also could not show any production of recombinant viruses, wherein the hexon parts from different subgroups were exchanged (see above).

To tackle this matter, Rux et al. (2003) showed new high-resolution crystallographic refinements that were made of the Ad2 and Ad5 hexon structures to resolve earlier found differences in Ad2 and Ad5 hexon structures. This resulted in a new definition of the regions within the hexon protein, indicating nine HVR's instead of seven. Rux et al. (2003) also identified parts of the hexon protein that should not be violated when designing novel adenovirus-based vectors.

The inventors of the present invention also tried to produce chimeric adenoviruses comprising chimeric hexon proteins with swapped HVR's, based on the definitions provided by Rux et al. (2003). However, again, no viable viruses could be produced. Clearly, based on the definitions provided in the art regarding the hexon HVR's, recombinant adenoviruses having one or more of the HVR's exchanged between a backbone vector and another serotype, at least between adenovirus serotypes of different subgroups, could not be produced.

The inventors of the present invention have now identified seven HVR's within human adenoviruses that differ from the seven HVR's identified by Crawford-Miksza and Schnurr (1996) and that also differ from the nine HVR's identified by Rux et al. (2003). The broad definition according to the invention is indicated in Table II, whereas an even more minimalistic definition is provided in Table IV. Replacement of these HVR's alone resulted in the production of viable virus. To the best of the knowledge of the inventors, this is the first time that anyone has been able to generate chimeric adenoviruses comprising chimeric hexon proteins, wherein not entire loops are exchanged, but wherein the distinct HVR's are exchanged. It is also held that this is the first successful attempt in obtaining recombinant adenoviruses comprising chimeric hexon proteins, wherein the hexons comprise parts from adenovirus serotypes from two different subgroups. The conceptual basis for the re-definition of the HVR's was to use conserved amino acids as junction points. It can nevertheless not be excluded that by shifting one or two or perhaps even three amino acids towards the N-, and/or C-terminus may yield in viable vectors. However, the definitions as previously provided in the art, were not sufficient to provide viable vectors with chimeric hexons. The definitions as provided herein are nevertheless not to be taken too strictly, as slight shifts may also provide good results (see Table II in comparison with Table IV). Preferably, the identified HVR sequences (as represented by SEQ ID NO:17-79 and 88-150) are the regions that are swapped between serotypes.

Ad5-based vectors containing one or more HVR's, exchanged from Ad35 (subgroup B) or Ad48 (subgroup D) were constructed as disclosed in the examples. Clearly, one or more HVR's can be exchanged. As it is likely that NAbs are directed to any of the HVR's it is preferred to have most, if not all HVR's from a rare serotype in place of the wild type HVR's of the backbone vector. On the other hand, such large swaps might result in more-difficult-to-produce viable vectors. Herein, it is now disclosed that all seven identified HVR's within the backbone vector (exemplified by Ad5) can be replaced by the seven corresponding HVR's of a rare serotype (exemplified by Ad48). This also suggests that swaps based on the HVR* definitions of Table IV will also result in viable viruses.

The spacer regions between the HVR's preferably remain to be of the backbone serotype to ensure proper folding of the protein. The preferred backbone is Ad5, although other-, generally used and widely applied serotypes form subgroup C, such as Ad2 can also be used. When HVR's are swapped, preferably at least one, more preferably two, even more preferably three, even more preferable four, even more preferably five, even more preferably six and most preferably seven HVR's are swapped.

The Ad5HVR35 and Ad5HVR48 vectors that were generated as disclosed herein are substantially more immunogenic than recombinant Ad5 vectors in the presence of anti-Ad5 immunity, because NAbs, which are primarily directed against the hexon protein of Ad5 in Ad5-infected individuals, are no longer able to neutralize through the HVR's of hexon of Ad35 and Ad48. This feature holds true for all HVR's taken from all known rare serotypes, which may be selected from Ad11, Ad24, Ad26, Ad34, Ad35, Ad48, Ad49 and Ad50.

As shown below, Ad5HVR48(1-7) viruses, containing all seven HVR's of Ad48 in place of the seven HVR's of Ad5, results in a virus that is not hindered by a pre-existing immunity induced by a pre-injection with Ad5 virus. This now enables one to use Ad5-based vectors in numerous settings, for instance in prime-boost regimens wherein it is required that the receptor recognition between the priming vector and the boosting vector remains the same. Another application would be the vaccination or therapeutic application with an Ad5-based vector in individuals that have encountered wild type Ad5 infection previous to the treatment.

Based on the identification of the HVR's as disclosed herein, numerous combinations between backbone vectors and other adenovirus serotypes are now feasible. The knowledge can be extrapolated to the hexons of all known human and non-human adenoviruses. Whenever a prime-boost regimen is required (not only for settings in which Ad5-based vectors are required), the knowledge provided herein can be applied to construct a vector with stealth-capacity, namely circumvention of pre-existing immunity against the hexon HVR's present in the previous applied virus. It is to be understood that the chimeric HVR vectors as disclosed herein can be further modified by methods known in the art. For instance, the fiber may be altered to yield a specific targeting ability (e.g., fiber knobs from subgroup B viruses, placed on subgroup C based vectors may be targeted to smooth muscle cells, primary fibroblasts, dendritic cells, etc.). An example of such a vector would be an Ad5 based vector comprising the HVR's from for instance Ad48 and at least the fiber knob (the main determinant of receptor recognition) from for instance Ad35. Such vectors all fall within the scope of the present invention related to adenoviral vectors comprising hexons that are chimeric with respect to their HVR's.

The person skilled in the art will now be able, with the knowledge provided herein, to construct and to produce viable recombinant replication defective adenoviruses, which have one or more HVR's replaced by HVR's from other adenoviruses. Moreover, the sequences of the HVR's provided herein will now enable one to remove those sequences and to use these positions within the hexon to introduce other substances, such as targeting ligands to target the adenoviruses to cells of interest (in vivo and in vitro), radioactive binding sites for tracking adenoviruses in vitro, and certain B-cell epitopes (such as described by Worgall et al. 2005).

The present invention relates to a batch of a recombinant replication-defective adenovirus based on a serotype from a first subgroup, said adenovirus comprising a chimeric hexon protein wherein said hexon protein comprises sequences from the serotype of said first subgroup and at least one hyper variable region (HVR) sequence from a serotype from a second subgroup, wherein said first and said second subgroup are not the same. Preferably, said first subgroup is subgroup A, C, D, E, or F. Also preferred are batches according to the present invention wherein said second subgroup is subgroup B or D. More preferred are batches, wherein said first subgroup is subgroup C, and the serotype from said subgroup C is Ad5, and wherein said serotype from subgroup B or D is selected from the group consisting of: Ad11, Ad24, Ad26, Ad34, Ad35, Ad48, Ad49 and Ad50.

In a preferred embodiment of the present invention, said chimeric hexon protein comprises the first six HVR sequences (HVR1-HVR6), or all seven HVR sequences (HVR1-HVR7) from a serotype from said second subgroup.

In another preferred embodiment, said hexon protein retains the amino acid sequences of the backbone virus between the HVR sequences. Thus, the one or more HVR sequences as defined herein may be deleted, mutated, replaced by a linker or replaced by an HVR sequence from another serotype, highly preferably, the sequences linking the HVR's are maintained and are unchanged. This enables one to produce viruses that are stable due to their hexon-backbone structure provided by the non-HVR sequences. It is thus preferred that the sequences between the HVR sequences are from the serotype from said first subgroup.

In a highly preferred embodiment, the present invention provides batches of adenoviruses according to the present invention, wherein the first subgroup is subgroup C and wherein the at least one HVR sequence from the serotype of said second subgroup is selected from SEQ ID NO:24-79 and SEQ ID NO:95-150. In an even more preferred embodiment, the HVR1 sequence is selected from SEQ ID NO:17, 24, 31, 38, 45, 52, 59, 66, and 73, wherein the HVR2 sequence is selected from SEQ ID NO:18, 25, 32, 39, 46, 53, 60, 67, and 74, wherein the HVR3 sequence is selected from SEQ ID NO:19, 26, 33, 40, 47, 54, 61, 68, and 75, wherein the HVR4 sequence is selected from SEQ ID NO:20, 27, 34, 41, 48, 55, 62, 69, and 76, wherein the HVR5 sequence is selected from SEQ ID NO:21, 28, 35, 42, 49, 56, 63, 70, and 77, wherein the HVR6 sequence is selected from SEQ ID NO:22, 29, 36, 43, 50, 57, 64, 71, and 78, and wherein the HVR7 sequence is selected from SEQ ID NO:23, 30, 37, 44, 51, 58, 65, 72, and 79. In yet another preferred embodiment, the HVR1 sequence (HVR1*) is selected from SEQ ID NO:88, 95, 102, 109, 116, 123, 130, 137, and 144, wherein the HVR2 sequence (HVR2*) is selected from SEQ ID NO:89, 96, 103, 110, 117, 124, 131, 138, and 145, wherein the HVR3 sequence (HVR3*) is selected from SEQ ID NO:90, 97, 104, 111, 118, 125, 132, 139, and 146, wherein the HVR4 sequence (HVR4*) is selected from SEQ ID NO:91, 98, 105, 112, 119, 126, 133, 140, and 147, wherein the HVR5 sequence (HVR5*) is selected from SEQ ID NO:92, 99, 106, 113, 120, 127, 134, 141, and 148, wherein the HVR6 sequence (HVR6*) is selected from SEQ ID NO:93, 100, 107, 114, 121, 128, 135, 142, and 149, and wherein the HVR7 sequence (HVR7*) is selected from SEQ ID NO:94, 101, 108, 115, 122, 129, 136, 143, and 150. More preferably, the HVR1 sequence as represented by either the HVR1 sequences in Table II or by those in Table IV are deleted from the backbone vector. The reason for deleting the HVR1 region is that according to the crystal structure of the adenovirus hexon protein, the flanking sequences of HVR1 are very close together, indicating that these flanking sequences may be directly linked without loss of structure, except for the deletion. In another preferred embodiment, the HVR2 sequence as represented by either the HVR2 sequences in Table II or by those in Table IV are replaced by a short linker, more preferably by a two-amino acid linker, most preferably by a QG linker. Also the HVR2 flanking sequences are close together, following the crystal structure. However, as they are slightly more apart than seen for HVR1, it is preferred to include a small bridging linker, preferably a linker of 1, 2, 3, or 4 amino acids, more preferably 2. Removal of HVR's from the hexon might be the ideal solution in preventing an attack by NAbs against the immunogenic determinants presented by the HVR's. However, in view of the crystal structure it does not seem feasible to delete HVR3-7 from the hexon protein without destroying its overall structure and thus possibly its function and role in capsid formation.

Although the hexon of Ad24 is also preferred for its HVR's, the sequence of the hexon protein of this specific 'rare' serotype was unknown to the inventors at the time of filing. Nevertheless, with the teaching as provided herein, the skilled person will now be able to determine the HVR's within any adenovirus hexon protein, including the preferred serotype Ad24. The use of any one of the HVR's of Ad24 is also part of the present invention.

The invention also relates to the use of an isolated nucleic acid encoding at least one HVR sequence of an hexon of a human adenovirus serotype from subgroup B in the construction of a chimeric hexon protein, which hexon further comprises sequences from an adenovirus from subgroup A, C, D, E, or F. Furthermore, the invention relates to the use of an isolated nucleic acid encoding at least one HVR sequence of an hexon of a human adenovirus serotype from subgroup D in the construction of a chimeric hexon protein, which hexon further comprises sequences from an adenovirus from subgroup A, B, C, E, or F. Preferably, the at least one HVR sequence is selected from SEQ ID NO:24-79 and 95-150.

Table III summarizes the various embodiments of the invention. The table indicates that the invention relates to a chimeric replication defective adenovirus based on a backbone adenovirus comprising a penton and hexon protein of serotype X, wherein n HVR's in the hexon protein are of serotype Y, further comprising a fiber comprising a tail and a shaft of serotype F and a knob of serotype K, wherein:

X is an adenovirus serotype selected from the group consisting of human adenoviruses 1-51, a simian-, a canine-, an ovine-, a porcine-, and a bovine serotype;

Y is an adenovirus serotype selected from the group consisting of human adenoviruses 11, 24, 26, 34, 35, 48, 49 and 50, wherein X and Y may be the same or different, and wherein n represents any number of HVR's from 0 to 7, provided that if X≠Y, that n=1-7;

F is an adenovirus serotype selected from the group consisting of human adenoviruses 1-51, a simian-, a canine-, an ovine-, a porcine-, and a bovine serotype, wherein F, X and Y may the same or different; and K is an adenovirus serotype that primarily uses CAR as cellular receptor, wherein K, F, X and Y may be the same or different. Preferably, at least part of the tail of the fiber protein that interacts with the penton protein is of serotype X in the event that F is not X.

It is to be understood that the backbone adenoviral vector may be any adenovirus (made recombinant such that it does not replicate in normal, non-packaging, cells) that is applicable for use in humans. Any of the human adenoviruses known (serotypes 1-51) within the six subgroups A, B, C, D, E, and F, as well as known simian-, canine-, bovine-, ovine-, and porcine-adenoviruses may be used as a backbone vector, as long as it is replication-defective and as long as it is applicable for human treatment. The backbone vector is replication-defective by deletion of at least one functional part of the E1 region, preferably by deletion of the entire functional E1 region. Although the backbone vector typically comprises the other early and late regions, the skilled person is aware of the possibilities provided in the art to complement certain required adenoviral proteins by other means, for instance through complementation with helper viruses or by having the packaging cell transformed such that it comprises the required nucleic acids stably integrated in its genome. Typically, the viruses of the invention comprise an adenoviral genome with an E1 deletion, and preferably also an E3 deletion to provide space for heterologous nucleic acids of interest that may be cloned in the E1 region or in the E3 region, or both. The remaining regions, such as E2, E4, the ITR's and the late regions are generally present, although these may be complemented separately during production in a packaging cell. The vectors preferably comprises an E4orf6 region (possibly from another serotype) that is compatible with the E1B-55K protein present in the packaging cell line, as disclosed in WO 03/104467. This is done to enable production on known packaging systems such as PER.C6® cells or 293 cells, when the recombinant vector has an original E4orf6 region which is not compatible with E1B-55K of Ad5 present in such cells.

The backbone serotype is indicated above as 'X'. Further, the backbone virus may be engineered such that it contains HVR's from one or more of the adenovirus serotypes selected from human Ad11, Ad24, Ad26, Ad34, Ad35, Ad48, Ad49, and Ad50 (indicated by serotype 'Y'). Clearly, when X is one of the Y serotypes, the HVR's may not have to be engineered as these serotypes are considered 'rare' and encounter only low pre-existing immunity is most individuals in the human population. So, when X is one of the Y serotypes, the number of swapped HVR's (the number indicated by 'n'), may be zero, but also 1-7, whereas, when X is not one of the Y serotypes, at least one of the HVR's is from a Y serotype, wherein it is increasingly preferred to have more HVR's from a Y serotype, and wherein it is most preferred to have all seven HVR's exchanged for the corresponding regions from a Y serotype.

The backbone virus of the present invention comprises a penton protein of the same serotype as the backbone virus. The backbone virus is 'chimeric' in the sense that either the hexon is chimeric (having one or more HVR's exchanged or substituted) and/or in the sense that the fiber protein is chimeric and/or in the sense that the fiber protein is from a different serotype than the backbone virus. The possibility exists that X=Y=F=K, for example a recombinant Ad48 vector, as Ad48 binds CAR. However, such vectors are not 'chimeric' in the sense as described above, when n=0. Not-chimeric recombinant Ad11, Ad34, Ad35 and Ad50 do not fall within the above given definition, as the fiber knob should always be from a serotype that preferentially binds CAR, which these B-subgroup viruses do not.

The fiber is from a serotype indicated as 'F', comprising a tail from serotype F, comprising a shaft from serotype F and comprising a knob from a serotype indicated as 'K'. Clearly, when K is the same serotype as F, the fiber protein is not chimeric. K is a serotype that preferentially interacts with the CAR receptor and K may be the same serotype as X or different. Clearly, certain human serotypes, such as those from subgroup B, do not preferentially interact with CAR, but preferably interact with another cellular receptor, such as CD46. So, when K is the same as X, X is not one of the subgroup B adenoviruses. Also, when K is of a different serotype than F (and the fiber is thus chimeric), at least part of the tail that interacts with penton in the capsid is of serotype X, as that would result in proper and stable capsid formation. As most of the capsid protein-encoding genes of the known adenoviruses are now available in the art, it is within the skill of the skilled artisan to identify the tail, shaft and knob region for every known and yet to be discovered adenovirus.

Preferred, but not limiting examples of chimeric replication-defective adenoviruses according to the present invention are: Ad5HVR11(1-7), Ad5HVR24(1-7), Ad5HVR26(1-7), Ad5HVR34(1-7), Ad5HVR35(1-7), Ad5HVR48(1-7), Ad5HVR49(1-7), Ad5HVR50(1-7), Ad5HVRPan9(1-7), Ad5HVR11(1-6), Ad5HVR24(1-6), Ad5HVR26(1-6), Ad5HVR34(1-6), Ad5HVR35(1-6), Ad5HVR48(1-6), Ad5HVR49(1-6), Ad5HVR50(1-6), Ad5HVRPan9(1-6), Ad5HVR11(1), Ad5HVR24(1), Ad5HVR26(1), Ad5HVR34(1), Ad5HVR35(1), Ad5HVR48(1), Ad5HVR49(1), Ad5HVR50(1), Ad5HVRPan9(1), Ad11k5, Ad24k5, Ad26k5, Ad34k5, Ad35k5, Ad48k5, Ad49k5, Ad50k5, Pan9k5, Ad11f5, Ad24f5, Ad26f5, Ad34f5, Ad35f5, Ad48f5, Ad49f5, Ad50f5, Pan9f5, Ad11k26, Ad34k26, Ad35k26, Ad50k26, Pan9k26, Ad11f26, Ad34f26, Ad35f26, Ad50f26, Pan9f26, Ad11k49, Ad34k49, Ad35k49, Ad50k49, Pan9k49, Ad11f49, Ad34f49, Ad35f49, Ad50f49, Pan9f49, Ad2HVR11(1-7), Ad2HVR24(1-7), Ad2HVR26(1-7), Ad2HVR34(1-7), Ad2HVR35(1-7), Ad2HVR48(1-7), Ad2HVR49(1-7), Ad2HVR50(1-7), Ad2HVRPan9(1-7), Ad2HVR11(1-6), Ad2HVR24(1-6), Ad2HVR26(1-6), Ad2HVR34(1-6), Ad2HVR35(1-6), Ad2HVR48(1-6), Ad2HVR49(1-6), Ad2HVR50(1-6), Ad2HVRPan9(1-6), Ad2HVR11(1), Ad2HVR24(1), Ad2HVR26(1), Ad2HVR34(1), Ad2HVR35(1), Ad2HVR48(1), Ad2HVR49(1), Ad2HVR50(1), Ad2HVRPan9(1), Ad11k2, Ad24k2, Ad26k2, Ad34k2, Ad35k2, Ad48k2, Ad49k2, Ad50k2, Pan9k2, Ad11f2, Ad24f2, Ad26f2, Ad34f2, Ad35f2, Ad48f2, Ad49f2, Ad50f2, and Pan9f2.

EXAMPLES

Example 1

International Seroprevalence and NAb Titers to Ad5, Ad35, and Ad11

Ad-specific neutralizing antibody (NAb) responses were assessed by luciferase-based virus neutralization assays generally as described by Sprangers et al. (2003). Briefly, A549 human lung carcinoma cells were plated at a density of $1 \times 10^4$ cells per well in 96-well plates and infected with E1-deleted, replication-incompetent Ad-Luciferase reporter constructs at a multiplicity of infection (moi) of 500 with 2-fold serial dilutions of serum in 200 μl reaction volumes. Following 24 h incubation, luciferase activity in the cells was measured using the Steady-Glo Luciferase Reagent System (Promega). 90% neutralization titers were defined as the maximum serum dilution that neutralized 90% of luciferase activity.

Figure 1B:
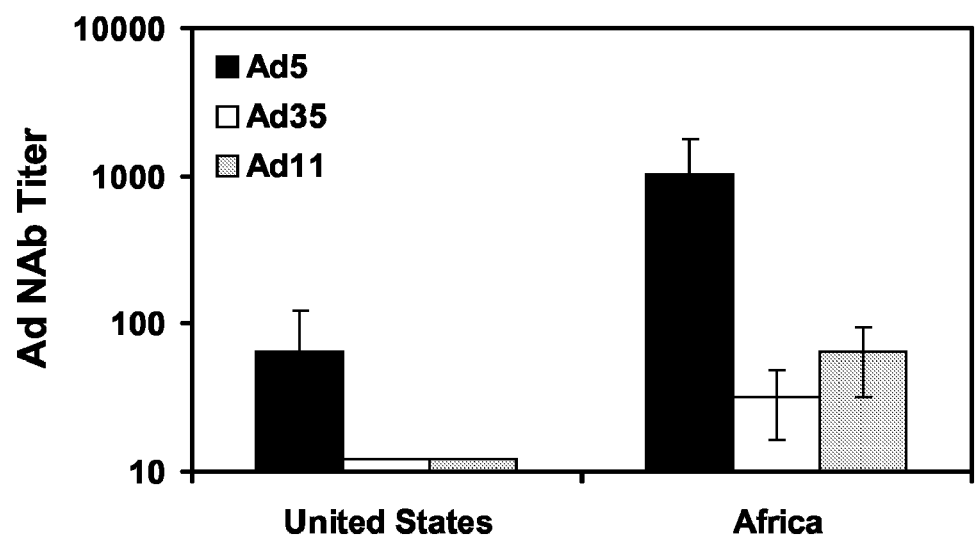
FIG. 1C shows the neutralizing antibody titer against Ad5, Ad5f35, Ad5f35p35, Ad35f5 and Ad35 in these samples.

Further to the studies disclosed in WO 00/70071, experiments were performed to assess the seroprevalence and NAb titers to Ad5 and alternate Ad serotypes in the developing world. The luciferase-based virus neutralization assays from Sprangers et al. (2003) was applied by using serum samples obtained from healthy adults in the United States (N=19), Haiti (N=67), Botswana (N=57), Zambia (N=29), and South Africa (N=59). As shown in FIG. 1A, the Ad5 seroprevalence was 50% with relatively low median titers in the United States. In contrast, the Ad5 seroprevalence was 82% in Haiti, 93% in Botswana, 93% in Zambia, and 88% in South Africa. Moreover, the median Ad5-specific NAb titers in these samples were >10-fold higher than the median titers found in the United States (FIG. 1B). These data extend the previous findings (Kostense et al. 2004; Vogels et al. 2003) and demonstrate that Ad5-specific NAbs are nearly universal and present in high titers in the developing world. In contrast, the Ad11 and Ad35 seroprevalence and titers were substantially lower in these populations.

Example 2

Immunodominant Targets of Ad5-Specific Neutralizing Antibodies

The samples outlined in the previous example were further utilized to determine the dominant antigenic targets of Ad5-specific NAbs in both the USA and sub-Saharan Africa. Given the lack of detectable NAb cross-reactivity between Ad5 and Ad35, the capsid chimeric Ad5/Ad35 viruses expressing luciferase as targets in virus neutralization assays were used. These vectors consist of various combinations of Ad5 and Ad35 hexon, penton, and fiber proteins in the context of intact virus particles with wild-type growth kinetics (Havenga et al. 2002; Rea et al. 2001). The chimeric vectors used in this study included Ad5f35 (Ad5 containing the Ad35 fiber knob, -shaft and an Ad35-Ad5 chimeric tail), Ad5f35p35 (Ad5 containing the Ad35 fiber and -shaft, the Ad35-Ad5 chimeric tail, and penton), and Ad35f5 (Ad35 containing the Ad5 fiber knob, -shaft and an Ad5-Ad35 chimeric tail).

Figure 1C:
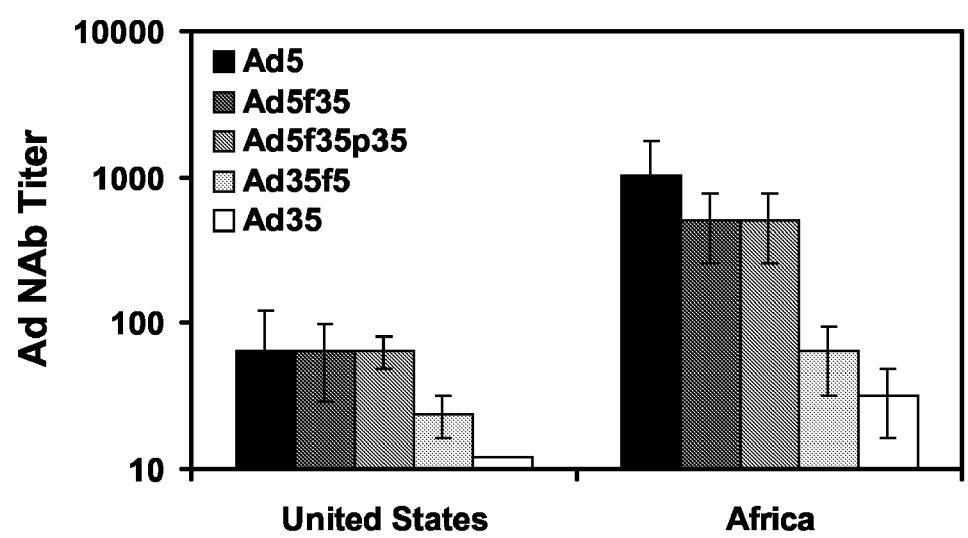

As shown in FIG. 1C, comparable NAb titers were observed against Ad5, Ad5f35, and Ad5f35p35; all based on Ad5. Since the capsid of the Ad5f35p35 vector contains the Ad5 hexon but the Ad35 derived fiber and Ad35 derived penton, these data suggest that the majority of Ad5-specific NAb activity was directed against the Ad5 hexon. Lower but clearly detectable titers were also measured against recombinant Ad35f5 (herein also referred to as Ad35fib5), demonstrating that Ad5 fiber-specific NAbs were present at 5- to 10-fold lower titers than Ad5 hexon-specific NAbs in these samples. No Ad5 penton-specific NAbs were measured using these viruses, but the similar NAb titers against Ad5f35 and Ad5f35p35 suggested that penton-specific NAbs played at most a relatively minor role in this neutralization.

Example 3

Generation of Ad35f5 and Ad35k5

Recombinant Ad35-based vaccines are immunogenic in the presence of anti-Ad5 immunity. However, recombinant Ad35 vaccines are intrinsically less immunogenic than recombinant Ad5 vaccines in the absence of anti-Ad5 immunity (Barouch et al. 2004). This problem has now been overcome by constructing capsid chimeric recombinant Ad35 vectors in which at least the Ad35 fiber knob is replaced with the Ad5 fiber knob (referred to as Ad35k5 for the knob replacement and Ad35f5 for most of the fiber replacement).

Recombinant Ad35k5 vectors were produced by replacing the Ad35 fiber protein-encoding gene with a chimeric fiber protein-encoding gene consisting of the Ad35 fiber tail and shaft (amino acids 1-132) linked to the Ad5 fiber knob (amino acids 133-314). Ad5 fiber-specific antibodies do not blunt recombinant Ad5 vaccine immunogenicity. The Ad35 fiber knob does not interact with CAR since it is a subgroup B adenovirus (Roelvink et al. 1998) but instead utilizes CD46 as its receptor (Gagger et al. 2003). The different fiber proteins direct these viruses into different intracellular trafficking pathways. Previous studies have shown that the Ad5 fiber knob facilitates rapid viral escape from early endosomes into the cytosol, leading to efficient translocation of viral genomes into the nucleus, whereas the fiber knobs from subfamily B adenoviruses, including Ad11 and Ad35, lead to retention of virus particles in late endosomes and recycling of a large fraction back to the cell surface (Shayakhmetov et al. 2003).

The cloning of the recombinant nucleic acid encoding the Ad35k5 vector was as follows. The region encoding the Ad5 fiber knob was synthesized by PCR and was cloned as a BsiWI-NheI fragment into the pBR.Ad35.PacI-rITR.dE3 plasmid (=pBr.Ad35.PRnΔE3 in WO 2004/001032) to replace the corresponding region encoding the Ad35 fiber knob. The mutant pBR.Ad35k5.PacI-rITR.dE3 plasmid together with the pWE.Ad35.pIX-EcoRV (WO 2004/001032) cosmid and the adaptor plasmid pAdApt35-SIV-Gag, comprising the SIVmac239 Gag gene, were then co-transfected into PER.C6/55K cells (see WO 00/70071 and WO 02/40665), and double homologous recombination yielded the recombinant Ad35k5-SIVGag vector. This vector was plaque-purified, sequenced, expanded, and purified by CsCl gradient centrifugation following general purification methodology known to the skilled person. The nucleotide sequence of the chimeric fiber is shown in FIG. 2A (SEQ ID NO:1), while the amino acid sequence is shown in FIG. 2B (SEQ ID NO:2).

The Ad35f5 vector was typically made as outlined for Ad35fib16 in WO 00/70071, and Ad5fibXX chimeras as outlined in WO 00/03029; wherein a PCR product encoding a partial tail of Ad5 fiber linked to the Ad5 fiber shaft and Ad5 fiber knob were placed on the remaining part of the Ad35 fiber tail. The cloning procedure was also performed using an E3 deleted backbone vector and using BsiWI and NheI as restriction/cloning sites. For vector details see WO 03/104467 and WO 2004/001032.

In detail, the following procedures were performed to construct pBr/Ad35.pacI-rITRfib5: A PCR was performed on the plasmid pBr/Ad35.PacI-rITRNotI (=pBr/Ad35.PRn see WO 2004/001032) with primer DF35-1: 5'-CAC TCA CCA CCT CCA ATT CC-3' (SEQ ID NO:6) and DF35-2: 5'-CGG GAT CCC GTA CGG GTA GAC AGG GTT GAA GG-3' (SEQ ID NO:7) containing a BamHI and a BsiWI site. This PCR resulted in a DNA fragment of approximately 650 bp, starting in the fiber 35 tail region, by which both a BsiWI site and a BamHI site was introduced. Next, a PCR was performed on plasmid pBr/Ad35.PRn with primer DF35-3: 5'-CGG GAT CCG CTA GCT GAA ATA AAG TTT AAG TGT TTT TAT TTA AAA TCA C-3' (SEQ ID NO:8) containing a BamHI and a NheI site and DF35-4: 5'-CCA GTT GCA TTG CTT GGT TGG-3' (SEQ ID NO:9). This PCR resulted in a DNA fragment of approximately 1400 bp, starting after the stop codon of fiber 35 to the E4 region. pBr/Ad35.PRn was digested with MluI and NdeI, removing a 2850 bp DNA fragment from the Ad35 backbone (thus removing most of the fiber 35 region). The PCR fragment from DF35-1+DF35-2 was digested with MluI and BamHI and the PCR fragment from DF35-3+DF35-4 was digested with BamHI and NdeI. Both PCR fragments were ligated into the cut pBr/Ad35PRn plasmid, resulting in the pBr/Ad35PRndFIB construct. Then, the newly introduced BsiWI and NheI sites were used to introduce the Ad5 fiber sequence into the Ad35 backbone, by producing a PCR product using primers 35F5-5-F: 5'-CGG GAA CGT ACG ACA CGG AAA CCG GTC CTC C-3' (SEQ ID NO:10) and 35F5-R: 5'-CGG CTA GCT AGC TTA TTC TTG GGC AAT GTA TGA AA-3' (SEQ ID NO:11) on Ad5 DNA as a template. After this, the E3 region was deleted as performed for de pBr/Ad35PRNdE3 construct.

A person skilled in the art will be able, by applying general common knowledge with respect to molecular cloning and adenoviral production, to generate these clones, to insert fragments, to generate PCR products and to delete certain fragments and to eventually produce viruses in packaging cell lines. Moreover, production and purification methods for obtaining adenoviral batches that can be used in vivo and in vitro are also well known in the art.

All vectors discussed herein were obtained using general CsCl purification methods and were found to be stable over at least 5 passages on PER.C6/55K packaging cell lines (data not shown). Growth rates and yields of Ad35k5 vectors were comparable with parental Ad35 vectors (data not shown). However, ratios of viral particles (vp) to plaque-forming units (pfu) were approximately 10-fold higher for Ad35k5 vectors (100-1000) as compared with Ad35 vectors (10-100).

It was also investigated whether the vectors were still able to recognize their respective receptors through their natural- or replaced fiber knobs (Ad5 fiber binding to CAR and Ad35 fiber binding to CD46). These specific interactions were still established with the chimeric vectors as well as with the original Ad5 and Ad35 based vectors (data not shown).

Following the same strategies, chimeric replication-defective Ad35-based viruses were made comprising the knob of Ad26 or Ad49. These viruses are named Ad35k26 and Ad35k49 and use the CAR-binding capacity of the fiber knob of the rare serotypes Ad26 and Ad49 in combination with the hexon protein present in the capsid of the backbone vector, which is also a rare serotype, exemplified herein by Ad35. The nucleic acid and amino acid sequences representing the respective Ad35k26 and Ad35k49 chimeric fibers are given in FIG. 2E-2H.

Figure 16:
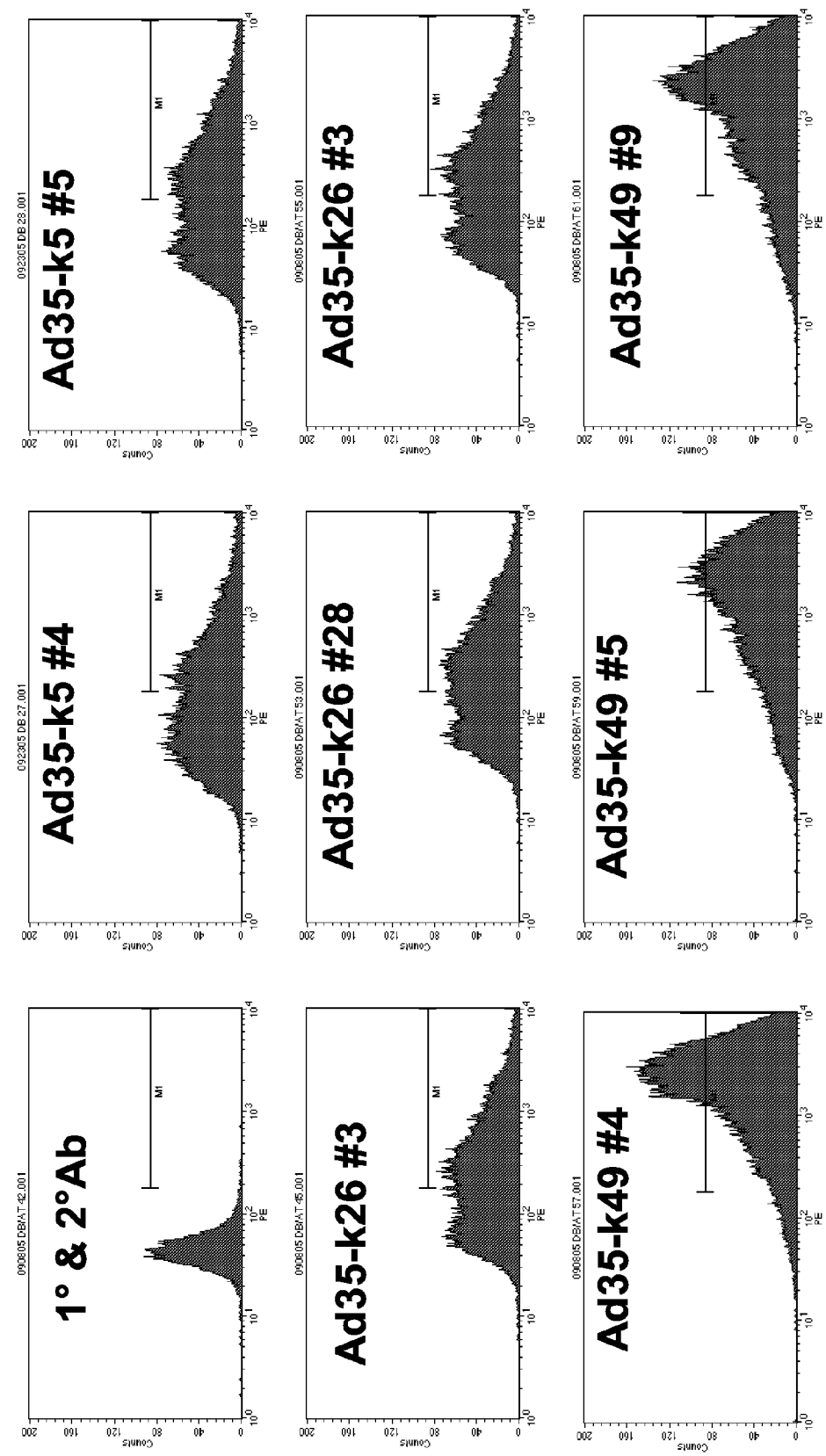
FIG. 16 shows the intracellular gag-staining in a background setting (no infection, graph 1° & 2° Ab) and after infection with Ad35k5 (two batches: #4, #5), with Ad35k26 (two batches: #3 twice, #28) and with Ad35k49 (three batches: #4, #5, #9).

Ad35k5, Ad35k26 and Ad35k49 viruses were compared in their ability to provide transgene expression in vitro. All vectors carried the SIVGag transgene. $7.5 \times 10^4$ A549 cells were infected with master virus seed stock viruses (unknown concentration of virus) for 2 h in a 2 ml volume. Cells were then washed and cultured for 48 h. Gag staining was evaluated by intracellular staining using the 2F12 anti-p27 monoclonal antibody followed by analysis by flow cytometry. The limitation of this experiment is that a specific number of viral particles was not used, and thus it cannot be concluded definitively whether Ad35k49 grows to higher titer than the others or whether it has higher specific activity. In any way, this vectors seems to have certain advantages over the other vectors, either in replication/growth or in expression levels. FIG. 16 shows that three representative batches of Ad35k49 showed a significant higher intracellular expression as compared to representative batches of Ad35k5 and Ad35k26. The recombinant adenoviral vector Ad35k49 is a preferred embodiment of the invention.

For a good production of adenoviral vectors on packaging cells it is realized in the art that the E1B-55K protein, generally available by a stable integration of its gene in the genome of the packaging cell, should be compatible with the E4orf6 protein produced by the E4 region of the viral vector. It was found previously that the E4orf6 protein of Ad35 was not compatible with the E1B-55K protein generally available in known packaging cells such as 293 cells and PER.C6® cells (see WO 03/104467; WO 2004/001032; WO 2004/018627; WO 95/34671). To circumvent using new cell lines with E1B-55K from Ad35 integrated in the genome, and thus to enable one to use established production platforms as those provided by PER.C6 cells, further constructs were made in which the E4orf6 region of the Ad35 backbone was replaced with the E4orf6 region from Ad5, in line as what has been described in detail in WO 03/104467. The replacement of the E4orf6 region was applied in all Ad35-based vectors, but not further used in the immunogenicity studies and targeting studies described herein.

Example 4

Immunogenicity of Recombinant Ad35f5 and Ad35k5 in Comparison with Ad5 and Ad35

The immunogenicity of the vectors was assessed by comparison of the chimeric fiber carrying vectors to Ad5-SIVGag and Ad35-SIVGag.

Naïve mice (N=5/group) were immunized intra-muscularly with $10^{10}$ vp Ad5-SIVGag, Ad35-SIVGag, Ad35.BSU.SIVGag and Ad35fib5.BSU.SIVGag. The term BSU relates to the use of the endogenous pIX promoter in the adenoviral genomic nucleic acid, which ensures a proper expression of the pIX gene during the production of Ad35-based recombinant viruses. For details relating to the BSU constructs, see WO 2004/001032. Control mice (N=3/group) were immunized with empty Ad5 and Ad35 vectors. After 28 days a blood sample was taken and immune responses were determined using a SIV gag ELIspot assay as described below.

Figure 3:
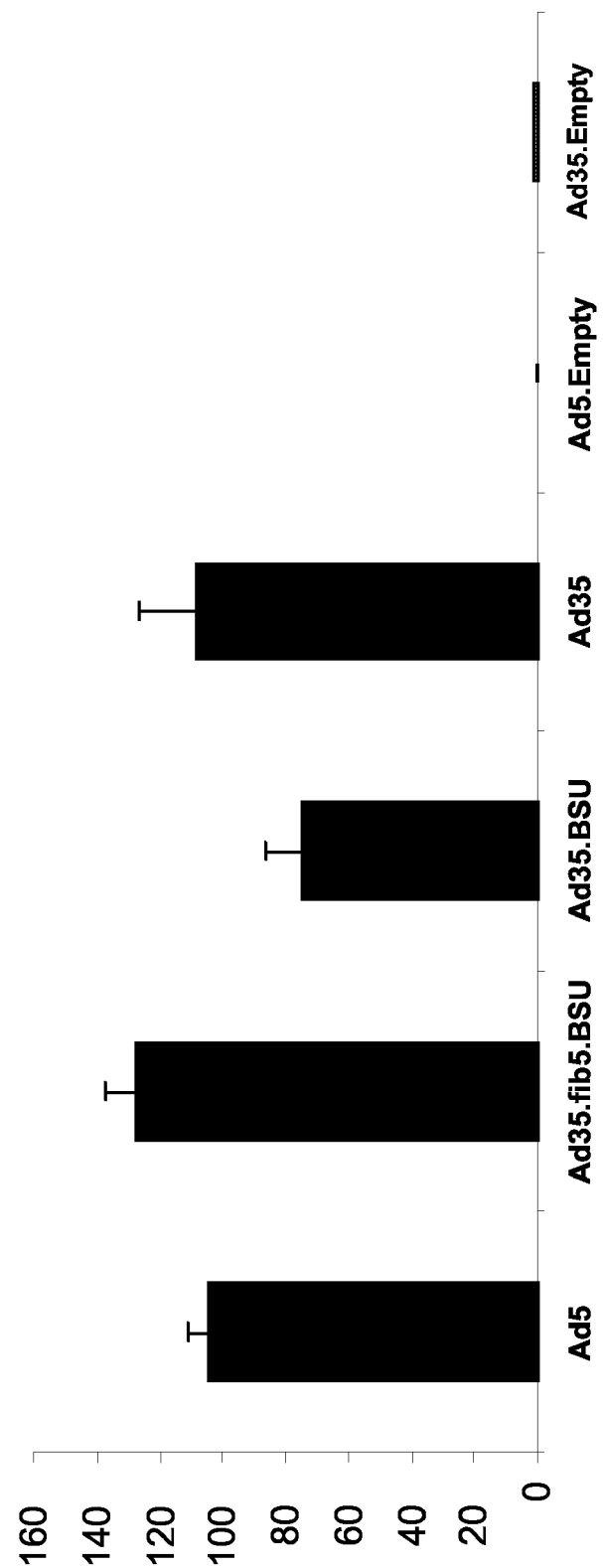
FIG. 3 shows the T cell response induced towards SIV gag upon injection of naïve mice with Ad5, Ad35fib5.BSU, Ad35.BSU and Ad35 vectors carrying the SIV gag-encoding gene in comparison to mice injected with empty vectors (Ad5.empty and Ad35.empty). The y-axis depicts SFC/$10^6$ splenocytes.

FIG. 3 shows the results of these experiments and indicates that all vectors were able to induce a proper T cell response towards the SIV gag protein in comparison to the empty vectors, indicating that the insert provides an immunogenic protein upon injection in mice.

Another set of naïve mice (N=8/group) were immunized with $10^9$ vp or $10^8$ vp of the Ad5-Gag, Ad35-Gag, and Ad35k5-Gag vectors (all encoding the SIV gag protein). Vaccine-elicited CD8$^+$ T lymphocyte responses were assessed by $D^b$/AL11 tetramer binding assays using the following method: Tetrameric H-2D$^d$ complexes folded around the dominant SIVmac239 Gag AL11 epitope peptide (AAVKN-WMTQTL; SEQ ID NO:3; Barouch et al. 2004) were prepared and utilized to stain P18-specific CD8$^+$ T lymphocytes from mice using methods known in the art. Mouse blood was collected in RPMI 1640 containing 40 U/ml heparin. Following lysis of the Red Blood Cells, 0.1 µg of PE-labeled $D^d$/P$_{18}$ tetramer in conjunction with APC-labelled anti-CD8alpha mAb (Ly-2; Caltag, Burlingame, Calif., USA) was utilized to stain P18-specific CD8$^+$ T lymphocytes. The cells were washed in PBS containing 2% FBS and fixed in 0.5 ml PBS containing 1.5% paraformaldehyde. Samples were analyzed by two-color flow cytometry on a FACS Calibur (Becton Dickinson). Gated CD8$^+$ T lymphocytes were examined for staining with the $D^d$/P18 tetramer. CD8$^+$ T lymphocytes from naïve mice were utilized as negative controls and exhibited <0.1% tetramer staining.

As shown in FIG. 4, all three vaccines were comparably immunogenic at the high dose of $10^9$ vp (A). Importantly, at the lower dose of $10^8$ vp (B), immune responses elicited by recombinant Ad35k5-Gag were significantly more potent than those elicited by recombinant Ad35-Gag ($p<0.01$ comparing mean tetramer responses among groups of mice on day 14 using analyses of variance with Bonferroni adjustments to account for multiple comparisons) and nearly comparable in magnitude to those elicited by Ad5-Gag (p=ns). This is consistent with prior observations (Barouch et al. 2004; Lemckert et al. 2005). These data demonstrate that engineering the Ad35 vector such that it carries the knob domain of a subgroup C adenovirus (e.g., Ad5) provides a substantial improvement of its immunogenicity towards the antigen inserted into the vector.

These experiments were performed in the absence of anti-Ad5 immunity, and it is shown here that Ad5 and Ad35k5 raised comparable immune responses, while these were significantly higher than the Ad35 vector. It is important to note that the Ad35k5 vector carries the Ad35 hexon, which adds to the higher efficacy in raising immune responses in individuals that do harbour neutralizing activity against the hexon protein of Ad5. Thus, the Ad35k5 vector is significantly more efficient in the presence of anti-Ad5 immunity than both Ad5- and Ad35-based vectors; Ad5 is less immunogenic under these conditions because of its native hexon protein, and Ad35 is less immunogenic in general because of its native fiber knob domain.

In cannot be excluded that neutralizing antibodies against the fiber protein may be raised upon infection. However, it is held that under natural conditions such neutralizing activities are minimal, while the major part of the immune response of the host will be against the hexon protein. It is important to note that experiments wherein the recombinant vectors are compared with pre-immunization with parental vectors are to be performed under conditions that mimic the natural (human) situation, wherein wild type viruses infect a natural host once or twice, inducing naturally occurring levels of neutralizing antibodies. In mice in a laboratory setting one can raise extreme immune responses by multifold injections and high titer administrations. Experiments mimicking the natural situation indicate whether neutralizing antibodies that may be directed to the fiber protein indeed are important for neutralizing the administered adenoviral vector. They also reveal the importance of the presence of the shaft region of the fiber, which part is typically also available for neutralizing activities.

We postulate that vectors comprising at least the knob from adenoviruses that recognize and infect host cells via CAR (e.g., Ad2, Ad5, etc), and further comprising a major immunogenic determinant of the capsid (i.e., the hexon protein) from a least neutralized serotype (e.g., Ad11, Ad24, Ad26, Ad34, Ad35, Ad48, Ad49 and Ad50) are excellent vaccination vectors because they combine the hitherto unknown advantages of low vector pre-existing immunity in the human population, high antigenic insert immune response, reproducible production, efficient transduction and good stability.

Example 5

Immunogenicity of Ad5, Ad35k5 and Ad35 in Mice with Pre-Existing Immunity

Figure 4A:
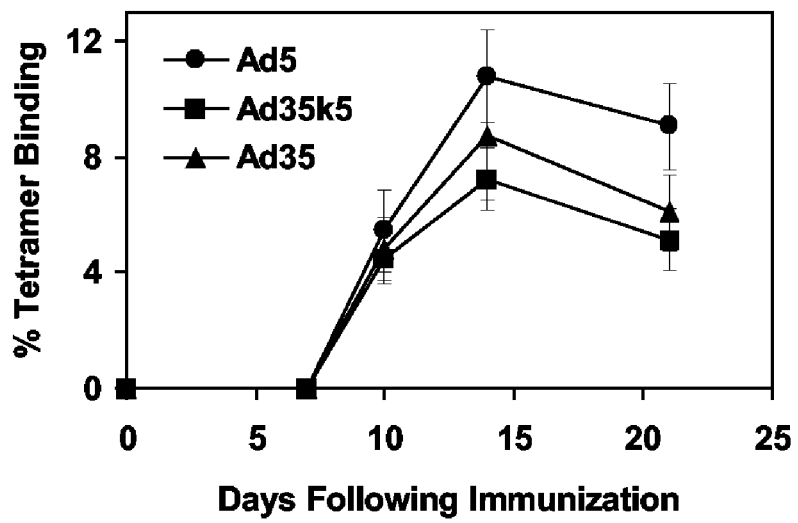
FIG. 4 shows the immunogenicity of Ad5, Ad35k5, and Ad35 vectors expressing SIV Gag in naïve mice, with $10^9$ vp (A) and $10^8$ vp (B), or with pre-immunization with one (C) or two (D) injections of $10^{10}$ vp Ad5-Empty prior to immunization with $10^8$ vp of the respective vectors. In all cases, Gag-specific CD8+ T lymphocyte responses were assessed by $D^b$/AL11 tetramer binding assays at multiple time points following immunization.
Figure 4B:
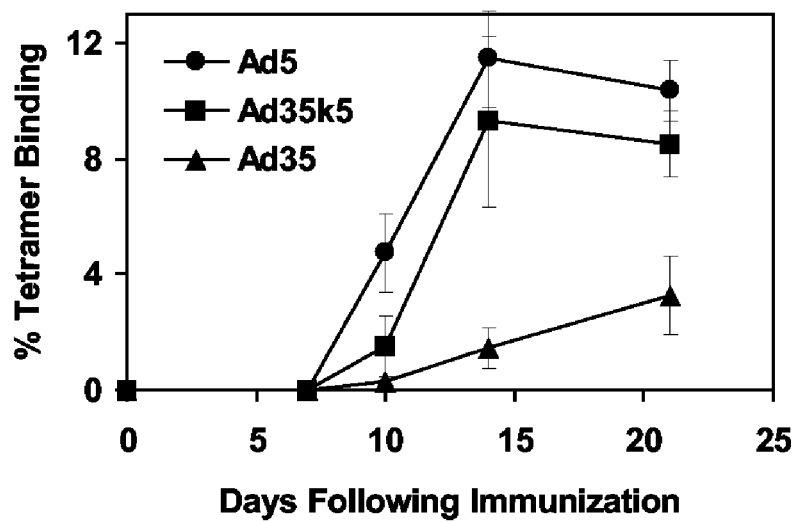
Figure 4C:
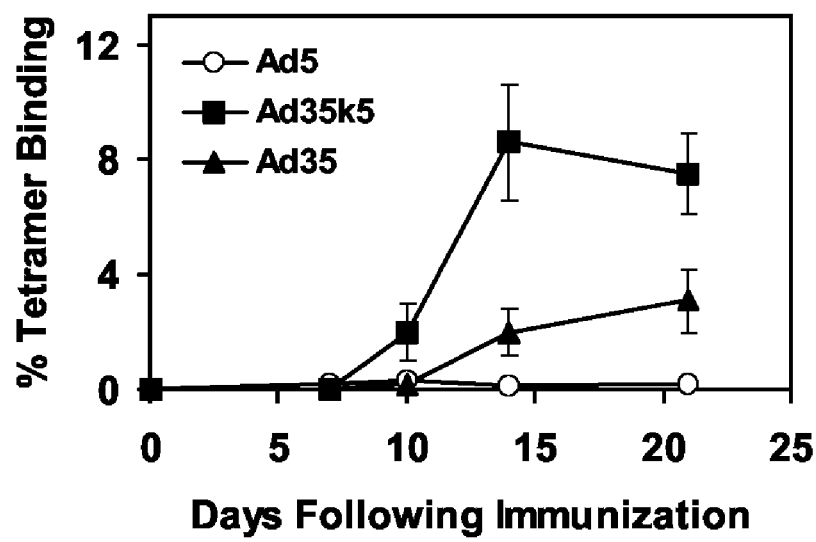

Next, the impact of anti-Ad5 immunity on the immunogenicity of these vectors was evaluated. Groups of C57/BL6 mice (N=4/group) were pre-immunized once with $10^{10}$ vp Ad5-Empty 4 weeks prior to vaccination to generate low/moderate levels of anti-Ad5 immunity. Ad5-specific neutralizing antibody (NAb) titers in these mice were 64-128 (Barouch et al. 2004; Lemckert et al. 2005; Sprangers et al. 2003). As shown in FIG. 4C, tetramer$^+$CD8$^+$ T lymphocyte responses elicited by $10^8$ vp Ad5-Gag were essentially ablated in these mice. In contrast, $10^8$ vp Ad35-Gag and Ad35k5-Gag responses were not substantially affected by this level of anti-Ad5 immunity. Importantly, Ad35k5-Gag proved more immunogenic than both Ad5-Gag ($p<0.001$) and Ad35-Gag ($p<0.05$) in these mice on day 14 following immunization.

Figure 4D:
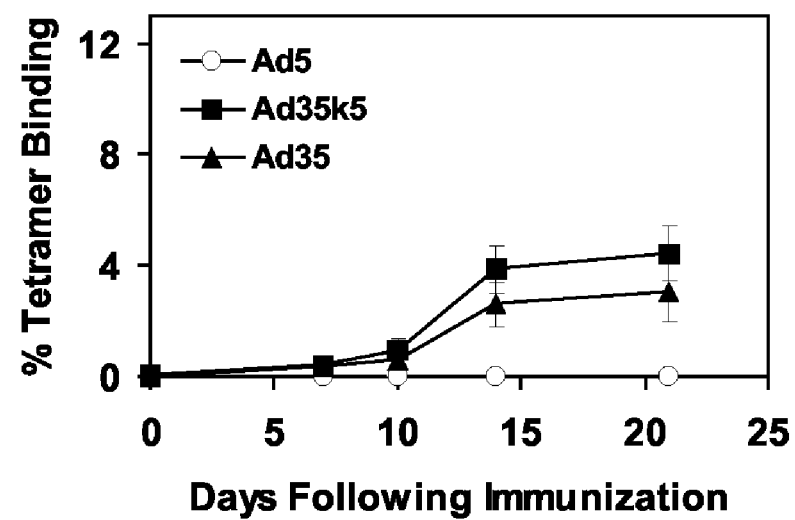

The ability of Ad35k5-Gag to evade low/moderate levels of anti-Ad5 immunity is consistent with the previous findings that Ad5-specific NAbs are directed primarily against the Ad5 hexon protein (see above; Sumida et al. 2005). However, low levels of NAbs directed against the Ad5 fiber protein in this prior study were also detected. This experiment was therefore repeated in mice with high levels of anti-Ad5 immunity. Mice were pre-immunized twice with $10^{10}$ vp Ad5-Empty 8 weeks and 4 weeks prior to vaccination. Ad5-specific NAb titers in these mice were 8,192-16,384 (Barouch et al. 2004; Lemckert et al. 2005; Sprangers et al. 2003), comparable with the highest titers found in individuals in sub-Saharan Africa (Kostense et al. 2004; Sumida et al. 2005). As shown in FIG. 4D, tetramer$^+$CD8$^+$ T lymphocyte responses elicited by Ad35k5-Gag were partially reduced in these mice and were comparable with those induced by Ad35-Gag (p=ns). Thus, high levels of anti-Ad5 immunity partially suppressed the immunogenicity of Ad35k5 vectors.

Figure 5A:
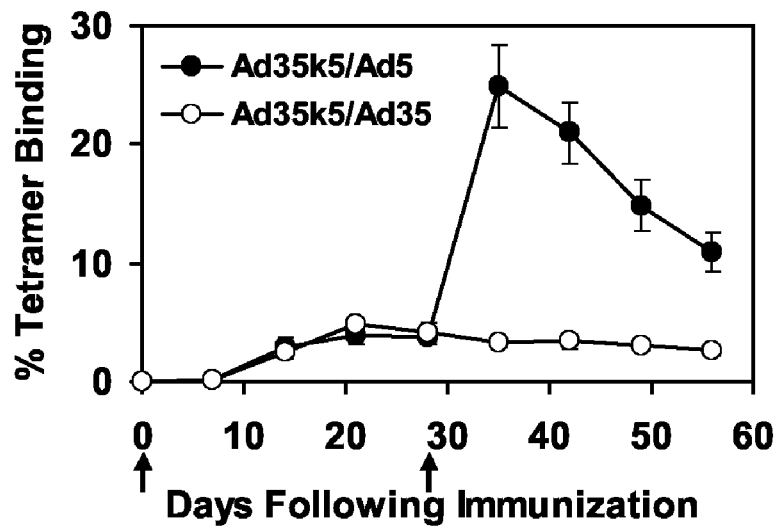
FIG. 5 shows the anti-vector immunity elicited by Ad35k5 vectors in mice. (A) Naïve C57/BL6 mice primed at week 0 with $10^9$ vp Ad35k5-Gag and boosted at week 4 with $10^9$ vp Ad5-Gag or Ad35-Gag. (B) Serum samples from mice injected with $10^9$ vp Ad5-Gag, Ad35k5-Gag, or Ad35-Gag assessed in Ad5 and Ad35 luciferase-based virus neutralization assays.
Figure 5B:
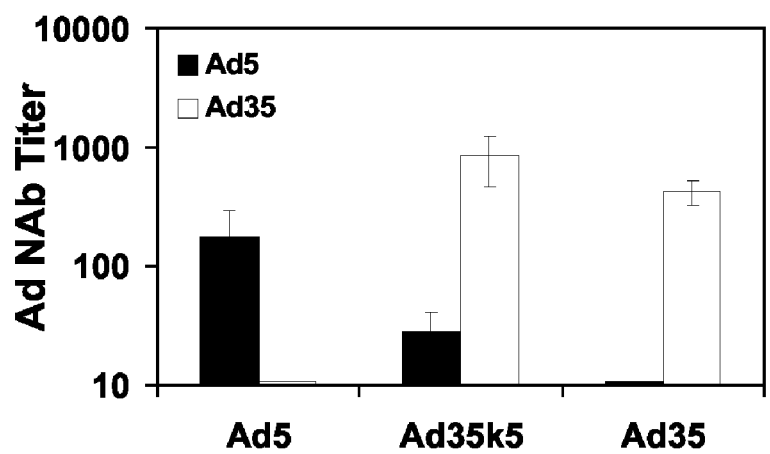

To evaluate in further detail vector-specific immunity elicited by the chimeric Ad35k5-Gag vectors, heterologous prime-boost studies as well as virus neutralization assays were performed. Groups of naïve C57/BL6 mice (N=4/group) were primed at week 0 with $10^9$ vp Ad35k5-Gag and then boosted at week 4 with $10^9$ vp Ad5-Gag or Ad35-Gag. As shown in FIG. 5A, tetramer$^+$CD8$^+$ T lymphocyte responses elicited by Ad35k5-Gag were efficiently boosted by Ad5-Gag but not by Ad35-Gag. These data suggest that Ad35 and Ad35k5 induced substantial cross-reactive anti-vector immunity, whereas Ad5 and Ad35k5 were largely immunologically distinct. Consistent with these observations, mice immunized once with Ad35k5-Gag generated Ad35-specific NAbs comparable with those induced by Ad35-Gag but substantially lower Ad5-specific NAbs (FIG. 5B). Thus, Ad35k5 vectors exhibited serologic profiles more similar to Ad35 vectors than Ad5 vectors.

Figure 6A:
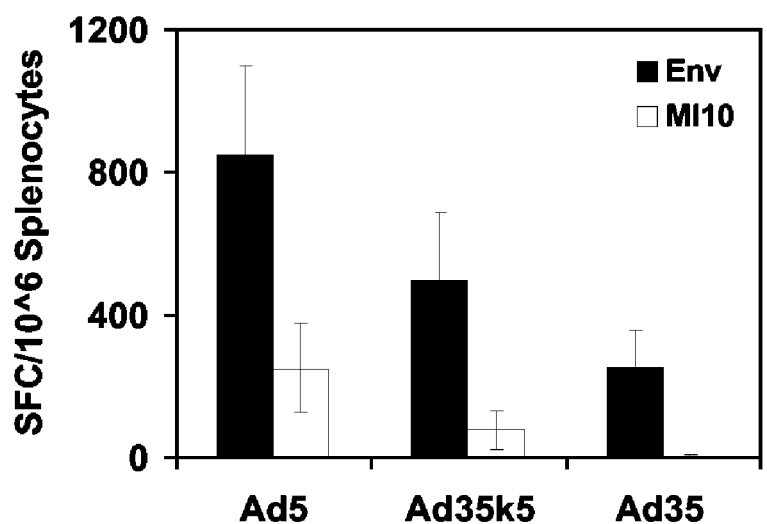
FIG. 6 shows the immunogenicity of Ad5, Ad35k5, and Ad35 vectors expressing HIV-1 Env in mice. Naïve Balb/c mice were immunized with $10^8$ vp Ad5-Env, Ad35k5-Env, or Ad35-Env. (A) Env-specific cellular immune responses assessed by pooled peptide and MI10 epitope peptide-specific IFN-γ ELISPOT assays. (B) Env-specific humoral immune responses assessed by ELISA.
Figure 6B:
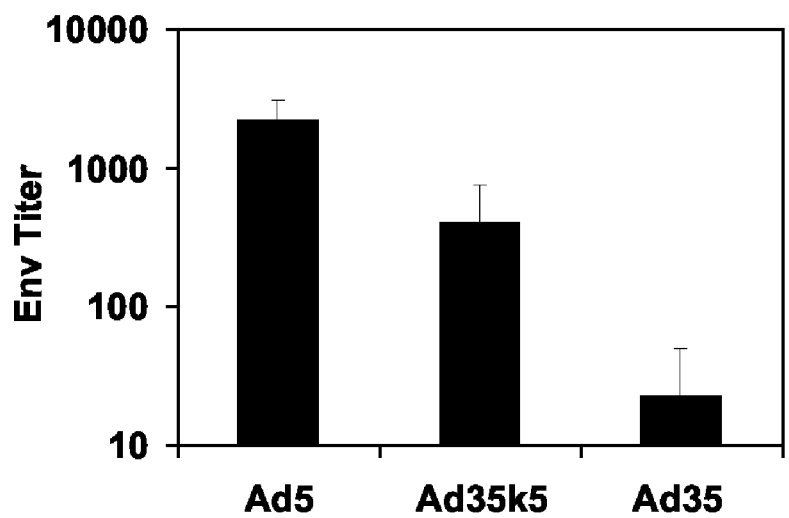

To assess the generalizability of these results, the immunogenicity of Ad35k5 vectors expressing another antigen (Env: HIV-1 89.6P Env gp120, for cloning details, see herein and Vogels et al. 2003) in a different strain of mice was evaluated. Groups of naïve Balb/c mice (N=4/group) were immunized once intramuscularly with $10^9$ vp Ad5-Env, Ad35k5-Env, or Ad35-Env. Cellular and humoral immune responses elicited by Ad35k5-Env vectors were intermediate between those induced by Ad5-Env vectors and Ad35-Env vectors, as measured by IFN-γ ELISPOT assays (FIG. 6A) and Env-specific ELISA's (FIG. 6B).

The ELISA's were performed as follows. Serum antibody titers from immunized mice specific for HIV-1 Env or SIV Gag were measured by a direct ELISA as described (Barouch et al. 2003; Sumida et al. 2005). 96-well plates coated overnight with 100 μl/well of 1 μg/ml recombinant HIV-1 MN Env gp120 or SIVmac239 Gag p27 polypeptide (ImmunoDiagnostics) in PBS, were blocked for 2 h with PBS containing 2% BSA and 0.05% Tween-20. Sera were then added in serial dilutions and incubated for 1 h. The plates were washed three times with PBS containing 0.05% Tween-20 and incubated for 1 h with a 1:2000 dilution of a peroxidase-conjugated affinity-purified rabbit anti-mouse secondary antibody (Jackson Laboratories, USA). The plates were washed three times, developed with tetramethylbenzidine, stopped with 1% HCl, and analyzed at 450 nm with a Dynatech MR5000 ELISA plate reader.

Example 6

Immunogenicity of Ad5, Ad35k5 and Ad35 Vectors in Rhesus Monkeys

To confirm the immunogenicity studies in mice, a pilot study to evaluate the immunogenicity of these vectors in rhesus monkeys was performed. Nine Mamu-A*01-negative rhesus monkeys (N=3/group) were immunized intramuscularly with $10^{11}$ vp Ad5, Ad35 or Ad35k5 vectors expressing SIV Gag and HIV-1 Env. Monkeys were primed at week 0 and received a homologous boost immunization at week 12. FIG. 7 depicts antigen- and vector-specific immune responses in these animals. Gag- and Env-specific cellular immune responses were quantified by pooled peptide IFN-γ ELISPOT assays, and vector-specific NAb titers were determined by the luciferase-based virus neutralization assays at multiple time points following immunization. The neutralization assay was performed as described above.

The Ad5 vectors elicited high frequency ELISPOT responses following the primary immunization as expected (mean Gag+Env responses of 538 SFC/$10^6$ PBMC at week 12), but these responses were not substantially increased following the homologous boost immunization (mean 608 SFC/$10^6$ PBMC at week 16; FIG. 7A), presumably reflecting the rapid generation of high titers of Ad5-specific NAbs in these animals (FIG. 7B). In contrast, the Ad35 vectors elicited antigen-specific ELISPOT responses that were approximately 2-fold lower than those induced by the Ad5 vectors following the initial immunization (mean 248 SFC/$10^6$ PBMC at week 12). Interestingly, these responses increased substantially following the homologous boost immunization (mean 876 SFC/$10^6$ PBMC at week 16; FIG. 7C), consistent with the lower titers of vector-specific NAbs initially generated in these animals (FIG. 7D). These data suggest that Ad35 vectors elicited both lower antigen-specific immune responses as well as lower vector-specific immune responses as compared with Ad5 vectors in rhesus monkeys.

Figure 8A:
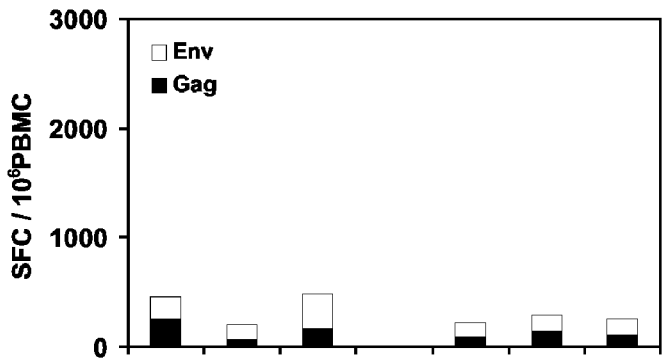
FIG. 8 shows the CD4$^+$ and CD8$^+$ T lymphocyte responses in monkeys in the study described in FIG. 7. Pooled peptide IFN-γ ELISPOT assays were performed using CD8-depleted and CD4-depleted PBMC's from monkeys at week 16 following immunization. Monkeys received $10^{11}$ vp (A) Ad5-Gag, (B) Ad35-Gag, or (C) Ad35k5-Gag at week 0 and week 12.
Figure 8B:
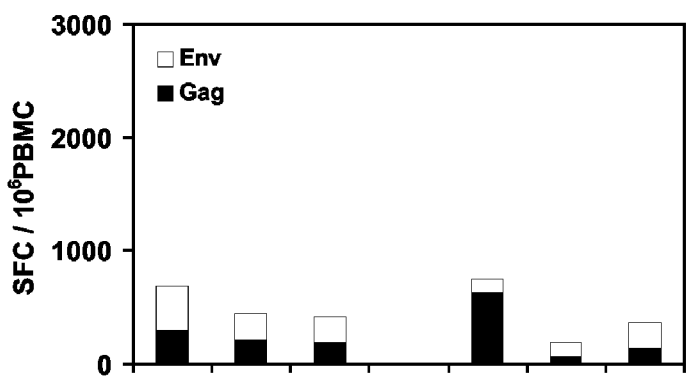
Figure 8C:
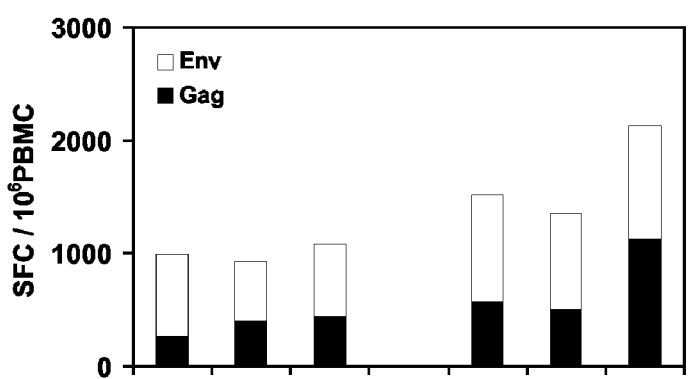

The Ad35k5 vectors elicited antigen-specific ELISPOT responses comparable with those induced by the Ad5 vectors following the primary immunization (mean 578 SFC/$10^6$ PBMC at week 12; FIG. 7E). Importantly, these responses were substantially enhanced following the homologous boost immunization (mean 1736 SFC/$10^6$ PBMC at week 16), presumably reflecting the relatively low vector-specific NAbs initially generated in these monkeys (FIG. 7F). In fact, following the boost immunization, the Ad35k5 vectors elicited 2-3 fold higher Gag- and Env-specific ELISPOT responses than both the Ad5 and Ad35 vectors. Moreover, the Ad35k5 vectors elicited potent fractionated CD4+ and CD8+ T lymphocyte responses at week 16 following immunization as determined by ELISPOT assays using CD8-depleted and CD4-depleted PBMCs (FIGS. 8A, B, C: Ad5, Ad35, Ad35k5 respectively).

Example 7

Generation of Recombinant Ad5 Vectors Containing Chimeric Hexon Proteins

The HVR's of Ad2 according to Crawford-Miksza and Schnurr (1996), of Ad5 according to Rux and Burnett (2000), of Ad5 according to Rux et al. (2003) and of Ad5 according to the present invention are depicted in table I. Table II provides the seven HVR sequences of human adenoviruses Ad5, Ad11, Ad26, Ad35, and Ad48, and chimpanzee adenovirus 68 (Pan9) according to the HVR definition of the present invention. Specific positions within the respective hexon sequences are also depicted.

Ad5-based vectors containing one or more HVR's, exchanged from Ad35 (subgroup B) or Ad48 (subgroup D) were constructed.

In a more 'minimalistic' embodiment of the present invention, the HVR's of the above mentioned adenovirus serotypes are defined in a somewhat shortened fashion. These HVR's are depicted with an asterisk in Table IV as HVR(1-7)*. Using the minimalistic definition in recombinant vectors, HVR1* is deleted from the backbone, HVR2* is replaced with a short two-amino acid spacer (QG), whereas HVR3*, HVR4*, HVR5*, HVR6*, and HVR7* are replaced by their respective shorter (*) counterparts from the other serotypes. Most significantly, HVR7 is redefined much narrower (compare Table II and Table IV).

Partial hexon genes containing the desired sequences were synthesized by GeneArt (Germany) and cloned as ApaI-HpaI fragments into a shuttle plasmid containing the complete Ad5 hexon gene. A larger AscI-AscI fragment was then excised from this shuttle plasmid and utilized to replace the corresponding AscI-AscI fragment in the Ad5 cosmid pWE.Ad5.AflII-rITR.dE3 (vector carrying a deletion of the E3 region and based on cosmid pWE.Ad5.AflII-rITR, see WO 02/40665). The mutant Ad5 cosmids together with the adaptor plasmid pAdApt-Gag (encoding the gag protein of Simian Immunodeficiency Virus (SIV)) were then co-transfected into PER.C6/55K cells (harbouring the 55K E1B gene from Ad35 in PER.C6® cells, see WO 02/40665), and homologous recombination yielded recombinant Ad5HVR35(1)-Gag, recombinant Ad5HVR48(1)-Gag and recombinant Ad5HVR48(1-7)-Gag viruses, wherein the '1' indicates the replacement of only HVR1 and wherein '1-7' indicates the replacement of all seven separate HVR's. These vectors were plaque-purified, sequenced, expanded, and purified by CsCl gradient centrifugation according to general procedures known in the art. The sequence of the hexon in Ad5HVR48(1-7)-Gag is given in FIG. 11.

Besides the three viruses mentioned above, the following recombinant vectors are also made: Ad5HVR35(1-6), Ad5HVR35(1-7) (FIG. 12), Ad5HVR11(1-6), Ad5HVR11(1-7) (FIG. 13), Ad5HVR26(1-6), Ad5HVR26(1-7) (FIG. 14), Ad5HVRPan9(1-6) and Ad5HVRPan9(1-7) (FIG. 15). '1-6' indicates the replacement of HVR1-HVR6, leaving HVR7 of the parent vector. Clearly, based on the several parental vectors available (such as Ad2 and Ad5) and the several known rare serotypes, more combinations are possible to create, using the teaching of the present invention. Other rare human adenovirus serotypes that may be used to provide HVR's to produce 'stealth'-like vectors are Ad24, Ad34, Ad49 and Ad50.

Example 8

Immunogenicity of Ad5, Ad5HVR48(1) and Ad5HVR48(1-7) Viruses in Naïve Mice and in Mice with Anti-Ad5 Immunity As outlined above, viable recombinant Ad5-Gag, Ad5HVR48(1)-Gag and Ad5HVR48(1-7)-Gag viruses were produced on packaging cells. The yield of Ad5HVR48(1)-Gag was comparable to the recombinant Ad5-Gag virus, whereas the growth rate, yield and vp/pfu ratio of Ad5HVR48 (1-7)-Gag virus was approximately 2-fold lower than the Ad5-Gag virus. The Gag expression was first checked on A549 cells infected with $10^9$ or $10^{10}$ vp of each vector. HPLC data indicated that intracellular Gag expression was sufficient and comparable between the different vectors (data not shown), although the expression from Ad5HVR48(1-7)-Gag was somewhat lower than from Ad5-Gag. This could be related to the somewhat slower growth-rate.

Figure 9A:
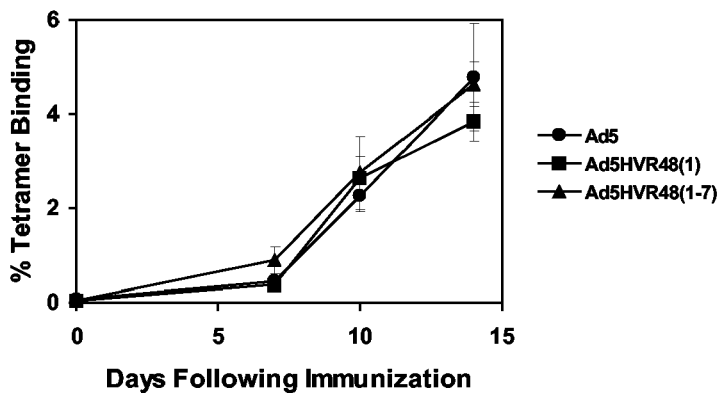
FIG. 9 shows the immunogenicity of Ad5-Gag, Ad5HVR48(1)-Gag and Ad5HVR48(1-7) vectors in naïve mice receiving (A) $10^9$ vp, (B) $10^8$ vp, or (C) $10^7$ vp. Gag-specific CD8$^+$ T lymphocyte responses were assessed by $D^b$/AL11 tetramer binding assays at multiple time points following immunization.
Figure 9B:
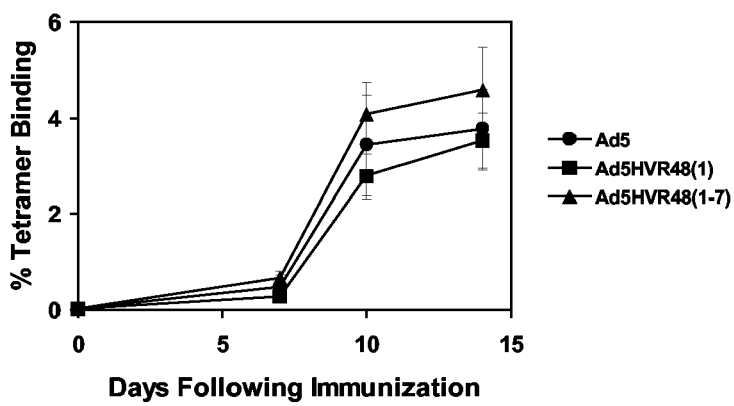
Figure 9C:
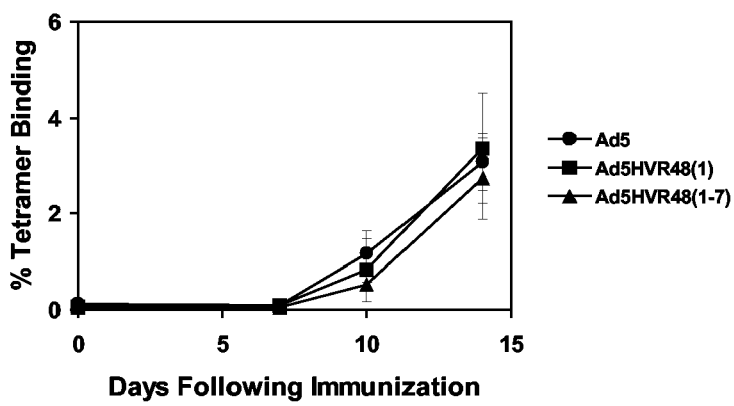

The immunogenicity of the viruses was first investigated by immunizing naïve C57/BL6 mice (4 mice per group) with $10^9$, $10^8$ and $10^7$ vp of each vector. The vaccine-elicited CD8+ T lymphocyte responses were assessed by $D^b$/AL11 tetramer binding assays as described above for two weeks. The results are shown in FIG. 9. Clearly, all three vectors resulted in comparable immune responses in these naïve mice, despite the small differences in growth rate and transgene expression.

Figure 10A:
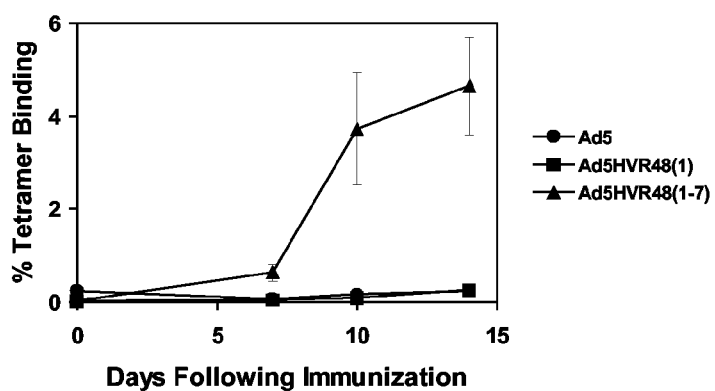
FIG. 10 shows the immunogenicity of Ad5-Gag, Ad5HVR48(1)-Gag and Ad5HVR48(1-7) vectors in mice receiving (A) $10^9$ vp, (B) $10^8$ vp, or (C) $10^7$ vp, pre-immunized with two injections of $10^{10}$ vp Ad5-Empty 8 and 4 weeks prior to immunization.
Figure 10B:
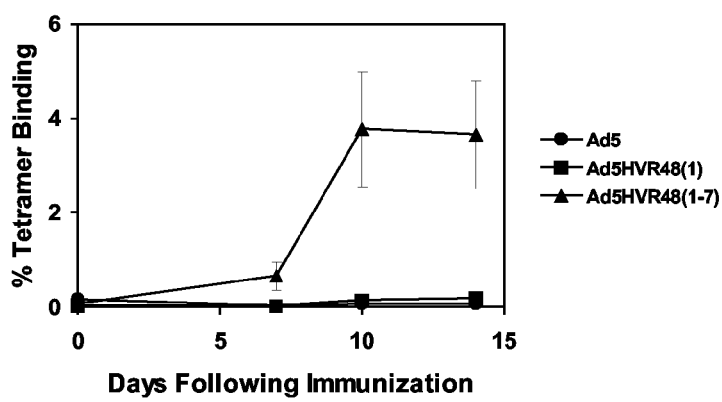
Figure 10C:
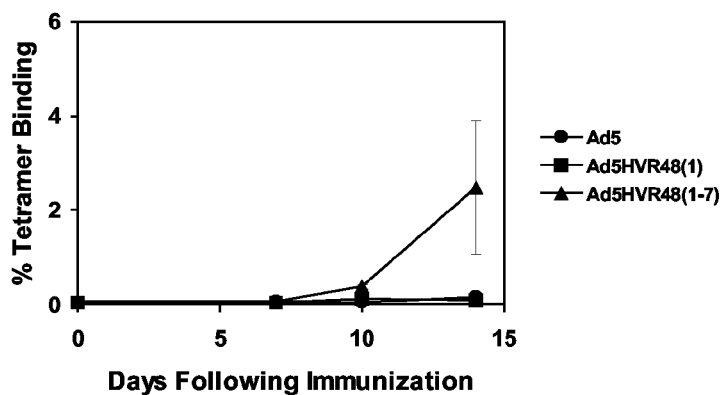

Subsequently, C57/BL6 mice were pre-immunized with 2 injections of $10^{10}$ vp Ad5-empty, respectively 8 and 4 weeks prior to immunization with the viruses of interest (Ad5 Nab titers 8, 192-16, 384) to yield a pre-existing immunity against the Ad5 base vector. Then (at 8 weeks from the first pre-immunization) the mice were immunized as above with $10^9$, $10^8$, and $10^7$ vp of recombinant Ad5-Gag, Ad5HVR48(1)-Gag and Ad5HVR48(1-7)-Gag. Again, the vaccine-elicited CD8+ T lymphocyte responses were assessed by $D^b$/AL11 tetramer binding assays as described above, for two weeks. The results are shown in FIG. 10. ELISPOT results mirrored the tetramer assays and provided similar results (data not shown).

Figure 21:
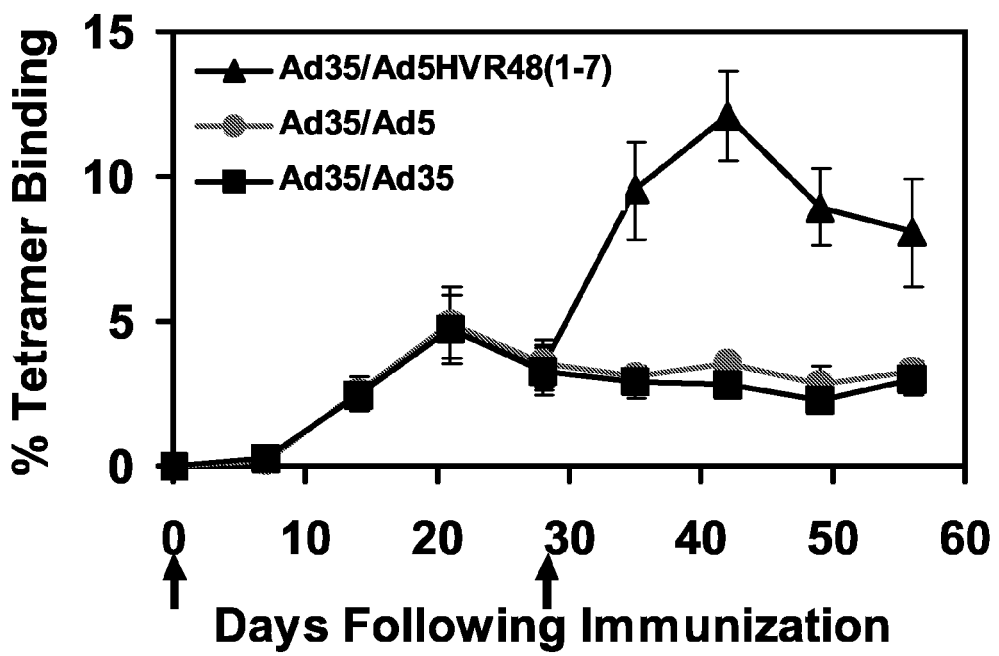
FIG. 21 is a graph indicating the CD8+ T-lymphocyte response in mice after a double pre-immunization with Ad5-empty, followed by a priming on day 0 with Ad35-Gag and a boost on day 28 with three different vectors as indicated.

As expected the Ad5-Gag vector encountered pre-existing immunity in these pre-immunized mice which resulted in an hardly detectable immune response. The Ad5HVR48(1)-Gag virus also failed to circumvent the high levels of anti-Ad5 immunity, suggesting that pre-existing immunity is at least not limited to HVR1 alone. Importantly, the immunogenicity of the Ad5HVR48(1-7)-Gag virus was not influenced by the Ad5-induced pre-existing immunity, indicating that by mutating the 7 hexon HVR's (as identified herein) of Ad5 and replacing them with the corresponding HVR's of a rare serotype (exemplified by Ad48) results in a vector that is not hampered by pre-existing immunity against the wild type protein. Similar results were obtained in experiments wherein mice were primed twice with an empty Ad5 vector, representing a situation with high levels of pre-existing immunity (FIG. 21). This experiment was done with 4 C57/BL6 mice per group. Groups of mice were pre-immunized with two injections of $10^{10}$ vp Ad5-empty to induce anti-Ad5 immunity. Mice that were pre-immunized with Ad5-empty had Ad5 NAb titres of 8,192-16,384. Mice were then primed on day 0 intramuscularly with $10^9$ vp Ad35-Gag and then boosted on day 28 with either $10^9$ vp Ad5-Gag, $10^9$ vp Ad35-Gag, or $10^9$ vp Ad5HVR48(1-7)-Gag. All injections utilized a volume of 50 μl. The arrows on the x-axis indicate immunizations. Blood samples were obtained at days 0, 7, 14, 21, 28, 35, 42, 49, 56 for $D^b$/AL11 tetramer staining assays to quantitate vaccine-elicited CD8+ T lymphocyte responses. At day 56, IFN-gamma ELISPOT assays were also performed and showed comparable results (data not shown). Ad5-Gag failed to boost, presumably due to the pre-existing anti-Ad5 immunity. Also Ad35-Gag failed to boost, presumably due to the anti-Ad35 immunity induced by the priming immunization. Ad5HVR48(1-7) effectively boosted the responses, confirming that this vector functions as some sort of novel 'serotype'. It is concluded that Ad5HVR48(1-7) thus can serve as an effective boosting vector in settings where Ad5 fails, and in settings where a heterologous vector (such as Ad35) is used as a prime vector. Combined with the prior studies in the presentation, we conclude overall that vectors as represented by Ad5HVR48(1-7) are both effective priming vectors and effective boosting vectors in settings of pre-existing anti-Ad5 immunity where Ad5 fails.

These results now enable one to use Ad5-based vectors in prime-boost settings, while the receptor recognition (mainly brought about by fiber and penton proteins) remains unchanged.

TABLE I

Hyper-variable region definitions within the hexon protein of human adenoviruses Ad2 (according to Crawford-Miksza and Schnurr, 1996), Ad5 (according to Rux and Burnett, 2000); Rux et al. 2003) and Ad5 (according to the present invention). The HVR definitions of Ad5 of Rux and Burnett (2000) correspond exactly to the Crawford-Miksza definitions based on the Ad2 sequence. Note that these HVR definitions are all changed by 1 position in this table due to the absence of the initial Methionine residue in the Rux and Burnett (2000) definitions (HVR1: 137-181, etc.).

|  | Crawford-Miksza (1996) Ad2 | Rux (2000) Ad5 | Rux (2003) Master | Rux (2003) Ad5 | Present invention Ad5 |
|---|---|---|---|---|---|
| HVR1 | 137-188 | 138-182 | 146-181 | 139-167 | 136-165 |
| HVR2 | 194-204 | 188-194 | 199-221 | 184-198 | 188-194 |
| HVR3 | 222-229 | 212-219 | 264-270 | none | 212-220 |
| HVR4 | 258-271 | 248-261 | 288-293 | 254-258 | 248-258 |
| HVR5 | 278-294 | 268-283 | 307-330 | 272-280 | 268-281 |
| HVR6 | 316-327 | 305-316 | 358-366 | 308 | 305-310 |
| HVR7 | 433-465 | 422-450 | 482-489 | 420-422 | 418-451 |
| HVR8 |  |  | 503-513 | 435-440 |  |
| HVR9 |  |  | 518-522 | 445-446 |  |

TABLE II

```
Position  Sequence

Ad5

HVR1  136-165  DEAATALEINLEEEDDDNEDEVDEQAEQQK      SEQ ID NO:17
HVR2  188-194  VEGQTPK                             SEQ ID NO:18
HVR3  212-220  YETEINHAA                           SEQ ID NO:19
HVR4  248-258  GILVKQQNGKL                         SEQ ID NO:20
HVR5  268-281  STTEATAGNGDNLT                      SEQ ID NO:21
HVR6  305-310  TIKEGN                              SEQ ID NO:22
HVR7  418-451  GGVINTETLTKVKPKTGQENGWEKDATEFSDKNE  SEQ ID NO:23

Ad48

HVR1  136-150  EEKNGGGSDANQMQ                      SEQ ID NO:24
HVR2  173-185  IDATKEEDNGKEI                       SEQ ID NO:25
HVR3  203-210  QDSDNYYG                            SEQ ID NO:26
HVR4  238-251  AKFKTPEKEGEEPK                      SEQ ID NO:27
HVR5  261-277  DIPSTGTGGNGTNVNFK                   SEQ ID NO:28
HVR6  301-306  GKEDAS                              SEQ ID NO:29
HVR7  414-446  DGAGTNAVYQGVKVKTTNNTEWEKDTAVSEHNQ   SEQ ID NO:30

Ad35

HVR1  136-160  IAKGVPTAAAAGNGEEEHETEEKTA           SEQ ID NO:31
HVR2  164-175  LEISAENESKPI                        SEQ ID NO:32
HVR3  193-203  TDLDGKTEEYG                         SEQ ID NO:33
HVR4  231-243  AKPKNSEPSSEKI                       SEQ ID NO:34
HVR5  253-262  DNSSQRTNFS                          SEQ ID NO:35
HVR6  286-291  GTEDTS                              SEQ ID NO:36
HVR7  399-431  DGIGVPTTSYKSIVPNGEDNNNWKEPEVNGTSE   SEQ ID NO:37

Ad11

HVR1  136-157  IAEGVKNTTGEEHVTEEETNTT              SEQ ID NO:38
HVR2  181-191  LEVSDEESKPI                         SEQ ID NO:39
HVR3  209-219  TDLDGKTEKYG                         SEQ ID NO:40
HVR4  247-259  AKQKTTEQPNQKV                       SEQ ID NO:41
HVR5  269-278  DAASQKTNLS                          SEQ ID NO:42
HVR6  302-307  GTEDTS                              SEQ ID NO:43
HVR7  415-447  DGIGVPTTSYKSIVPNGDNAPNWKEPEVNGTSE   SEQ ID NO:44
```

TABLE II-continued

Position Sequence

Ad26

| | | | |
|---|---|---|---|
| HVR1 | 146-163 | ETKEKQGTTGGVQQEKDV | SEQ ID NO:45 |
| HVR2 | 186-197 | TDETAENGKKDI | SEQ ID NO:46 |
| HVR3 | 215-222 | QENEAFYG | SEQ ID NO:47 |
| HVR4 | 250-262 | AKFKPVNEGEQPK | SEQ ID NO:48 |
| HVR5 | 272-288 | DVPGGSPPAGGSGEEYK | SEQ ID NO:49 |
| HVR6 | 312-317 | GTSDNS | SEQ ID NO:50 |
| HVR7 | 425-461 | NGTGTNSTYQGVKITNGNDGAEESEWEKDDAISRQNQ | SEQ ID NO:51 | pan9

| | | | |
|---|---|---|---|
| HVR1 | 136-147 | TYKADGETATEK | SEQ ID NO:52 |
| HVR2 | 170-177 | TDTDDQPI | SEQ ID NO:53 |
| HVR3 | 195-205 | HDITGTDEKYG | SEQ ID NO:54 |
| HVR4 | 233-243 | ANVKTGTGTTK | SEQ ID NO:55 |
| HVR5 | 253-263 | DNRSAAAAGLA | SEQ ID NO:56 |
| HVR6 | 287-292 | GTDDSS | SEQ ID NO:57 |
| HVR7 | 400-432 | DAVGRTDTYQGIKANGTDQTTWTKDDSVNDANE | SEQ ID NO:58 |

Ad34

| | | | |
|---|---|---|---|
| HVR1 | 136-160 | LDKGVTSTGLVDDGNTDDGEEAKKA | SEQ ID NO:59 |
| HVR2 | 184-194 | LEVSTEGPKPI | SEQ ID NO:60 |
| HVR3 | 212-222 | TDLDGKTEEYG | SEQ ID NO:61 |
| HVR4 | 250-263 | AKVKPKEDDGTNNI | SEQ ID NO:62 |
| HVR5 | 273-282 | DLRSQRSELK | SEQ ID NO:63 |
| HVR6 | 306-311 | GVSDAS | SEQ ID NO:64 |
| HVR7 | 419-450 | DGVGPRTDSYKEIKPNGDQSTWTNVDPTGSSE | SEQ ID NO:65 |

Ad49

| | | | |
|---|---|---|---|
| HVR1 | 136-147 | DAKENNGQGEAK | SEQ ID NO:66 |
| HVR2 | 170-183 | IDENKEEDEEGREI | SEQ ID NO:67 |
| HVR3 | 201-208 | QNTENFYG | SEQ ID NO:68 |
| HVR4 | 236-248 | AVFKTGENGKPTE | SEQ ID NO:69 |
| HVR5 | 258-270 | DLRQNDTGGNNNQ | SEQ ID NO:70 |
| HVR6 | 294-299 | GTSDDS | SEQ ID NO:71 |
| HVR7 | 407-442 | DGSGSSTAYQGVEPDTTVAGTNDKWKVNAKVAQHNQ | SEQ ID NO:72 |

Ad50

| | | | |
|---|---|---|---|
| HVR1 | 136-150 | LNKGDEEDGEDDQQA | SEQ ID NO:73 |
| HVR2 | 174-185 | LEVPSEGGPKPI | SEQ ID NO:74 |
| HVR3 | 203-213 | TDTDGTDEKYG | SEQ ID NO:75 |
| HVR4 | 241-251 | AKVKKEEEGKV | SEQ ID NO:76 |
| HVR5 | 261-270 | DLRSQMTGLK | SEQ ID NO:77 |
| HVR6 | 294-299 | GASDAS | SEQ ID NO:78 |
| HVR7 | 407-439 | DGVGPRIDSYKGIETNGDETTTWKDLEPKGISE | SEQ ID NO:79 |

TABLE III

The chimeric replication-defective adenovirus vector according to the present invention, including the identification of the different elements within said vector.

| Part of the chimeric adenovirus/vector | Characterising feature |
|---|---|
| Backbone serotype X (Elements of the vector not complemented by packaging cell and excluding the fiber and hexon protein, including the penton protein) | Wherein X is selected from the group consisting of the adenoviruses applicable for human treatment (including human adenovirus serotypes 1-51, chimpanzee-, bovine- and canine adenoviruses) |
| Hexon HVR(n) Y | Wherein Y is selected from the group consisting of human adenovirus serotypes 11, 24, 26, 34, 35, 48, 49 and 50, and wherein n = 0-7, provided that if X ≠ Y, n = 1-7. |
| Fiber delta knob F, comprising tail T and shaft S | Wherein F is selected from the group consisting of serotypes 1-51, chimp, . . . provided that if F ≠ X, at least the part of T of F that interacts with penton is X |

TABLE III-continued

The chimeric replication-defective adenovirus vector according to the present invention, including the identification of the different elements within said vector.

| Part of the chimeric adenovirus/vector | Characterising feature |
|---|---|
| Knob K | Wherein K is selected from the group consisting of adenovirus serotypes that primarily use the CAR receptor on a cell for infection (human adenovirus serotypes from subgroup A, C, D, E and F) and K may be X or different. |

TABLE IV

|  | Position | Sequence |  |
|---|---|---|---|
| Ad5 | | | |
| HVR1* | 137-165 | EAATALEINLEEEDDDNEDEVDEQAEQQK | SEQ ID NO:88 |
| HVR2* | 188-193 | VEGQTP | SEQ ID NO:89 |
| HVR3* | 213-215 | ETE | SEQ ID NO:90 |
| HVR4* | 252-258 | KQQNGKL | SEQ ID NO:91 |
| HVR5* | 269-281 | TTEATAGNGDNLT | SEQ ID NO:92 |
| HVR6* | 306-308 | IKE | SEQ ID NO:93 |
| HVR7* | 432-445 | KTGQENGWEKDATE | SEQ ID NO:94 |
| Ad48 | | | |
| HVR1* | 137-150 | EKKNGGGSDANQMQ | SEQ ID NO:95 |
| HVR2* | 173-184 | IDATKEEDNGKE | SEQ ID NO:96 |
| HVR3* | 204-206 | DSD | SEQ ID NO:97 |
| HVR4* | 241-251 | KTPEKEGEEPK | SEQ ID NO:98 |
| HVR5* | 262-277 | IPSTGTGGNGTNVNFK | SEQ ID NO:99 |
| HVR6* | 302-304 | KED | SEQ ID NO:100 |
| HVR7* | 428-440 | KTTNNTEWEKDTA | SEQ ID NO:101 |
| Ad35 | | | |
| HVR1* | 137-160 | AKGVPTAAAAGNGEEEHETEEKTA | SEQ ID NO:102 |
| HVR2* | 164-174 | LEISAENESKP | SEQ ID NO:103 |
| HVR3* | 194-196 | DLD | SEQ ID NO:104 |
| HVR4* | 234-243 | KNSEPSSEKI | SEQ ID NO:105 |
| HVR5* | 254-262 | NSSQRTNFS | SEQ ID NO:106 |
| HVR6* | 287-289 | TED | SEQ ID NO:107 |
| HVR7* | 414-425 | NGEDNNNWKEPE | SEQ ID NO:108 |
| Ad11 | | | |
| HVR1* | 137-157 | AEGVKNTTGEEHVTEEETNTT | SEQ ID NO:109 |
| HVR2* | 181-190 | LEVSDEESKP | SEQ ID NO:110 |
| HVR3* | 210-212 | DLD | SEQ ID NO:111 |
| HVR4* | 250-259 | KTTEQPNQKV | SEQ ID NO:112 |
| HVR5* | 270-278 | AASQKTNLS | SEQ ID NO:113 |
| HVR6* | 303-305 | TED | SEQ ID NO:114 |
| HVR7* | 430-441 | NGDNAPNWKEPE | SEQ ID NO:115 |
| Ad26 | | | |
| HVR1* | 147-163 | TKEKQGTTGGVQQEKDV | SEQ ID NO:116 |
| HVR2* | 186-196 | TDETAENGKKD | SEQ ID NO:117 |
| HVR3* | 216-218 | ENE | SEQ ID NO:118 |
| HVR4* | 253-262 | KPVNEGEQPK | SEQ ID NO:119 |
| HVR5* | 273-288 | VPGGSPPAGGSGEEYK | SEQ ID NO:120 |
| HVR6* | 313-315 | TSD | SEQ ID NO:121 |
| HVR7* | 439-455 | TNGNDGAEESEWEKDDA | SEQ ID NO:122 |
| pan9 | | | |
| HVR1* | 137-147 | YKADGETATEK | SEQ ID NO:123 |
| HVR2* | 170-176 | TDTDDQP | SEQ ID NO:124 |
| HVR3* | 196-198 | DIT | SEQ ID NO:125 |
| HVR4* | 236-243 | KTGTGTTK | SEQ ID NO:126 |
| HVR5* | 254-263 | NRSAAAAGLA | SEQ ID NO:127 |

TABLE IV-continued

| | Position | Sequence | |
|---|---|---|---|
| HVR6* | 288-290 | TDD | SEQ ID NO:128 |
| HVR7* | 414-426 | NGTDQTTWTKDDS | SEQ ID NO:129 |
| Ad34 | | | |
| HVR1* | 137-160 | DKGVTSTGLVDDGNTDDGEEAKKA | SEQ ID NO:130 |
| HVR2* | 184-193 | LEVSTEGPKP | SEQ ID NO:131 |
| HVR3* | 213-215 | DLD | SEQ ID NO:132 |
| HVR4* | 253-263 | KPKEDDGTNNI | SEQ ID NO:133 |
| HVR5* | 274-282 | LRSQRSELK | SEQ ID NO:134 |
| HVR6* | 307-309 | VSD | SEQ ID NO:135 |
| HVR7* | 434-444 | NGDQSTWTNVD | SEQ ID NO:136 |
| Ad49 | | | |
| HVR1* | 137-147 | AKENNGQGEAK | SEQ ID NO:137 |
| HVR2* | 170-182 | IDENKEEDEEGRE | SEQ ID NO:138 |
| HVR3* | 202-204 | NTE | SEQ ID NO:139 |
| HVR4* | 239-248 | KTGENGKPTE | SEQ ID NO:140 |
| HVR5* | 259-270 | LRQNDTGGNNNQ | SEQ ID NO:141 |
| HVR6* | 295-297 | TSD | SEQ ID NO:142 |
| HVR7* | 421-436 | DTTVAGTNDKWKVNAK | SEQ ID NO:143 |
| Ad50 | | | |
| HVR1* | 137-150 | NKGDEEDGEDDQQA | SEQ ID NO:144 |
| HVR2* | 174-184 | LEVPSEGGPKP | SEQ ID NO:145 |
| HVR3* | 204-206 | DTD | SEQ ID NO:146 |
| HVR4* | 244-251 | KKEEEGKV | SEQ ID NO:147 |
| HVR5* | 262-270 | LRSQMTGLK | SEQ ID NO:148 |
| HVR6* | 295-297 | ASD | SEQ ID NO:149 |
| HVR7* | 422-433 | NGDETTTWKDLE | SEQ ID NO:150 |

REFERENCES

Barouch D H et al. (2004) Immunogenicity of recombinant adenovirus serotype 35 vaccine in the presence of pre-existing anti-Ad5 immunity. J Immunol 172:6290

Bergelson J M et al. (1997) Isolation of a common receptor for coxsackie B viruses and adenoviruses 2 and 5. Science 275:1320

Bewley M C et al. (1999) Structural analysis of the mechanism of adenovirus binding to its human cellular receptor, CAR. Science 286:1579

Farina S F et al. (2001) Replication-defective vector based on a chimpanzee adenovirus. J Virol 75:11603

Gaggar A et al. (2003) CD46 is a cellular receptor for group B adenoviruses. Nat Med 9:1408

Gall J G D et al. (1998) Construction and characterization of hexon-chimeric adenoviruses: specification of adenovirus serotype. J Virol 72:10260-10264

Ganesh S et al. (2003) Adenovirus 35 vectors with fiber chimeras exhibit altered tropism in vivo. Abstract 134. 2003 Meeting of the American Society of Gene Therapy. Molecular Therapy 7:S53

Gall J G et al. (1998) Construction and characterization of hexon-chimeric adenoviruses: specification of adenovirus serotype. J Virol 72:10260

Havenga M J et al. (2002) Exploiting the natural diversity in adenovirus tropism for therapy and prevention of disease. J Virol 76:4612

Kostense S et al. (2004) Adenovirus types 5 and 35 seroprevalence in AIDS risk groups supports type 35 as a vaccine vector. AIDS 18:1213

Lemckert A A C et al. (2005) Immunogenicity of heterologous prime-boost regimens involving recombinant adenovirus serotype 11 and 35 vaccine vectors in the presence of anti-Ad5 immunity. J Virol, in press Letvin N L et al. (2002) Prospects for vaccine protection against HIV-1 infection and AIDS. Annu Rev Immunol 20:73

Ophorst O J et al (2004) An adenoviral type 5 vector carrying a type 35 fiber as a vaccine vehicle: DC targeting, cross-neutralization, and immunogenicity. Vaccine 22:3035

Pinto A R et al. (2003) Induction of CD8+ T cells to an HIV-1 antigen through a prime boost regimen with heterologous E1-deleted adenoviral vaccine carriers. J Immunol 171:6774

Rea D et al. (2001) Highly efficient transduction of human monocyte-derived dendritic cells with subgroup B fiber-modified adenovirus vectors enhances transgene-encoded antigen presentation to cytotoxic T cells. J Immunol 166:5236

Roelvink P W et al. (1998) The coxsackievirus-adenovirus receptor protein can function as a cellular attachment protein for adenovirus serotypes from subgroups A, C, D, E, and F. J Virol 72:7909

Roelvink P W et al. (1999) Identification of a conserved receptor-binding site on the fiber proteins of CAR-recognizing adenoviridae. Science 286:1568

Shayakhmetov D M et al. (2003) The interaction between the fiber knob domain and the cellular attachment receptor determines the intracellular trafficking route of adenoviruses. J Virol 77:3712

Shiver J W et al. (2002) Replication-incompetent adenoviral vaccine vector elicits effective anti-immunodeficiency-virus immunity. Nature 415:331

Shiver J W and Emini E A (2004) Recent advances in the development of HIV-1 vaccines using replication-incompetent adenovirus vectors. Annu Rev Med 55:355

Shiver J W (2004) Development of an HIV-1 vaccine based on replication-defective adenovirus. Keystone Symposium on HIV Vaccine Development: Progress and Prospects, Whistler, British Columbia, Canada.

Smith T A G et al. (2003) Adenovirus serotype 5 fiber shaft influences in vivo gene transfer in mice. Hum Gene Ther 14:777

Sprangers M C et al. (2003) Quantifying adenovirus-neutralizing antibodies by luciferase transgene detection: addressing preexisting immunity to vaccine and gene therapy vectors. J Clin Microbiol 41:5046

Sumida S M et al. (2004) Neutralizing antibodies and CD8+ T lymphocytes both contribute to immunity to adenovirus serotype 5 vaccine vectors. J Virol 78:2666

Sumida S M et al. (2005) Neutralizing antibodies to adenovirus serotype 5 vaccine vectors are directed primarily against the adenovirus hexon protein. J Immunol 174:7179-7185

Vogels R et al. (2003) Replication-deficient human adenovirus type 35 vectors for gene transfer and vaccination: efficient human cell interaction and bypass of pre-existing adenovirus immunity. J Virol 77:8263

Wickham T J et al. (1993) Integrins alpha v beta 3 and alpha v beta 5 promote adenovirus internalization but not virus attachment. Cell 73:309

Worgall S et al. (2005) Protection against *P. aeruginosa* with an adenovirus vector containing an OprF epitope in the capsid. J Clin Invest 115:1281-1289

Youil R et al. (2002) Hexon gene switch strategy for the generation of chimeric recombinant adenovirus. Hum Gene Ther 13:311

The invention claimed is:

1. A batch of recombinant replication-defective adenovirus based upon adenovirus serotype 5 (Ad5), the recombinant replication-defective adenovirus comprising a chimeric hexon protein, wherein in the chimeric hexon protein hypervariable region sequences HVR1 to HVR7 of Ad5 have been replaced with those of Ad48 or of Pan9, in the following manner:

the HVR1 sequence of Ad5 (SEQ ID NO: 17) has been replaced by a sequence selected from the group consisting of SEQ ID NO: 24, and 52, the HVR2 sequence of Ad5 (SEQ ID NO: 18) has been replaced by a sequence selected from the group consisting of SEQ ID NO: 25, and 53, the HVR3 sequence of Ad5 (SEQ ID NO: 19) has been replaced by a sequence selected from the group consisting of SEQ ID NO: 26, and 54, the HVR4 sequence of Ad5 (SEQ ID NO: 20) has been replaced by a sequence selected from the group consisting of SEQ ID NO: 27, and 55, the HVR5 sequence of Ad5 (SEQ ID NO: 21) has been replaced by a sequence selected from the group consisting of SEQ ID NO: 28, and 56, the HVR6 sequence of Ad5 (SEQ ID NO: 22) has been replaced by a sequence selected from the group consisting of SEQ ID NO: 29, and 57, and the HVR7 sequence of Ad5 (SEQ ID NO: 23) has been replaced by a sequence selected from the group consisting of SEQ ID NO: 30, and 58, and wherein the sequences between the HVR sequences are from Ad5.

2. A recombinant adenovirus comprising a chimeric hexon protein, wherein the sequence of the chimeric hexon protein consists of SEQ ID NO: 12.

3. A batch of recombinant replication defective adenovirus based upon adenovirus serotype 5 (Ad5), the recombinant replication-defective adenovirus, comprising a chimeric hexon protein, wherein the chimeric hexon protein hypervariable region sequences HVR1 to HVR7 of Ad5 have been replaced with those of Ad48 in the following manner:

the HVR1 sequence of Ad5 (SEQ ID NO: 17) has been replaced by an amino acid sequence consisting of SEQ ID NO: 24, the HVR2 sequence of Ad5 (SEQ ID NO: 18) has been replaced by an amino acid sequence consisting of SEQ ID NO: 25, the HVR3 sequence of Ad5 (SEQ ID NO: 19) has been replaced by an amino acid sequence consisting of SEQ ID NO: 26, the HVR4 sequence of Ad5 (SEQ ID NO: 20) has been replaced by an amino acid sequence consisting of SEQ ID NO: 27, the HVR5 sequence of Ad5 (SEQ ID NO: 21.) has been replaced by an amino acid sequence consisting of SEQ ID NO: 28, the HVR7 sequence of Ad5 (SEQ ID NO: 22) has been replaced by an amino acid sequence consisting of SEQ ID NO: 29, and the HVR7 sequence of Ad5 (SEQ ID NO: 23) has been replaced by an amino acid sequence consisting of SEQ ID NO: 30, and wherein the sequences between the HVR sequences are from Ad5.

4. The batch of claim 1, wherein the replication-defective adenovirus comprises a heterologous nucleic acid of interest.

5. The batch of claim 3, wherein the replication-defective adenovirus comprises a heterologous nucleic acid of interest.

6. The recombinant adenovirus of claim 2, wherein the recombinant adenovirus comprises a heterologous nucleic acid of interest.

7. The recombinant adenovirus of claim 2, comprising an adenoviral genome having a deletion in the E1 region.

8. The recombinant adenovirus of claim 7, wherein the adenoviral genome further has a deletion in the E3 region.

9. The batch of claim 1, wherein the replication-defective adenovirus comprises an adenoviral genome having a deletion in the E1 region.

10. The batch of claim 7, wherein the adenoviral genome further has a deletion in the E3 region.

11. The batch of claim 3, wherein the replication-defective adenovirus comprises an adenoviral genome having a deletion in the E1 region.

12. The batch of claim 11, wherein the adenoviral genome further has a deletion in the E3 region.

* * * * *

UNITED STATES PATENT AND TRADEMARK OFFICE
CERTIFICATE OF CORRECTION

PATENT NO.       : 7,741,099 B2                                  Page 1 of 1
APPLICATION NO.  : 11/665276
DATED            : June 22, 2010
INVENTOR(S)      : Havenga It is certified that error appears in the above-identified patent and that said Letters Patent is hereby corrected as shown below:

In the claim

CLAIM 10, COLUMN 132, LINE 45,        change "claim 7," to --claim 9,--

Signed and Sealed this
Twenty-fourth Day of December, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO. : 7,741,099 B2  
APPLICATION NO. : 11/665276  
DATED : June 22, 2010  
INVENTOR(S) : Menzo Jans Emco Havenga and Dan H. Barouch It is certified that error appears in the above-identified patent and that said Letters Patent is hereby corrected as shown below:

In the specification include Government Rights, Column 1, line 15:

This invention was made with government support under Contract No. AI060368 awarded by The Government of the United States of America as represented by The Secretary of the Department of Health and Human Services, Office of Technology Transfer, National Institute of Health. The government has certain rights in the invention.

Signed and Sealed this
Thirteenth Day of January, 2015

Michelle K. Lee
*Deputy Director of the United States Patent and Trademark Office*

UNITED STATES PATENT AND TRADEMARK OFFICE
CERTIFICATE OF CORRECTION

Page 1 of 1

PATENT NO. : 7,741,099 B2
APPLICATION NO. : 11/665276
DATED : June 22, 2010
INVENTOR(S) : Menzo Jans Emco Havenga and Dan H. Barouch It is certified that error appears in the above-identified patent and that said Letters Patent is hereby corrected as shown below:

In the specification:

| | | |
|---|---|---|
| COLUMN 1, | LINE 16, | before "FIELD OF THE INVENTION" insert heading --GOVERNMENT RIGHTS-- |
| COLUMN 1, | LINE 18, | after the above heading and 2 line breaks, insert paragraph --This invention was made with government support under AI060368 awarded by NIH. The government has certain rights in the invention.-- |

Signed and Sealed this
Fourteenth Day of June, 2016

Michelle K. Lee
*Director of the United States Patent and Trademark Office*

SEQUENCE LISTING

```
<160> NUMBER OF SEQ ID NOS: 150

<210> SEQ ID NO 1
<211> LENGTH: 951
<212> TYPE: DNA
<213> ORGANISM: Artificial
<220> FEATURE:
<223> OTHER INFORMATION: Nucleic acid encoding a chimeric human
      adenovirus Ad35-Ad5 fiber protein

<400> SEQUENCE: 1
atgaccaaga gagtccggct cagtgactcc ttcaaccctg tctacccgta cgaagatgaa      60
agcacctccc aacaccccctt tataaaccca gggtttattt ccccaaatgg cttcacacaa    120
agcccagacg gagttcttac tttaaaatgt ttaaccccac taacaaccac aggcggatct    180
ctacagctaa aagtgggagg gggacttaca gtggatgaca ctgatggtac cttacaagaa    240
aacatacgtg ctacagcacc cattactaaa ataatcact ctgtagaact atccattgga    300
aatggattag aaactcaaaa caataaacta tgtgccaaat tgggaaatgg gttaaaattt    360
aacaacggtg acatttgtat aaaggatagt attaacactt tgtggaccac accagctcca    420
tctcctaact gtagactaaa tgcagagaaa gatgctaaac tcactttggt cttaacaaaa    480
tgtggcagtc aaatacttgc tacagtttca gtttttggctg ttaaaggcag tttggctcca    540
atatctggaa cagttcaaag tgctcatctt attataagat ttgacgaaaa tggagtgcta    600
ctaaacaatt ccttcctgga cccagaatat tggaacttta gaaatggaga tcttactgaa    660
ggcacagcct atacaaacgc tgttggattt atgcctaacc tatcagctta tccaaaatct    720
cacggtaaaa ctgccaaaag taacattgtc agtcaagttt acttaaacgg agacaaaact    780
aaacctgtaa cactaaccat tacactaaac ggtacacagg aaacaggaga cacaactcca    840
agtgcatact ctatgtcatt ttcatgggac tggtctggcc acaactacat taatgaaata    900
tttgccacat cctcttacac tttttcatac attgcccaag ataagctag c                951

<210> SEQ ID NO 2
<211> LENGTH: 314
<212> TYPE: PRT
<213> ORGANISM: Artificial
<220> FEATURE:
<223> OTHER INFORMATION: Human adenovirus chimeric Ad35-Ad5 fiber
      protein
```

```
<400> SEQUENCE: 2

Met Thr Lys Arg Val Arg Leu Ser Asp Ser Phe Asn Pro Val Tyr Pro
1               5                   10                  15

Tyr Glu Asp Glu Ser Thr Ser Gln His Pro Phe Ile Asn Pro Gly Phe
            20                  25                  30

Ile Ser Pro Asn Gly Phe Thr Gln Ser Pro Asp Gly Val Leu Thr Leu
            35                  40                  45

Lys Cys Leu Thr Pro Leu Thr Thr Gly Gly Ser Leu Gln Leu Lys
50                  55                  60

Val Gly Gly Gly Leu Thr Val Asp Asp Thr Asp Gly Thr Leu Gln Glu
65                  70                  75                  80

Asn Ile Arg Ala Thr Ala Pro Ile Thr Lys Asn Asn His Ser Val Glu
                85                  90                  95

Leu Ser Ile Gly Asn Gly Leu Glu Thr Gln Asn Asn Lys Leu Cys Ala
            100                 105                 110

Lys Leu Gly Asn Gly Leu Lys Phe Asn Asn Gly Asp Ile Cys Ile Lys
            115                 120                 125

Asp Ser Ile Asn Thr Leu Trp Thr Thr Pro Ala Pro Ser Pro Asn Cys
            130                 135                 140

Arg Leu Asn Ala Glu Lys Asp Ala Lys Leu Thr Leu Val Leu Thr Lys
145                 150                 155                 160

Cys Gly Ser Gln Ile Leu Ala Thr Val Ser Val Leu Ala Val Lys Gly
                165                 170                 175

Ser Leu Ala Pro Ile Ser Gly Thr Val Gln Ser Ala His Leu Ile Ile
            180                 185                 190

Arg Phe Asp Glu Asn Gly Val Leu Leu Asn Asn Ser Phe Leu Asp Pro
            195                 200                 205

Glu Tyr Trp Asn Phe Arg Asn Gly Asp Leu Thr Glu Gly Thr Ala Tyr
            210                 215                 220

Thr Asn Ala Val Gly Phe Met Pro Asn Leu Ser Ala Tyr Pro Lys Ser
225                 230                 235                 240

His Gly Lys Thr Ala Lys Ser Asn Ile Val Ser Gln Val Tyr Leu Asn
                245                 250                 255

Gly Asp Lys Thr Lys Pro Val Thr Leu Thr Ile Thr Leu Asn Gly Thr
            260                 265                 270

Gln Glu Thr Gly Asp Thr Thr Pro Ser Ala Tyr Ser Met Ser Phe Ser
            275                 280                 285

Trp Asp Trp Ser Gly His Asn Tyr Ile Asn Glu Ile Phe Ala Thr Ser
            290                 295                 300

Ser Tyr Thr Phe Ser Tyr Ile Ala Gln Glu
305                 310

<210> SEQ ID NO 3
<211> LENGTH: 11
<212> TYPE: PRT
<213> ORGANISM: Artificial
<220> FEATURE:
<223> OTHER INFORMATION: SIVmac239 Gag AL11 epitope peptide

<400> SEQUENCE: 3

Ala Ala Val Lys Asn Trp Met Thr Gln Thr Leu
1               5                   10

<210> SEQ ID NO 4
<211> LENGTH: 1746
```

<212> TYPE: DNA
<213> ORGANISM: Artificial
<220> FEATURE:
<223> OTHER INFORMATION: Nucleic acid encoding a chimeric human
     adenovirus Ad35-Ad5 fiber protein

<400> SEQUENCE: 4

```
atgaccaaga gagtccggct cagtgactcc ttcaaccctg tctacccgta cgacacggaa      60
accggtcctc caactgtgcc ttttcttact cctccctttg tatcccccaa tgggtttcaa     120
gagagtcccc ctggggtact ctctttgcgc ctatccgaac tctagttac ctccaatggc      180
atgcttgcgc tcaaaatggg caacggcctc tctctggacg aggccggcaa ccttacctcc     240
caaaatgtaa ccactgtgag cccacctctc aaaaaaacca agtcaaacat aaacctggaa     300
atatctgcac ccctcacagt tacctcagaa gccctaactg tggctgccgc cgcacctcta     360
atggtcgcgg caacacact caccatgcaa tcacaggccc cgctaaccgt gcacgactcc     420
aaacttagca ttgccaccca aggacccctc acagtgtcag aaggaaagct agccctgcaa     480
acatcaggcc cctcaccac accgatagca gtaccctta ctatcactgc ctcacccct       540
ctaactactg ccactggtag cttgggcatt gacttgaaag agcccatttt atacacaaaat   600
ggaaaactag gactaaagta cggggctcct ttgcatgtaa cagacgacct aaacactttg    660
accgtagcaa ctggtccagg tgtgactatt aataatactt ccttgcaaac taaagttact    720
ggagccttgg gttttgattc acaaggcaat atgcaactta atgtagcagg aggactaagg    780
attgattctc aaaacagacg ccttatactt gatgttagtt atccgtttga tgctcaaaac    840
caactaaatc taagactagg acagggccct ctttttataa actcagccca aacttggat    900
attaactaca caaaaggcct ttacttgttt acagcttcaa acaattccaa aaagcttgag    960
gttaacctaa gcactgccaa ggggttgatg tttgacgcta cagccatagc cattaatgca   1020
ggagatgggc ttgaatttgg ttcacctaat gcaccaaaca caatccct caaaacaaaa     1080
attggccatg cctagaatt tgattcaaac aaggctatgg ttcctaaact aggaactggc    1140
cttagttttg acagcacagg tgccattaca gtaggaaaca aaataatga taagctaact    1200
ttgtggacca caccagctcc atctcctaac tgtagactaa atgcagagaa agatgctaaa   1260
ctcacttttgg tcttaacaaa atgtggcagt caaatacttg ctacagtttc agttttggct  1320
gttaaaggca gtttggctcc aatatctgga acagttcaaa gtgctcatct tattataaga  1380
tttgacgaaa atgagagtgct actaaacaat tccttcctgg accagaata ttggaacttt   1440
agaaatggag atcttactga aggcacagcc tatacaaacg ctgttggatt tatgcctaac   1500
ctatcagctt atccaaaatc tcacggtaaa actgccaaaa gtaacattgt cagtcaagtt   1560
tacttaaacg gagacaaaac taaacctgta acactaacca ttcactaaa cggtacacag   1620
gaaacaggag acacaactcc aagtgcatac tctatgtcat ttcatggga ctggtctggc   1680
cacaactaca ttaatgaaat atttgccaca tcctcttaca cttttttcata cattgcccaa  1740
gaataa                                                              1746
```

<210> SEQ ID NO 5
<211> LENGTH: 581
<212> TYPE: PRT
<213> ORGANISM: Artificial
<220> FEATURE:
<223> OTHER INFORMATION: Human adenovirus chimeric Ad35-Ad5 fiber
     protein

<400> SEQUENCE: 5

-continued

```
Met Thr Lys Arg Val Arg Leu Ser Asp Ser Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Leu Ala Leu
    50                  55                  60

Lys Met Gly Asn Gly Leu Ser Leu Asp Glu Ala Gly Asn Leu Thr Ser
65              70                  75                  80

Gln Asn Val Thr Thr Val Ser Pro Pro Leu Lys Lys Thr Lys Ser Asn
            85                  90                  95

Ile Asn Leu Glu Ile Ser Ala Pro Leu Thr Val Thr Ser Glu Ala Leu
            100                 105                 110

Thr Val Ala Ala Ala Ala Pro Leu Met Val Ala Gly Asn Thr Leu Thr
            115                 120                 125

Met Gln Ser Gln Ala Pro Leu Thr Val His Asp Ser Lys Leu Ser Ile
    130                 135                 140

Ala Thr Gln Gly Pro Leu Thr Val Ser Glu Gly Lys Leu Ala Leu Gln
145                 150                 155                 160

Thr Ser Gly Pro Leu Thr Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
    210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
            260                 265                 270

Ser Tyr Pro Phe Asp Ala Gln Asn Gln Leu Asn Leu Arg Leu Gly Gln
        275                 280                 285

Gly Pro Leu Phe Ile Asn Ser Ala His Asn Leu Asp Ile Asn Tyr Asn
    290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
        355                 360                 365

Ser Asn Lys Ala Met Val Pro Lys Leu Gly Thr Gly Leu Ser Phe Asp
    370                 375                 380

Ser Thr Gly Ala Ile Thr Val Gly Asn Lys Asn Asp Lys Leu Thr
385                 390                 395                 400

Leu Trp Thr Thr Pro Ala Pro Ser Pro Asn Cys Arg Leu Asn Ala Glu
                405                 410                 415

Lys Asp Ala Lys Leu Thr Leu Val Leu Thr Lys Cys Gly Ser Gln Ile
```

-continued

```
                    420                 425                 430
Leu Ala Thr Val Ser Val Leu Ala Val Lys Gly Ser Leu Ala Pro Ile
            435                 440                 445
Ser Gly Thr Val Gln Ser Ala His Leu Ile Ile Arg Phe Asp Glu Asn
        450                 455                 460
Gly Val Leu Leu Asn Asn Ser Phe Leu Asp Pro Glu Tyr Trp Asn Phe
465                 470                 475                 480
Arg Asn Gly Asp Leu Thr Glu Gly Thr Ala Tyr Thr Asn Ala Val Gly
                485                 490                 495
Phe Met Pro Asn Leu Ser Ala Tyr Pro Lys Ser His Gly Lys Thr Ala
            500                 505                 510
Lys Ser Asn Ile Val Ser Gln Val Tyr Leu Asn Gly Asp Lys Thr Lys
        515                 520                 525
Pro Val Thr Leu Thr Ile Thr Leu Asn Gly Thr Gln Glu Thr Gly Asp
530                 535                 540
Thr Thr Pro Ser Ala Tyr Ser Met Ser Phe Ser Trp Asp Trp Ser Gly
545                 550                 555                 560
His Asn Tyr Ile Asn Glu Ile Phe Ala Thr Ser Ser Tyr Thr Phe Ser
                565                 570                 575
Tyr Ile Ala Gln Glu
            580
```

<210> SEQ ID NO 6
<211> LENGTH: 20
<212> TYPE: DNA
<213> ORGANISM: Artificial
<220> FEATURE:
<223> OTHER INFORMATION: Synthetic oligonucleotide DF35-1

<400> SEQUENCE: 6
cactcaccac ctccaattcc                                              20

<210> SEQ ID NO 7
<211> LENGTH: 32
<212> TYPE: DNA
<213> ORGANISM: Artificial
<220> FEATURE:
<223> OTHER INFORMATION: Synthetic oligonucleotide DF35-2

<400> SEQUENCE: 7
cgggatcccg tacgggtaga cagggttgaa gg                                32

<210> SEQ ID NO 8
<211> LENGTH: 49
<212> TYPE: DNA
<213> ORGANISM: Artificial
<220> FEATURE:
<223> OTHER INFORMATION: Synthetic oligonucleotide DF35-3

<400> SEQUENCE: 8
cgggatccgc tagctgaaat aaagtttaag tgttttatt taaaatcac               49

<210> SEQ ID NO 9
<211> LENGTH: 21
<212> TYPE: DNA
<213> ORGANISM: Artificial
<220> FEATURE:
<223> OTHER INFORMATION: Synthetic oligonucleotide DF35-4

<400> SEQUENCE: 9
ccagttgcat tgcttggttg g                                            21

<210> SEQ ID NO 10
<211> LENGTH: 31
<212> TYPE: DNA
<213> ORGANISM: Artificial
<220> FEATURE:
<223> OTHER INFORMATION: Synthetic oligonucleotide 35F5-5-F

<400> SEQUENCE: 10
cgggaacgta cgacacggaa accggtcctc c    31

<210> SEQ ID NO 11
<211> LENGTH: 35
<212> TYPE: DNA
<213> ORGANISM: Artificial
<220> FEATURE:
<223> OTHER INFORMATION: Synthetic oligonucleotide 35F5-R

<400> SEQUENCE: 11
cggctagcta gcttattctt gggcaatgta tgaaa    35

<210> SEQ ID NO 12
<211> LENGTH: 947
<212> TYPE: PRT
<213> ORGANISM: Artificial
<220> FEATURE:
<223> OTHER INFORMATION: Chimeric adenovirus hexon protein Ad5HVR48(1-7)

<400> SEQUENCE: 12

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Glu Glu Lys Asn Gly Gly Gly Ser
    130                 135                 140

Asp Ala Asn Gln Met Gln Thr His Val Phe Gly Gln Ala Pro Tyr Ser
145                 150                 155                 160

Gly Ile Asn Ile Thr Lys Glu Gly Ile Gln Ile Gly Ile Asp Ala Thr
                165                 170                 175

Lys Glu Glu Asp Asn Gly Lys Glu Ile Tyr Ala Asp Lys Thr Phe Gln
            180                 185                 190

Pro Glu Pro Gln Ile Gly Glu Ser Gln Trp Gln Asp Ser Asp Asn Tyr
        195                 200                 205

Tyr Gly Gly Arg Val Leu Lys Lys Thr Thr Pro Met Lys Pro Cys Tyr
    210                 215                 220

Gly Ser Tyr Ala Lys Pro Thr Asn Glu Asn Gly Gly Gln Ala Lys Phe
225                 230                 235                 240

-continued

Lys Thr Pro Glu Lys Glu Gly Glu Pro Lys Glu Ser Gln Val Glu
            245                 250                 255

Met Gln Phe Phe Asp Ile Pro Ser Thr Gly Thr Gly Gly Asn Gly Thr
            260                 265                 270

Asn Val Asn Phe Lys Pro Lys Val Val Leu Tyr Ser Glu Asp Val Asp
            275                 280                 285

Ile Glu Thr Pro Asp Thr His Ile Ser Tyr Met Pro Gly Lys Glu Asp
            290                 295                 300

Ala Ser Ser Arg Glu Leu Met Gly Gln Gln Ser Met Pro Asn Arg Pro
305                 310                 315                 320

Asn Tyr Ile Ala Phe Arg Asp Asn Phe Ile Gly Leu Met Tyr Tyr Asn
            325                 330                 335

Ser Thr Gly Asn Met Gly Val Leu Ala Gly Gln Ala Ser Gln Leu Asn
            340                 345                 350

Ala Val Val Asp Leu Gln Asp Arg Asn Thr Glu Leu Ser Tyr Gln Leu
            355                 360                 365

Leu Leu Asp Ser Ile Gly Asp Arg Thr Arg Tyr Phe Ser Met Trp Asn
            370                 375                 380

Gln Ala Val Asp Ser Tyr Asp Pro Asp Val Arg Ile Ile Glu Asn His
385                 390                 395                 400

Gly Thr Glu Asp Glu Leu Pro Asn Tyr Cys Phe Pro Leu Asp Gly Ala
            405                 410                 415

Gly Thr Asn Ala Val Tyr Gln Gly Val Lys Val Lys Thr Thr Asn Asn
            420                 425                 430

Thr Glu Trp Glu Lys Asp Thr Ala Val Ser Glu His Asn Gln Ile Arg
            435                 440                 445

Val Gly Asn Asn Phe Ala Met Glu Ile Asn Leu Asn Ala Asn Leu Trp
            450                 455                 460

Arg Asn Phe Leu Tyr Ser Asn Ile Ala Leu Tyr Leu Pro Asp Lys Leu
465                 470                 475                 480

Lys Tyr Ser Pro Ser Asn Val Lys Ile Ser Asp Asn Pro Asn Thr Tyr
            485                 490                 495

Asp Tyr Met Asn Lys Arg Val Val Ala Pro Gly Leu Val Asp Cys Tyr
            500                 505                 510

Ile Asn Leu Gly Ala Arg Trp Ser Leu Asp Tyr Met Asp Asn Val Asn
            515                 520                 525

Pro Phe Asn His His Arg Asn Ala Gly Leu Arg Tyr Arg Ser Met Leu
            530                 535                 540

Leu Gly Asn Gly Arg Tyr Val Pro Phe His Ile Gln Val Pro Gln Lys
545                 550                 555                 560

Phe Phe Ala Ile Lys Asn Leu Leu Leu Pro Gly Ser Tyr Thr Tyr
            565                 570                 575

Glu Trp Asn Phe Arg Lys Asp Val Asn Met Val Leu Gln Ser Ser Leu
            580                 585                 590

Gly Asn Asp Leu Arg Val Asp Gly Ala Ser Ile Lys Phe Asp Ser Ile
            595                 600                 605

Cys Leu Tyr Ala Thr Phe Phe Pro Met Ala His Asn Thr Ala Ser Thr
            610                 615                 620

Leu Glu Ala Met Leu Arg Asn Asp Thr Asn Asp Gln Ser Phe Asn Asp
625                 630                 635                 640

Tyr Leu Ser Ala Ala Asn Met Leu Tyr Pro Ile Pro Ala Asn Ala Thr
            645                 650                 655

Asn Val Pro Ile Ser Ile Pro Ser Arg Asn Trp Ala Ala Phe Arg Gly
              660                 665                 670

Trp Ala Phe Thr Arg Leu Lys Thr Lys Glu Thr Pro Ser Leu Gly Ser
              675                 680                 685

Gly Tyr Asp Pro Tyr Tyr Thr Tyr Ser Gly Ser Ile Pro Tyr Leu Asp
              690                 695                 700

Gly Thr Phe Tyr Leu Asn His Thr Phe Lys Lys Val Ala Ile Thr Phe
705                 710                 715                 720

Asp Ser Ser Val Ser Trp Pro Gly Asn Asp Arg Leu Leu Thr Pro Asn
              725                 730                 735

Glu Phe Glu Ile Lys Arg Ser Val Asp Gly Gly Tyr Asn Val Ala
              740                 745                 750

Gln Cys Asn Met Thr Lys Asp Trp Phe Leu Val Gln Met Leu Ala Asn
              755                 760                 765

Tyr Asn Ile Gly Tyr Gln Gly Phe Tyr Ile Pro Glu Ser Tyr Lys Asp
              770                 775                 780

Arg Met Tyr Ser Phe Phe Arg Asn Phe Gln Pro Met Ser Arg Gln Val
785                 790                 795                 800

Val Asp Asp Thr Lys Tyr Lys Asp Tyr Gln Gln Val Gly Ile Leu His
              805                 810                 815

Gln His Asn Asn Ser Gly Phe Val Gly Tyr Leu Ala Pro Thr Met Arg
              820                 825                 830

Glu Gly Gln Ala Tyr Pro Ala Asn Phe Pro Tyr Pro Leu Ile Gly Lys
              835                 840                 845

Thr Ala Val Asp Ser Ile Thr Gln Lys Lys Phe Leu Cys Asp Arg Thr
              850                 855                 860

Leu Trp Arg Ile Pro Phe Ser Ser Asn Phe Met Ser Met Gly Ala Leu
865                 870                 875                 880

Thr Asp Leu Gly Gln Asn Leu Leu Tyr Ala Asn Ser Ala His Ala Leu
              885                 890                 895

Asp Met Thr Phe Glu Val Asp Pro Met Asp Glu Pro Thr Leu Leu Tyr
              900                 905                 910

Val Leu Phe Glu Val Phe Asp Val Val Arg Val His Arg Pro His Arg
              915                 920                 925

Gly Val Ile Glu Thr Val Tyr Leu Arg Thr Pro Phe Ser Ala Gly Asn
              930                 935                 940

Ala Thr Thr
945

<210> SEQ ID NO 13
<211> LENGTH: 951
<212> TYPE: PRT
<213> ORGANISM: Artificial
<220> FEATURE:
<223> OTHER INFORMATION: Chimeric adenovirus hexon protein Ad5HVR35(1-7)

<400> SEQUENCE: 13

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
              20                  25                  30

Arg Ala Thr Glu Thr Tyr Phe Ser Leu Asn Asn Lys Phe Arg Asn Pro
              35                  40                  45

Thr Val Ala Pro Thr His Asp Val Thr Thr Asp Arg Ser Gln Arg Leu
              50                  55                  60

```
Thr Leu Arg Phe Ile Pro Val Asp Arg Glu Asp Thr Ala Tyr Ser Tyr
 65                  70                  75                  80

Lys Ala Arg Phe Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Ile Ala Lys Gly Val Pro Thr Ala Ala
    130                 135                 140

Ala Ala Gly Asn Gly Glu Glu His Glu Thr Glu Glu Lys Thr Ala
145                 150                 155                 160

Thr His Val Phe Gly Gln Ala Pro Tyr Ser Gly Ile Asn Ile Thr Lys
                165                 170                 175

Glu Gly Ile Gln Ile Gly Leu Glu Ile Ser Ala Glu Asn Glu Ser Lys
            180                 185                 190

Pro Ile Tyr Ala Asp Lys Thr Phe Gln Pro Glu Pro Gln Ile Gly Glu
        195                 200                 205

Ser Gln Trp Thr Asp Leu Asp Gly Lys Thr Glu Tyr Gly Gly Arg
    210                 215                 220

Val Leu Lys Lys Thr Thr Pro Met Lys Pro Cys Tyr Gly Ser Tyr Ala
225                 230                 235                 240

Lys Pro Thr Asn Glu Asn Gly Gly Gln Ala Lys Pro Lys Asn Ser Glu
                245                 250                 255

Pro Ser Ser Glu Lys Ile Glu Ser Gln Val Glu Met Gln Phe Phe Asp
            260                 265                 270

Asn Ser Ser Gln Arg Thr Asn Phe Ser Pro Lys Val Val Leu Tyr Ser
        275                 280                 285

Glu Asp Val Asp Ile Glu Thr Pro Asp Thr His Ile Ser Tyr Met Pro
    290                 295                 300

Gly Thr Glu Asp Thr Ser Ser Arg Glu Leu Met Gly Gln Gln Ser Met
305                 310                 315                 320

Pro Asn Arg Pro Asn Tyr Ile Ala Phe Arg Asp Asn Phe Ile Gly Leu
                325                 330                 335

Met Tyr Tyr Asn Ser Thr Gly Asn Met Gly Val Leu Ala Gly Gln Ala
            340                 345                 350

Ser Gln Leu Asn Ala Val Val Asp Leu Gln Asp Arg Asn Thr Glu Leu
        355                 360                 365

Ser Tyr Gln Leu Leu Asp Ser Ile Gly Asp Arg Thr Arg Tyr Phe
    370                 375                 380

Ser Met Trp Asn Gln Ala Val Asp Ser Tyr Asp Pro Asp Val Arg Ile
385                 390                 395                 400

Ile Glu Asn His Gly Thr Glu Asp Glu Leu Pro Asn Tyr Cys Phe Pro
                405                 410                 415

Leu Asp Gly Ile Gly Val Pro Thr Thr Ser Tyr Lys Ser Ile Val Pro
            420                 425                 430

Asn Gly Glu Asp Asn Asn Trp Lys Glu Pro Glu Val Asn Gly Thr
        435                 440                 445

Ser Glu Ile Arg Val Gly Asn Asn Phe Ala Met Glu Ile Asn Leu Asn
    450                 455                 460

Ala Asn Leu Trp Arg Asn Phe Leu Tyr Ser Asn Ile Ala Leu Tyr Leu
465                 470                 475                 480

Pro Asp Lys Leu Lys Tyr Ser Pro Ser Asn Val Lys Ile Ser Asp Asn
```

-continued

```
                485                 490                 495
Pro Asn Thr Tyr Asp Tyr Met Asn Lys Arg Val Ala Pro Gly Leu
            500                 505                 510
Val Asp Cys Tyr Ile Asn Leu Gly Ala Arg Trp Ser Leu Asp Tyr Met
            515                 520                 525
Asp Asn Val Asn Pro Phe Asn His His Arg Asn Ala Gly Leu Arg Tyr
            530                 535                 540
Arg Ser Met Leu Leu Gly Asn Gly Arg Tyr Val Pro Phe His Ile Gln
545                 550                 555                 560
Val Pro Gln Lys Phe Ala Ile Lys Asn Leu Leu Leu Pro Gly
            565                 570                 575
Ser Tyr Thr Tyr Glu Trp Asn Phe Arg Lys Asp Val Asn Met Val Leu
            580                 585                 590
Gln Ser Ser Leu Gly Asn Asp Leu Arg Val Asp Gly Ala Ser Ile Lys
            595                 600                 605
Phe Asp Ser Ile Cys Leu Tyr Ala Thr Phe Pro Met Ala His Asn
    610                 615                 620
Thr Ala Ser Thr Leu Glu Ala Met Leu Arg Asn Asp Thr Asn Asp Gln
625                 630                 635                 640
Ser Phe Asn Asp Tyr Leu Ser Ala Ala Asn Met Leu Tyr Pro Ile Pro
            645                 650                 655
Ala Asn Ala Thr Asn Val Pro Ile Ser Ile Pro Ser Arg Asn Trp Ala
            660                 665                 670
Ala Phe Arg Gly Trp Ala Phe Thr Arg Leu Lys Thr Lys Glu Thr Pro
            675                 680                 685
Ser Leu Gly Ser Gly Tyr Asp Pro Tyr Tyr Thr Tyr Ser Gly Ser Ile
            690                 695                 700
Pro Tyr Leu Asp Gly Thr Phe Tyr Leu Asn His Thr Phe Lys Lys Val
705                 710                 715                 720
Ala Ile Thr Phe Asp Ser Ser Val Ser Trp Pro Gly Asn Asp Arg Leu
            725                 730                 735
Leu Thr Pro Asn Glu Phe Glu Ile Lys Arg Ser Val Asp Gly Glu Gly
            740                 745                 750
Tyr Asn Val Ala Gln Cys Asn Met Thr Lys Asp Trp Phe Leu Val Gln
            755                 760                 765
Met Leu Ala Asn Tyr Asn Ile Gly Tyr Gln Gly Phe Tyr Ile Pro Glu
            770                 775                 780
Ser Tyr Lys Asp Arg Met Tyr Ser Phe Phe Arg Asn Phe Gln Pro Met
785                 790                 795                 800
Ser Arg Gln Val Val Asp Asp Thr Lys Tyr Lys Asp Tyr Gln Gln Val
            805                 810                 815
Gly Ile Leu His Gln His Asn Asn Ser Gly Phe Val Gly Tyr Leu Ala
            820                 825                 830
Pro Thr Met Arg Glu Gly Gln Ala Tyr Pro Ala Asn Phe Pro Tyr Pro
            835                 840                 845
Leu Ile Gly Lys Thr Ala Val Asp Ser Ile Thr Gln Lys Lys Phe Leu
            850                 855                 860
Cys Asp Arg Thr Leu Trp Arg Ile Pro Phe Ser Ser Asn Phe Met Ser
865                 870                 875                 880
Met Gly Ala Leu Thr Asp Leu Gly Gln Asn Leu Leu Tyr Ala Asn Ser
            885                 890                 895
Ala His Ala Leu Asp Met Thr Phe Glu Val Asp Pro Met Asp Glu Pro
            900                 905                 910
```

-continued

Thr Leu Leu Tyr Val Leu Phe Glu Val Phe Asp Val Val Arg Val His
            915                 920                 925

Arg Pro His Arg Gly Val Ile Glu Thr Val Tyr Leu Arg Thr Pro Phe
        930                 935                 940

Ser Ala Gly Asn Ala Thr Thr
945                 950

<210> SEQ ID NO 14
<211> LENGTH: 947
<212> TYPE: PRT
<213> ORGANISM: Artificial
<220> FEATURE:
<223> OTHER INFORMATION: Chimeric adenovirus hexon protein Ad5HVR11(1-7)

<400> SEQUENCE: 14

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Ile Ala Glu Gly Val Lys Asn Thr Thr
    130                 135                 140

Gly Glu Glu His Val Thr Glu Glu Thr Asn Thr Thr Thr His Val
145                 150                 155                 160

Phe Gly Gln Ala Pro Tyr Ser Gly Ile Asn Ile Thr Lys Glu Gly Ile
                165                 170                 175

Gln Ile Gly Leu Glu Val Ser Asp Glu Glu Ser Lys Pro Ile Tyr Ala
            180                 185                 190

Asp Lys Thr Phe Gln Pro Glu Pro Gln Ile Gly Glu Ser Gln Trp Thr
        195                 200                 205

Asp Leu Asp Gly Lys Thr Glu Lys Tyr Gly Gly Arg Val Leu Lys Lys
    210                 215                 220

Thr Thr Pro Met Lys Pro Cys Tyr Gly Ser Tyr Ala Lys Pro Thr Asn
225                 230                 235                 240

Glu Asn Gly Gly Gln Ala Lys Gln Lys Thr Thr Glu Gln Pro Asn Gln
                245                 250                 255

Lys Val Glu Ser Gln Val Glu Met Gln Phe Phe Asp Ala Ala Ser Gln
            260                 265                 270

Lys Thr Asn Leu Ser Pro Lys Val Val Leu Tyr Ser Glu Asp Val Asp
        275                 280                 285

Ile Glu Thr Pro Asp Thr His Ile Ser Tyr Met Pro Gly Thr Glu Asp
    290                 295                 300

Thr Ser Ser Arg Glu Leu Met Gly Gln Gln Ser Met Pro Asn Arg Pro
305                 310                 315                 320

```
Asn Tyr Ile Ala Phe Arg Asp Asn Phe Ile Gly Leu Met Tyr Tyr Asn
            325                 330                 335

Ser Thr Gly Asn Met Gly Val Leu Ala Gly Gln Ala Ser Gln Leu Asn
        340                 345                 350

Ala Val Val Asp Leu Gln Asp Arg Asn Thr Glu Leu Ser Tyr Gln Leu
        355                 360                 365

Leu Leu Asp Ser Ile Gly Asp Arg Thr Arg Tyr Phe Ser Met Trp Asn
    370                 375                 380

Gln Ala Val Asp Ser Tyr Asp Pro Asp Val Arg Ile Ile Glu Asn His
385                 390                 395                 400

Gly Thr Glu Asp Glu Leu Pro Asn Tyr Cys Phe Pro Leu Asp Gly Ile
                405                 410                 415

Gly Val Pro Thr Thr Ser Tyr Lys Ser Ile Val Pro Asn Gly Asp Asn
            420                 425                 430

Ala Pro Asn Trp Lys Glu Pro Glu Val Asn Gly Thr Ser Glu Ile Arg
        435                 440                 445

Val Gly Asn Asn Phe Ala Met Glu Ile Asn Leu Asn Ala Asn Leu Trp
    450                 455                 460

Arg Asn Phe Leu Tyr Ser Asn Ile Ala Leu Tyr Leu Pro Asp Lys Leu
465                 470                 475                 480

Lys Tyr Ser Pro Ser Asn Val Lys Ile Ser Asp Asn Pro Asn Thr Tyr
                485                 490                 495

Asp Tyr Met Asn Lys Arg Val Val Ala Pro Gly Leu Val Asp Cys Tyr
            500                 505                 510

Ile Asn Leu Gly Ala Arg Trp Ser Leu Asp Tyr Met Asp Asn Val Asn
        515                 520                 525

Pro Phe Asn His His Arg Asn Ala Gly Leu Arg Tyr Arg Ser Met Leu
    530                 535                 540

Leu Gly Asn Gly Arg Tyr Val Pro Phe His Ile Gln Val Pro Gln Lys
545                 550                 555                 560

Phe Phe Ala Ile Lys Asn Leu Leu Leu Pro Gly Ser Tyr Thr Tyr
                565                 570                 575

Glu Trp Asn Phe Arg Lys Asp Val Asn Met Val Leu Gln Ser Ser Leu
            580                 585                 590

Gly Asn Asp Leu Arg Val Asp Gly Ala Ser Ile Lys Phe Asp Ser Ile
        595                 600                 605

Cys Leu Tyr Ala Thr Phe Phe Pro Met Ala His Asn Thr Ala Ser Thr
    610                 615                 620

Leu Glu Ala Met Leu Arg Asn Asp Thr Asn Asp Gln Ser Phe Asn Asp
625                 630                 635                 640

Tyr Leu Ser Ala Ala Asn Met Leu Tyr Pro Ile Pro Ala Asn Ala Thr
                645                 650                 655

Asn Val Pro Ile Ser Ile Pro Ser Arg Asn Trp Ala Ala Phe Arg Gly
            660                 665                 670

Trp Ala Phe Thr Arg Leu Lys Thr Lys Glu Thr Pro Ser Leu Gly Ser
        675                 680                 685

Gly Tyr Asp Pro Tyr Tyr Thr Tyr Ser Gly Ser Ile Pro Tyr Leu Asp
    690                 695                 700

Gly Thr Phe Tyr Leu Asn His Thr Phe Lys Lys Val Ala Ile Thr Phe
705                 710                 715                 720

Asp Ser Ser Val Ser Trp Pro Gly Asn Asp Arg Leu Leu Thr Pro Asn
                725                 730                 735
```

```
Glu Phe Glu Ile Lys Arg Ser Val Asp Gly Glu Gly Tyr Asn Val Ala
                740                 745                 750

Gln Cys Asn Met Thr Lys Asp Trp Phe Leu Val Gln Met Leu Ala Asn
            755                 760                 765

Tyr Asn Ile Gly Tyr Gln Gly Phe Tyr Ile Pro Glu Ser Tyr Lys Asp
        770                 775                 780

Arg Met Tyr Ser Phe Phe Arg Asn Phe Gln Pro Met Ser Arg Gln Val
785                 790                 795                 800

Val Asp Asp Thr Lys Tyr Lys Asp Tyr Gln Gln Val Gly Ile Leu His
                805                 810                 815

Gln His Asn Asn Ser Gly Phe Val Gly Tyr Leu Ala Pro Thr Met Arg
            820                 825                 830

Glu Gly Gln Ala Tyr Pro Ala Asn Phe Pro Tyr Pro Leu Ile Gly Lys
        835                 840                 845

Thr Ala Val Asp Ser Ile Thr Gln Lys Lys Phe Leu Cys Asp Arg Thr
850                 855                 860

Leu Trp Arg Ile Pro Phe Ser Ser Asn Phe Met Ser Met Gly Ala Leu
865                 870                 875                 880

Thr Asp Leu Gly Gln Asn Leu Leu Tyr Ala Asn Ser Ala His Ala Leu
                885                 890                 895

Asp Met Thr Phe Glu Val Asp Pro Met Asp Glu Pro Thr Leu Leu Tyr
            900                 905                 910

Val Leu Phe Glu Val Phe Asp Val Val Arg Val His Arg Pro His Arg
        915                 920                 925

Gly Val Ile Glu Thr Val Tyr Leu Arg Thr Pro Phe Ser Ala Gly Asn
930                 935                 940

Ala Thr Thr
945

<210> SEQ ID NO 15
<211> LENGTH: 952
<212> TYPE: PRT
<213> ORGANISM: Artificial
<220> FEATURE:
<223> OTHER INFORMATION: Chimeric adenovirus hexon protein Ad5HVR26(1-7)

<400> SEQUENCE: 15

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Glu Thr Tyr Phe Ser Leu Asn Asn Lys Phe Arg Asn Pro
            35                  40                  45

Thr Val Ala Pro Thr His Asp Val Thr Thr Asp Arg Ser Gln Arg Leu
        50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Glu Thr Lys Glu Lys Gln Gly Thr Thr
        130                 135                 140
```

```
Gly Gly Val Gln Gln Glu Lys Asp Val Thr His Val Phe Gly Gln Ala
145                 150                 155                 160

Pro Tyr Ser Gly Ile Asn Ile Thr Lys Glu Gly Ile Gln Ile Gly Thr
            165                 170                 175

Asp Glu Thr Ala Glu Asn Gly Lys Lys Asp Ile Tyr Ala Asp Lys Thr
        180                 185                 190

Phe Gln Pro Glu Pro Gln Ile Gly Glu Ser Gln Trp Gln Glu Asn Glu
    195                 200                 205

Ala Phe Tyr Gly Gly Arg Val Leu Lys Lys Thr Thr Pro Met Lys Pro
210                 215                 220

Cys Tyr Gly Ser Tyr Ala Lys Pro Thr Asn Glu Asn Gly Gly Gln Ala
225                 230                 235                 240

Lys Phe Lys Pro Val Asn Glu Gly Glu Gln Pro Lys Glu Ser Gln Val
                245                 250                 255

Glu Met Gln Phe Phe Asp Val Pro Gly Gly Ser Pro Pro Ala Gly Gly
            260                 265                 270

Ser Gly Glu Glu Tyr Lys Pro Lys Val Val Leu Tyr Ser Glu Asp Val
        275                 280                 285

Asp Ile Glu Thr Pro Asp Thr His Ile Ser Tyr Met Pro Gly Thr Ser
290                 295                 300

Asp Asn Ser Ser Arg Glu Leu Met Gly Gln Gln Ser Met Pro Asn Arg
305                 310                 315                 320

Pro Asn Tyr Ile Ala Phe Arg Asp Asn Phe Ile Gly Leu Met Tyr Tyr
                325                 330                 335

Asn Ser Thr Gly Asn Met Gly Val Leu Ala Gly Gln Ala Ser Gln Leu
            340                 345                 350

Asn Ala Val Val Asp Leu Gln Asp Arg Asn Thr Glu Leu Ser Tyr Gln
        355                 360                 365

Leu Leu Leu Asp Ser Ile Gly Asp Arg Thr Arg Tyr Phe Ser Met Trp
370                 375                 380

Asn Gln Ala Val Asp Ser Tyr Asp Pro Asp Val Arg Ile Ile Glu Asn
385                 390                 395                 400

His Gly Thr Glu Asp Glu Leu Pro Asn Tyr Cys Phe Pro Leu Asn Gly
                405                 410                 415

Thr Gly Thr Asn Ser Thr Tyr Gln Gly Val Lys Ile Thr Asn Gly Asn
            420                 425                 430

Asp Gly Ala Glu Glu Ser Glu Trp Glu Lys Asp Asp Ala Ile Ser Arg
        435                 440                 445

Gln Asn Gln Ile Arg Val Gly Asn Asn Phe Ala Met Glu Ile Asn Leu
450                 455                 460

Asn Ala Asn Leu Trp Arg Asn Phe Leu Tyr Ser Asn Ile Ala Leu Tyr
465                 470                 475                 480

Leu Pro Asp Lys Leu Lys Tyr Ser Pro Ser Asn Val Lys Ile Ser Asp
                485                 490                 495

Asn Pro Asn Thr Tyr Asp Tyr Met Asn Lys Arg Val Val Ala Pro Gly
            500                 505                 510

Leu Val Asp Cys Tyr Ile Asn Leu Gly Ala Arg Trp Ser Leu Asp Tyr
        515                 520                 525

Met Asp Asn Val Asn Pro Phe Asn His His Arg Asn Ala Gly Leu Arg
530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Ile Lys Asn Leu Leu Leu Leu Pro
```

```
                565                 570                 575
Gly Ser Tyr Thr Tyr Glu Trp Asn Phe Arg Lys Asp Val Asn Met Val
            580                 585                 590
Leu Gln Ser Ser Leu Gly Asn Asp Leu Arg Val Asp Gly Ala Ser Ile
            595                 600                 605
Lys Phe Asp Ser Ile Cys Leu Tyr Ala Thr Phe Phe Pro Met Ala His
            610                 615                 620
Asn Thr Ala Ser Thr Leu Glu Ala Met Leu Arg Asn Asp Thr Asn Asp
625                 630                 635                 640
Gln Ser Phe Asn Asp Tyr Leu Ser Ala Ala Asn Met Leu Tyr Pro Ile
                645                 650                 655
Pro Ala Asn Ala Thr Asn Val Pro Ile Ser Ile Pro Ser Arg Asn Trp
            660                 665                 670
Ala Ala Phe Arg Gly Trp Ala Phe Thr Arg Leu Lys Thr Lys Glu Thr
            675                 680                 685
Pro Ser Leu Gly Ser Gly Tyr Asp Pro Tyr Tyr Thr Tyr Ser Gly Ser
            690                 695                 700
Ile Pro Tyr Leu Asp Gly Thr Phe Tyr Leu Asn His Thr Phe Lys Lys
705                 710                 715                 720
Val Ala Ile Thr Phe Asp Ser Ser Val Ser Trp Pro Gly Asn Asp Arg
                725                 730                 735
Leu Leu Thr Pro Asn Glu Phe Glu Ile Lys Arg Ser Val Asp Gly Glu
            740                 745                 750
Gly Tyr Asn Val Ala Gln Cys Asn Met Thr Lys Asp Trp Phe Leu Val
            755                 760                 765
Gln Met Leu Ala Asn Tyr Asn Ile Gly Tyr Gln Gly Phe Tyr Ile Pro
            770                 775                 780
Glu Ser Tyr Lys Asp Arg Met Tyr Ser Phe Phe Arg Asn Phe Gln Pro
785                 790                 795                 800
Met Ser Arg Gln Val Val Asp Asp Thr Lys Tyr Lys Asp Tyr Gln Gln
                805                 810                 815
Val Gly Ile Leu His Gln His Asn Asn Ser Gly Phe Val Gly Tyr Leu
            820                 825                 830
Ala Pro Thr Met Arg Glu Gly Gln Ala Tyr Pro Ala Asn Phe Pro Tyr
            835                 840                 845
Pro Leu Ile Gly Lys Thr Ala Val Asp Ser Ile Thr Gln Lys Lys Phe
            850                 855                 860
Leu Cys Asp Arg Thr Leu Trp Arg Ile Pro Phe Ser Ser Asn Phe Met
865                 870                 875                 880
Ser Met Gly Ala Leu Thr Asp Leu Gly Gln Asn Leu Leu Tyr Ala Asn
                885                 890                 895
Ser Ala His Ala Leu Asp Met Thr Phe Glu Val Asp Pro Met Asp Glu
            900                 905                 910
Pro Thr Leu Leu Tyr Val Leu Phe Glu Val Phe Asp Val Arg Val
            915                 920                 925
His Arg Pro His Arg Gly Val Ile Glu Thr Val Tyr Leu Arg Thr Pro
            930                 935                 940
Phe Ser Ala Gly Asn Ala Thr Thr
945                 950

<210> SEQ ID NO 16
<211> LENGTH: 933
<212> TYPE: PRT
<213> ORGANISM: Artificial
```

-continued

```
<220> FEATURE:
<223> OTHER INFORMATION: Chimeric adenovirus hexon protein
      Ad5HVRPan9(1-7)

<400> SEQUENCE: 16
```

| | | | | | | | | | | | | | | |
|---|---|---|---|---|---|---|---|---|---|---|---|---|---|---|
| Met | Ala | Thr | Pro | Ser | Met | Met | Pro | Gln | Trp | Ser | Tyr | Met | His | Ile | Ser |
| 1 | | | | 5 | | | | | 10 | | | | | 15 | |
| Gly | Gln | Asp | Ala | Ser | Glu | Tyr | Leu | Ser | Pro | Gly | Leu | Val | Gln | Phe | Ala |
| | | | 20 | | | | | 25 | | | | | 30 | | |
| Arg | Ala | Thr | Glu | Thr | Tyr | Phe | Ser | Leu | Asn | Asn | Lys | Phe | Arg | Asn | Pro |
| | | 35 | | | | | 40 | | | | | 45 | | | |
| Thr | Val | Ala | Pro | Thr | His | Asp | Val | Thr | Thr | Asp | Arg | Ser | Gln | Arg | Leu |
| 50 | | | | | 55 | | | | | 60 | | | | | |
| Thr | Leu | Arg | Phe | Ile | Pro | Val | Asp | Arg | Glu | Asp | Thr | Ala | Tyr | Ser | Tyr |
| 65 | | | | | 70 | | | | | 75 | | | | | 80 |
| Lys | Ala | Arg | Phe | Thr | Leu | Ala | Val | Gly | Asp | Asn | Arg | Val | Leu | Asp | Met |
| | | | | 85 | | | | | 90 | | | | | 95 | |
| Ala | Ser | Thr | Tyr | Phe | Asp | Ile | Arg | Gly | Val | Leu | Asp | Arg | Gly | Pro | Thr |
| | | | 100 | | | | | 105 | | | | | 110 | | |
| Phe | Lys | Pro | Tyr | Ser | Gly | Thr | Ala | Tyr | Asn | Ala | Leu | Ala | Pro | Lys | Gly |
| | | 115 | | | | | 120 | | | | | 125 | | | |
| Ala | Pro | Asn | Pro | Cys | Glu | Trp | Thr | Tyr | Lys | Ala | Asp | Gly | Glu | Thr | Ala |
| 130 | | | | | 135 | | | | | 140 | | | | | |
| Thr | Glu | Lys | Thr | His | Val | Phe | Gly | Gln | Ala | Pro | Tyr | Ser | Gly | Ile | Asn |
| 145 | | | | | 150 | | | | | 155 | | | | | 160 |
| Ile | Thr | Lys | Glu | Gly | Ile | Gln | Ile | Gly | Thr | Asp | Thr | Asp | Asp | Gln | Pro |
| | | | | 165 | | | | | 170 | | | | | 175 | |
| Ile | Tyr | Ala | Asp | Lys | Thr | Phe | Gln | Pro | Glu | Pro | Gln | Ile | Gly | Glu | Ser |
| | | | 180 | | | | | 185 | | | | | 190 | | |
| Gln | Trp | His | Asp | Ile | Thr | Gly | Thr | Asp | Glu | Lys | Tyr | Gly | Gly | Arg | Val |
| | | 195 | | | | | 200 | | | | | 205 | | | |
| Leu | Lys | Lys | Thr | Thr | Pro | Met | Lys | Pro | Cys | Tyr | Gly | Ser | Tyr | Ala | Lys |
| 210 | | | | | 215 | | | | | 220 | | | | | |
| Pro | Thr | Asn | Glu | Asn | Gly | Gly | Gln | Ala | Asn | Val | Lys | Thr | Gly | Thr | Gly |
| 225 | | | | | 230 | | | | | 235 | | | | | 240 |
| Thr | Thr | Lys | Glu | Ser | Gln | Val | Glu | Met | Gln | Phe | Phe | Asp | Asn | Arg | Ser |
| | | | | 245 | | | | | 250 | | | | | 255 | |
| Ala | Ala | Ala | Ala | Gly | Leu | Ala | Pro | Lys | Val | Val | Leu | Tyr | Ser | Glu | Asp |
| | | | 260 | | | | | 265 | | | | | 270 | | |
| Val | Asp | Ile | Glu | Thr | Pro | Asp | Thr | His | Ile | Ser | Tyr | Met | Pro | Gly | Thr |
| | | 275 | | | | | 280 | | | | | 285 | | | |
| Asp | Asp | Ser | Ser | Ser | Arg | Glu | Leu | Met | Gly | Gln | Ser | Met | Pro | Asn |
| 290 | | | | | 295 | | | | | 300 | | | | | |
| Arg | Pro | Asn | Tyr | Ile | Ala | Phe | Arg | Asp | Asn | Phe | Ile | Gly | Leu | Met | Tyr |
| 305 | | | | | 310 | | | | | 315 | | | | | 320 |
| Tyr | Asn | Ser | Thr | Gly | Asn | Met | Gly | Val | Leu | Ala | Gly | Gln | Ala | Ser | Gln |
| | | | | 325 | | | | | 330 | | | | | 335 | |
| Leu | Asn | Ala | Val | Val | Asp | Leu | Gln | Asp | Arg | Asn | Thr | Glu | Leu | Ser | Tyr |
| | | | 340 | | | | | 345 | | | | | 350 | | |
| Gln | Leu | Leu | Leu | Asp | Ser | Ile | Gly | Asp | Arg | Thr | Arg | Tyr | Phe | Ser | Met |
| | | 355 | | | | | 360 | | | | | 365 | | | |
| Trp | Asn | Gln | Ala | Val | Asp | Ser | Tyr | Asp | Pro | Asp | Val | Arg | Ile | Ile | Glu |
| 370 | | | | | 375 | | | | | 380 | | | | | |
| Asn | His | Gly | Thr | Glu | Asp | Glu | Leu | Pro | Asn | Tyr | Cys | Phe | Pro | Leu | Asp |

```
385                 390                 395                 400
Ala Val Gly Arg Thr Asp Thr Tyr Gln Gly Ile Lys Ala Asn Gly Thr
                405                 410                 415

Asp Gln Thr Thr Trp Thr Lys Asp Asp Ser Val Asn Asp Ala Asn Glu
            420                 425                 430

Ile Arg Val Gly Asn Asn Phe Ala Met Glu Ile Asn Leu Asn Ala Asn
            435                 440                 445

Leu Trp Arg Asn Phe Leu Tyr Ser Asn Ile Ala Leu Tyr Leu Pro Asp
        450                 455                 460

Lys Leu Lys Tyr Ser Pro Ser Asn Val Lys Ile Ser Asp Asn Pro Asn
465                 470                 475                 480

Thr Tyr Asp Tyr Met Asn Lys Arg Val Ala Pro Gly Leu Val Asp
                485                 490                 495

Cys Tyr Ile Asn Leu Gly Ala Arg Trp Ser Leu Asp Tyr Met Asp Asn
                500                 505                 510

Val Asn Pro Phe Asn His His Arg Asn Ala Gly Leu Arg Tyr Arg Ser
            515                 520                 525

Met Leu Leu Gly Asn Gly Arg Tyr Val Pro Phe His Ile Gln Val Pro
        530                 535                 540

Gln Lys Phe Phe Ala Ile Lys Asn Leu Leu Leu Pro Gly Ser Tyr
545                 550                 555                 560

Thr Tyr Glu Trp Asn Phe Arg Lys Asp Val Asn Met Val Leu Gln Ser
                565                 570                 575

Ser Leu Gly Asn Asp Leu Arg Val Asp Gly Ala Ser Ile Lys Phe Asp
            580                 585                 590

Ser Ile Cys Leu Tyr Ala Thr Phe Phe Pro Met Ala His Asn Thr Ala
            595                 600                 605

Ser Thr Leu Glu Ala Met Leu Arg Asn Asp Thr Asn Asp Gln Ser Phe
        610                 615                 620

Asn Asp Tyr Leu Ser Ala Ala Asn Met Leu Tyr Pro Ile Pro Ala Asn
625                 630                 635                 640

Ala Thr Asn Val Pro Ile Ser Ile Pro Ser Arg Asn Trp Ala Ala Phe
                645                 650                 655

Arg Gly Trp Ala Phe Thr Arg Leu Lys Thr Lys Glu Thr Pro Ser Leu
                660                 665                 670

Gly Ser Gly Tyr Asp Pro Tyr Tyr Thr Tyr Ser Gly Ser Ile Pro Tyr
            675                 680                 685

Leu Asp Gly Thr Phe Tyr Leu Asn His Thr Phe Lys Lys Val Ala Ile
        690                 695                 700

Thr Phe Asp Ser Ser Val Ser Trp Pro Gly Asn Asp Arg Leu Leu Thr
705                 710                 715                 720

Pro Asn Glu Phe Glu Ile Lys Arg Ser Val Asp Gly Glu Gly Tyr Asn
                725                 730                 735

Val Ala Gln Cys Asn Met Thr Lys Asp Trp Phe Leu Val Gln Met Leu
            740                 745                 750

Ala Asn Tyr Asn Ile Gly Tyr Gln Gly Phe Tyr Ile Pro Glu Ser Tyr
            755                 760                 765

Lys Asp Arg Met Tyr Ser Phe Phe Arg Asn Phe Gln Pro Met Ser Arg
        770                 775                 780

Gln Val Val Asp Asp Thr Lys Tyr Lys Asp Tyr Gln Gln Val Gly Ile
785                 790                 795                 800

Leu His Gln His Asn Asn Ser Gly Phe Val Gly Tyr Leu Ala Pro Thr
                805                 810                 815
```

```
Met Arg Glu Gly Gln Ala Tyr Pro Ala Asn Phe Pro Tyr Pro Leu Ile
                820                 825                 830

Gly Lys Thr Ala Val Asp Ser Ile Thr Gln Lys Lys Phe Leu Cys Asp
            835                 840                 845

Arg Thr Leu Trp Arg Ile Pro Phe Ser Ser Asn Phe Met Ser Met Gly
        850                 855                 860

Ala Leu Thr Asp Leu Gly Gln Asn Leu Leu Tyr Ala Asn Ser Ala His
865                 870                 875                 880

Ala Leu Asp Met Thr Phe Glu Val Asp Pro Met Asp Glu Pro Thr Leu
                885                 890                 895

Leu Tyr Val Leu Phe Glu Val Phe Asp Val Val Arg Val His Arg Pro
            900                 905                 910

His Arg Gly Val Ile Glu Thr Val Tyr Leu Arg Thr Pro Phe Ser Ala
        915                 920                 925

Gly Asn Ala Thr Thr
    930

<210> SEQ ID NO 17
<211> LENGTH: 30
<212> TYPE: PRT
<213> ORGANISM: Adenovirus serotype 5

<400> SEQUENCE: 17

Asp Glu Ala Ala Thr Ala Leu Glu Ile Asn Leu Glu Glu Glu Asp Asp
1               5                   10                  15

Asp Asn Glu Asp Glu Val Asp Glu Gln Ala Glu Gln Gln Lys
            20                  25                  30

<210> SEQ ID NO 18
<211> LENGTH: 7
<212> TYPE: PRT
<213> ORGANISM: Adenovirus serotype 5

<400> SEQUENCE: 18

Val Glu Gly Gln Thr Pro Lys
1               5

<210> SEQ ID NO 19
<211> LENGTH: 9
<212> TYPE: PRT
<213> ORGANISM: Adenovirus serotype 5

<400> SEQUENCE: 19

Tyr Glu Thr Glu Ile Asn His Ala Ala
1               5

<210> SEQ ID NO 20
<211> LENGTH: 11
<212> TYPE: PRT
<213> ORGANISM: Adenovirus serotype 5

<400> SEQUENCE: 20

Gly Ile Leu Val Lys Gln Gln Asn Gly Lys Leu
1               5                   10

<210> SEQ ID NO 21
<211> LENGTH: 14
<212> TYPE: PRT
<213> ORGANISM: Adenovirus serotype 5

<400> SEQUENCE: 21
```

```
Ser Thr Thr Glu Ala Thr Ala Gly Asn Gly Asp Asn Leu Thr
1               5                   10

<210> SEQ ID NO 22
<211> LENGTH: 6
<212> TYPE: PRT
<213> ORGANISM: Adenovirus serotype 5

<400> SEQUENCE: 22

Thr Ile Lys Glu Gly Asn
1               5

<210> SEQ ID NO 23
<211> LENGTH: 34
<212> TYPE: PRT
<213> ORGANISM: Adenovirus serotype 5

<400> SEQUENCE: 23

Gly Gly Val Ile Asn Thr Glu Thr Leu Thr Lys Val Lys Pro Lys Thr
1               5                   10                  15

Gly Gln Glu Asn Gly Trp Glu Lys Asp Ala Thr Glu Phe Ser Asp Lys
            20                  25                  30

Asn Glu

<210> SEQ ID NO 24
<211> LENGTH: 15
<212> TYPE: PRT
<213> ORGANISM: Adenovirus serotype 48

<400> SEQUENCE: 24

Glu Glu Lys Lys Asn Gly Gly Gly Ser Asp Ala Asn Gln Met Gln
1               5                   10                  15

<210> SEQ ID NO 25
<211> LENGTH: 13
<212> TYPE: PRT
<213> ORGANISM: Adenovirus serotype 48

<400> SEQUENCE: 25

Ile Asp Ala Thr Lys Glu Glu Asp Asn Gly Lys Glu Ile
1               5                   10

<210> SEQ ID NO 26
<211> LENGTH: 8
<212> TYPE: PRT
<213> ORGANISM: Adenovirus serotype 48

<400> SEQUENCE: 26

Gln Asp Ser Asp Asn Tyr Tyr Gly
1               5

<210> SEQ ID NO 27
<211> LENGTH: 14
<212> TYPE: PRT
<213> ORGANISM: Adenovirus serotype 48

<400> SEQUENCE: 27

Ala Lys Phe Lys Thr Pro Glu Lys Glu Gly Glu Glu Pro Lys
1               5                   10

<210> SEQ ID NO 28
<211> LENGTH: 17
<212> TYPE: PRT
```

-continued

<213> ORGANISM: Adenovirus serotype 48

<400> SEQUENCE: 28

Asp Ile Pro Ser Thr Gly Thr Gly Gly Asn Gly Thr Asn Val Asn Phe
1               5                   10                  15
Lys

<210> SEQ ID NO 29
<211> LENGTH: 6
<212> TYPE: PRT
<213> ORGANISM: Adenovirus serotype 48

<400> SEQUENCE: 29

Gly Lys Glu Asp Ala Ser
1               5

<210> SEQ ID NO 30
<211> LENGTH: 33
<212> TYPE: PRT
<213> ORGANISM: Adenovirus serotype 48

<400> SEQUENCE: 30

Asp Gly Ala Gly Thr Asn Ala Val Tyr Gln Gly Val Lys Val Lys Thr
1               5                   10                  15

Thr Asn Asn Thr Glu Trp Glu Lys Asp Thr Ala Val Ser Glu His Asn
            20                  25                  30
Gln

<210> SEQ ID NO 31
<211> LENGTH: 25
<212> TYPE: PRT
<213> ORGANISM: Adenovirus serotype 35

<400> SEQUENCE: 31

Ile Ala Lys Gly Val Pro Thr Ala Ala Ala Gly Asn Gly Glu Glu
1               5                   10                  15

Glu His Glu Thr Glu Glu Lys Thr Ala
            20                  25

<210> SEQ ID NO 32
<211> LENGTH: 12
<212> TYPE: PRT
<213> ORGANISM: Adenovirus serotype 35

<400> SEQUENCE: 32

Leu Glu Ile Ser Ala Glu Asn Glu Ser Lys Pro Ile
1               5                   10

<210> SEQ ID NO 33
<211> LENGTH: 11
<212> TYPE: PRT
<213> ORGANISM: Adenovirus serotype 35

<400> SEQUENCE: 33

Thr Asp Leu Asp Gly Lys Thr Glu Glu Tyr Gly
1               5                   10

<210> SEQ ID NO 34
<211> LENGTH: 13
<212> TYPE: PRT
<213> ORGANISM: Adenovirus serotype 35

<400> SEQUENCE: 34

```
Ala Lys Pro Lys Asn Ser Glu Pro Ser Ser Glu Lys Ile
1               5                   10

<210> SEQ ID NO 35
<211> LENGTH: 10
<212> TYPE: PRT
<213> ORGANISM: Adenovirus serotype 35

<400> SEQUENCE: 35

Asp Asn Ser Ser Gln Arg Thr Asn Phe Ser
1               5                   10

<210> SEQ ID NO 36
<211> LENGTH: 6
<212> TYPE: PRT
<213> ORGANISM: Adenovirus serotype 35

<400> SEQUENCE: 36

Gly Thr Glu Asp Thr Ser
1               5

<210> SEQ ID NO 37
<211> LENGTH: 33
<212> TYPE: PRT
<213> ORGANISM: Adenovirus serotype 35

<400> SEQUENCE: 37

Asp Gly Ile Gly Val Pro Thr Thr Ser Tyr Lys Ser Ile Val Pro Asn
1               5                   10                  15

Gly Glu Asp Asn Asn Trp Lys Glu Pro Glu Val Asn Gly Thr Ser
            20                  25                  30

Glu

<210> SEQ ID NO 38
<211> LENGTH: 22
<212> TYPE: PRT
<213> ORGANISM: Adenovirus serotype 11

<400> SEQUENCE: 38

Ile Ala Glu Gly Val Lys Asn Thr Thr Gly Glu Glu His Val Thr Glu
1               5                   10                  15

Glu Glu Thr Asn Thr Thr
            20

<210> SEQ ID NO 39
<211> LENGTH: 11
<212> TYPE: PRT
<213> ORGANISM: Adenovirus serotype 11

<400> SEQUENCE: 39

Leu Glu Val Ser Asp Glu Glu Ser Lys Pro Ile
1               5                   10

<210> SEQ ID NO 40
<211> LENGTH: 11
<212> TYPE: PRT
<213> ORGANISM: Adenovirus serotype 11

<400> SEQUENCE: 40

Thr Asp Leu Asp Gly Lys Thr Glu Lys Tyr Gly
1               5                   10
```

```
<210> SEQ ID NO 41
<211> LENGTH: 13
<212> TYPE: PRT
<213> ORGANISM: Adenovirus serotype 11

<400> SEQUENCE: 41

Ala Lys Gln Lys Thr Thr Glu Gln Pro Asn Gln Lys Val
1               5                   10

<210> SEQ ID NO 42
<211> LENGTH: 10
<212> TYPE: PRT
<213> ORGANISM: Adenovirus serotype 11

<400> SEQUENCE: 42

Asp Ala Ala Ser Gln Lys Thr Asn Leu Ser
1               5                   10

<210> SEQ ID NO 43
<211> LENGTH: 6
<212> TYPE: PRT
<213> ORGANISM: Adenovirus serotype 11

<400> SEQUENCE: 43

Gly Thr Glu Asp Thr Ser
1               5

<210> SEQ ID NO 44
<211> LENGTH: 33
<212> TYPE: PRT
<213> ORGANISM: Adenovirus serotype 11

<400> SEQUENCE: 44

Asp Gly Ile Gly Val Pro Thr Thr Ser Tyr Lys Ser Ile Val Pro Asn
1               5                   10                  15

Gly Asp Asn Ala Pro Asn Trp Lys Glu Pro Glu Val Asn Gly Thr Ser
            20                  25                  30

Glu

<210> SEQ ID NO 45
<211> LENGTH: 18
<212> TYPE: PRT
<213> ORGANISM: Adenovirus serotype 26

<400> SEQUENCE: 45

Glu Thr Lys Glu Lys Gln Gly Thr Gly Gly Val Gln Gln Glu Lys
1               5                   10                  15

Asp Val

<210> SEQ ID NO 46
<211> LENGTH: 12
<212> TYPE: PRT
<213> ORGANISM: Adenovirus serotype 26

<400> SEQUENCE: 46

Thr Asp Glu Thr Ala Glu Asn Gly Lys Lys Asp Ile
1               5                   10

<210> SEQ ID NO 47
<211> LENGTH: 8
<212> TYPE: PRT
<213> ORGANISM: Adenovirus serotype 26

<400> SEQUENCE: 47
```

-continued

Gln Glu Asn Glu Ala Phe Tyr Gly
1               5

<210> SEQ ID NO 48
<211> LENGTH: 13
<212> TYPE: PRT
<213> ORGANISM: Adenovirus serotype 26

<400> SEQUENCE: 48

Ala Lys Phe Lys Pro Val Asn Glu Gly Glu Gln Pro Lys
1               5                   10

<210> SEQ ID NO 49
<211> LENGTH: 17
<212> TYPE: PRT
<213> ORGANISM: Adenovirus serotype 26

<400> SEQUENCE: 49

Asp Val Pro Gly Gly Ser Pro Pro Ala Gly Gly Ser Gly Glu Glu Tyr
1               5                   10                  15

Lys

<210> SEQ ID NO 50
<211> LENGTH: 6
<212> TYPE: PRT
<213> ORGANISM: Adenovirus serotype 26

<400> SEQUENCE: 50

Gly Thr Ser Asp Asn Ser
1               5

<210> SEQ ID NO 51
<211> LENGTH: 37
<212> TYPE: PRT
<213> ORGANISM: Adenovirus serotype 26

<400> SEQUENCE: 51

Asn Gly Thr Gly Thr Asn Ser Thr Tyr Gln Gly Val Lys Ile Thr Asn
1               5                   10                  15

Gly Asn Asp Gly Ala Glu Glu Ser Glu Trp Glu Lys Asp Asp Ala Ile
            20                  25                  30

Ser Arg Gln Asn Gln
        35

<210> SEQ ID NO 52
<211> LENGTH: 12
<212> TYPE: PRT
<213> ORGANISM: Adenovirus serotype pan9

<400> SEQUENCE: 52

Thr Tyr Lys Ala Asp Gly Glu Thr Ala Thr Glu Lys
1               5                   10

<210> SEQ ID NO 53
<211> LENGTH: 8
<212> TYPE: PRT
<213> ORGANISM: Adenovirus serotype pan9

<400> SEQUENCE: 53

Thr Asp Thr Asp Asp Gln Pro Ile
1               5

<210> SEQ ID NO 54
<211> LENGTH: 11
<212> TYPE: PRT
<213> ORGANISM: Adenovirus serotype pan9

<400> SEQUENCE: 54

His Asp Ile Thr Gly Thr Asp Glu Lys Tyr Gly
1               5                   10

<210> SEQ ID NO 55
<211> LENGTH: 11
<212> TYPE: PRT
<213> ORGANISM: Adenovirus serotype pan9

<400> SEQUENCE: 55

Ala Asn Val Lys Thr Gly Thr Gly Thr Thr Lys
1               5                   10

<210> SEQ ID NO 56
<211> LENGTH: 11
<212> TYPE: PRT
<213> ORGANISM: Adenovirus serotype pan9

<400> SEQUENCE: 56

Asp Asn Arg Ser Ala Ala Ala Ala Gly Leu Ala
1               5                   10

<210> SEQ ID NO 57
<211> LENGTH: 6
<212> TYPE: PRT
<213> ORGANISM: Adenovirus serotype pan9

<400> SEQUENCE: 57

Gly Thr Asp Asp Ser Ser
1               5

<210> SEQ ID NO 58
<211> LENGTH: 33
<212> TYPE: PRT
<213> ORGANISM: Adenovirus serotype pan9

<400> SEQUENCE: 58

Asp Ala Val Gly Arg Thr Asp Thr Tyr Gln Gly Ile Lys Ala Asn Gly
1               5                   10                  15

Thr Asp Gln Thr Thr Trp Thr Lys Asp Asp Ser Val Asn Asp Ala Asn
            20                  25                  30

Glu

<210> SEQ ID NO 59
<211> LENGTH: 11
<212> TYPE: PRT
<213> ORGANISM: Adenovirus serotype 34

<400> SEQUENCE: 59

Leu Glu Val Ser Thr Glu Gly Pro Lys Pro Ile
1               5                   10

<210> SEQ ID NO 60
<211> LENGTH: 25
<212> TYPE: PRT
<213> ORGANISM: Adenovirus serotype 34

<400> SEQUENCE: 60

Leu Asp Lys Gly Val Thr Ser Thr Gly Leu Val Asp Asp Gly Asn Thr

```
                1               5                  10                 15

Asp Asp Gly Glu Glu Ala Lys Lys Ala
                20                  25

<210> SEQ ID NO 61
<211> LENGTH: 11
<212> TYPE: PRT
<213> ORGANISM: Adenovirus serotype 34

<400> SEQUENCE: 61

Thr Asp Leu Asp Gly Lys Thr Glu Glu Tyr Gly
1               5                   10

<210> SEQ ID NO 62
<211> LENGTH: 14
<212> TYPE: PRT
<213> ORGANISM: Adenovirus serotype 34

<400> SEQUENCE: 62

Ala Lys Val Lys Pro Lys Glu Asp Asp Gly Thr Asn Asn Ile
1               5                   10

<210> SEQ ID NO 63
<211> LENGTH: 10
<212> TYPE: PRT
<213> ORGANISM: Adenovirus serotype 34

<400> SEQUENCE: 63

Asp Leu Arg Ser Gln Arg Ser Glu Leu Lys
1               5                   10

<210> SEQ ID NO 64
<211> LENGTH: 6
<212> TYPE: PRT
<213> ORGANISM: Adenovirus serotype 34

<400> SEQUENCE: 64

Gly Val Ser Asp Ala Ser
1               5

<210> SEQ ID NO 65
<211> LENGTH: 32
<212> TYPE: PRT
<213> ORGANISM: Adenovirus serotype 34

<400> SEQUENCE: 65

Asp Gly Val Gly Pro Arg Thr Asp Ser Tyr Lys Glu Ile Lys Pro Asn
1               5                   10                  15

Gly Asp Gln Ser Thr Trp Thr Asn Val Asp Pro Thr Gly Ser Ser Glu
                20                  25                  30

<210> SEQ ID NO 66
<211> LENGTH: 12
<212> TYPE: PRT
<213> ORGANISM: Adenovirus serotype 49

<400> SEQUENCE: 66

Asp Ala Lys Glu Asn Asn Gly Gln Gly Glu Ala Lys
1               5                   10

<210> SEQ ID NO 67
<211> LENGTH: 14
<212> TYPE: PRT
<213> ORGANISM: Adenovirus serotype 49
```

-continued

<400> SEQUENCE: 67

Ile Asp Glu Asn Lys Glu Glu Asp Glu Gly Arg Glu Ile
1               5                   10

<210> SEQ ID NO 68
<211> LENGTH: 8
<212> TYPE: PRT
<213> ORGANISM: Adenovirus serotype 49

<400> SEQUENCE: 68

Gln Asn Thr Glu Asn Phe Tyr Gly
1               5

<210> SEQ ID NO 69
<211> LENGTH: 13
<212> TYPE: PRT
<213> ORGANISM: Adenovirus serotype 49

<400> SEQUENCE: 69

Ala Val Phe Lys Thr Gly Glu Asn Gly Lys Pro Thr Glu
1               5                   10

<210> SEQ ID NO 70
<211> LENGTH: 13
<212> TYPE: PRT
<213> ORGANISM: Adenovirus serotype 49

<400> SEQUENCE: 70

Asp Leu Arg Gln Asn Asp Thr Gly Gly Asn Asn Asn Gln
1               5                   10

<210> SEQ ID NO 71
<211> LENGTH: 6
<212> TYPE: PRT
<213> ORGANISM: Adenovirus serotype 49

<400> SEQUENCE: 71

Gly Thr Ser Asp Asp Ser
1               5

<210> SEQ ID NO 72
<211> LENGTH: 36
<212> TYPE: PRT
<213> ORGANISM: Adenovirus serotype 49

<400> SEQUENCE: 72

Asp Gly Ser Gly Ser Ser Thr Ala Tyr Gln Gly Val Glu Pro Asp Thr
1               5                   10                  15

Thr Val Ala Gly Thr Asn Asp Lys Trp Lys Val Asn Ala Lys Val Ala
            20                  25                  30

Gln His Asn Gln
        35

<210> SEQ ID NO 73
<211> LENGTH: 15
<212> TYPE: PRT
<213> ORGANISM: Adenovirus serotype 50

<400> SEQUENCE: 73

Leu Asn Lys Gly Asp Glu Glu Asp Gly Glu Asp Asp Gln Gln Ala
1               5                   10                  15

<210> SEQ ID NO 74
<211> LENGTH: 12
<212> TYPE: PRT
<213> ORGANISM: Adenovirus serotype 50

<400> SEQUENCE: 74

Leu Glu Val Pro Ser Glu Gly Gly Pro Lys Pro Ile
1               5                   10

<210> SEQ ID NO 75
<211> LENGTH: 11
<212> TYPE: PRT
<213> ORGANISM: Adenovirus serotype 50

<400> SEQUENCE: 75

Thr Asp Thr Asp Gly Thr Asp Glu Lys Tyr Gly
1               5                   10

<210> SEQ ID NO 76
<211> LENGTH: 11
<212> TYPE: PRT
<213> ORGANISM: Adenovirus serotype 50

<400> SEQUENCE: 76

Ala Lys Val Lys Lys Glu Glu Glu Gly Lys Val
1               5                   10

<210> SEQ ID NO 77
<211> LENGTH: 10
<212> TYPE: PRT
<213> ORGANISM: Adenovirus serotype 50

<400> SEQUENCE: 77

Asp Leu Arg Ser Gln Met Thr Gly Leu Lys
1               5                   10

<210> SEQ ID NO 78
<211> LENGTH: 6
<212> TYPE: PRT
<213> ORGANISM: Adenovirus serotype 50

<400> SEQUENCE: 78

Gly Ala Ser Asp Ala Ser
1               5

<210> SEQ ID NO 79
<211> LENGTH: 33
<212> TYPE: PRT
<213> ORGANISM: Adenovirus serotype 50

<400> SEQUENCE: 79

Asp Gly Val Gly Pro Arg Ile Asp Ser Tyr Lys Gly Ile Glu Thr Asn
1               5                   10                  15

Gly Asp Glu Thr Thr Thr Trp Lys Asp Leu Glu Pro Lys Gly Ile Ser
            20                  25                  30

Glu

<210> SEQ ID NO 80
<211> LENGTH: 960
<212> TYPE: DNA
<213> ORGANISM: Artificial
<220> FEATURE:
<223> OTHER INFORMATION: Nucleic acid encoding chimeric Ad35k26 fiber
      protein

```
<400> SEQUENCE: 80
atgaccaaga gagtccggct cagtgactcc ttcaaccctg tctacccgta cgaagatgaa        60
agcacctccc aacacccctt tataaaccca gggtttattt ccccaaatgg cttcacacaa       120
agcccagacg gagttcttac tttaaaatgt ttaaccccac taacaaccac aggcggatct       180
ctacagctaa aagtgggagg gggacttaca gtggatgaca ctgatggtac cttacaagaa       240
aacatacgtg ctacagcacc cattactaaa aataatcact ctgtagaact atccattgga       300
aatggattag aaactcaaaa caataaacta tgtgccaaat gggaaatgg gttaaaattt        360 aacaacggtg acatttgtat aaaggatagt attaacaccc tgtggacaac ccctgacaca       420
tctccaaatt gcaaaatgag tacagaaaag gattctaaac ttacgttgac acttacaaag       480
tgtggaagtc aggttctggg aaatgtatct ttacttgcag ttacaggtga atatcatcaa       540
atgactgcta ctacaaagaa ggatgtaaaa atatctttac tatttgatga aatggaatt        600 ctattaccat cttcgtccct tagcaaagat tattggaatt acagaagtga tgattctatt       660
gtatctcaaa aatataataa tgcagttcca ttcatgccaa acctgacagc ttatccaaaa       720
ccaagcgctc aaaatgcaaa aaactattca agaactaaaa tcataagtaa tgtctactta       780
ggtgctctta cctaccaacc tgtaattatc actattgcat ttaatcagga aactgaaaat       840
ggatgtgctt attctataac atttaccttc acttggcaaa agactattc tgcccaacag       900 tttgatgtta catcttttac cttctcatat cttacccaag agaacaaaga caaagactaa       960

<210> SEQ ID NO 81
<211> LENGTH: 319
<212> TYPE: PRT
<213> ORGANISM: Artificial
<220> FEATURE:
<223> OTHER INFORMATION: Chimeric Ad35k26 fiber protein

<400> SEQUENCE: 81

Met Thr Lys Arg Val Arg Leu Ser Asp Ser Phe Asn Pro Val Tyr Pro
1               5                   10                  15

Tyr Glu Asp Glu Ser Thr Ser Gln His Pro Phe Ile Asn Pro Gly Phe
            20                  25                  30

Ile Ser Pro Asn Gly Phe Thr Gln Ser Pro Asp Gly Val Leu Thr Leu
        35                  40                  45

Lys Cys Leu Thr Pro Leu Thr Thr Gly Gly Ser Leu Gln Leu Lys
    50                  55                  60

Val Gly Gly Gly Leu Thr Val Asp Asp Thr Asp Gly Thr Leu Gln Glu
65                  70                  75                  80

Asn Ile Arg Ala Thr Ala Pro Ile Thr Lys Asn Asn His Ser Val Glu
                85                  90                  95

Leu Ser Ile Gly Asn Gly Leu Glu Thr Gln Asn Asn Lys Leu Cys Ala
            100                 105                 110

Lys Leu Gly Asn Gly Leu Lys Phe Asn Asn Gly Asp Ile Cys Ile Lys
        115                 120                 125

Asp Ser Ile Asn Thr Leu Trp Thr Thr Pro Asp Thr Ser Pro Asn Cys
    130                 135                 140

Lys Met Ser Thr Glu Lys Asp Ser Lys Leu Thr Leu Thr Leu Thr Lys
145                 150                 155                 160

Cys Gly Ser Gln Val Leu Gly Asn Val Ser Leu Leu Ala Val Thr Gly
                165                 170                 175

Glu Tyr His Gln Met Thr Ala Thr Thr Lys Lys Asp Val Lys Ile Ser
            180                 185                 190
```

Leu Leu Phe Asp Glu Asn Gly Ile Leu Leu Pro Ser Ser Ser Leu Ser
        195                 200                 205

Lys Asp Tyr Trp Asn Tyr Arg Ser Asp Asp Ser Ile Val Ser Gln Lys
    210                 215                 220

Tyr Asn Asn Ala Val Pro Phe Met Pro Asn Leu Thr Ala Tyr Pro Lys
225                 230                 235                 240

Pro Ser Ala Gln Asn Ala Lys Asn Tyr Ser Arg Thr Lys Ile Ile Ser
                245                 250                 255

Asn Val Tyr Leu Gly Ala Leu Thr Tyr Gln Pro Val Ile Ile Thr Ile
            260                 265                 270

Ala Phe Asn Gln Glu Thr Glu Asn Gly Cys Ala Tyr Ser Ile Thr Phe
        275                 280                 285

Thr Phe Thr Trp Gln Lys Asp Tyr Ser Ala Gln Gln Phe Asp Val Thr
    290                 295                 300

Ser Phe Thr Phe Ser Tyr Leu Thr Gln Glu Asn Lys Asp Lys Asp
305                 310                 315

<210> SEQ ID NO 82
<211> LENGTH: 996
<212> TYPE: DNA
<213> ORGANISM: Artificial
<220> FEATURE:
<223> OTHER INFORMATION: Nucleic acid encoding chimeric Ad35k49 fiber
      protein

<400> SEQUENCE: 82
atgaccaaga gagtccggct cagtgactcc ttcaaccctg tctacccgta cgaagatgaa      60
agcacctccc aacaccccu tataaaccca gggtttattt ccccaaatgg cttcacacaa     120
agcccagacg gagttcttac tttaaaatgt ttaaccccac taacaaccac aggcggatct     180
ctacagctaa aagtgggagg gggacttaca gtggatgaca ctgatggtac cttacaagaa     240
aacatacgtg ctacagcacc cattactaaa ataatcact ctgtagaact atccattgga      300
aatggattag aaactcaaaa caataaacta tgtgccaaat tgggaaatgg gttaaaattt     360
aacaacggtg acatttgtat aaaggatagt attaacaccc tttggacaac tccagaccca     420
tctccaaact gcaaagtttc agaagagaag gattccaagc ttactctagt tttaacaaag     480
tgcggaagtc agattctggc cagtgtatca ttgcttgttg ttaaagggaa gtttgccaat     540
attaacaata aaacaaaccc aggcgaggac tataaaaaat tttcagttaa attattgttt     600
gatgccaatg gtaaattatt gacaggatca agcctagatg gaaattattg gaattataaa     660
aacaaggata gtgtgattgg gtctccttat gaaaatgccg ttcctttat gcctaattcc     720 acagcttatc ctaaaatcat caataatgga acagctaatc ctgaagataa aaaaagtgca     780
gccaaaaaaa ctattgtcac taatgtgtac ctaggggag atgcagctaa acccgtggct     840
accactatta gtttcaacaa agaaactgaa tctaattgtg tttattctat aacctttgac     900
tttgcttgga caaaactta caaaaatgtt ccatttgatt catcttcgct aacattttca     960
tatattgccc aagatgccga agacaaaaac gaataa                               996

<210> SEQ ID NO 83
<211> LENGTH: 916
<212> TYPE: PRT
<213> ORGANISM: Artificial
<220> FEATURE:
<223> OTHER INFORMATION: Chimeric Ad5HVR35(1-7)* chimeric hexon protein

<400> SEQUENCE: 83

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Glu Thr Tyr Phe Ser Leu Asn Asn Lys Phe Arg Asn Pro
            35                  40                  45

Thr Val Ala Pro Thr His Asp Val Thr Thr Asp Arg Ser Gln Arg Leu
50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
                100                 105                 110

Phe Lys Pro Tyr Ser Gly Thr Ala Tyr Asn Ala Leu Ala Pro Lys Gly
            115                 120                 125

Ala Pro Asn Pro Cys Glu Trp Asp Thr His Val Phe Gly Gln Ala Pro
130                 135                 140

Tyr Ser Gly Ile Asn Ile Thr Lys Glu Gly Ile Gln Ile Gly Gln Gly
145                 150                 155                 160

Lys Tyr Ala Asp Lys Thr Phe Gln Pro Glu Pro Gln Ile Gly Glu Ser
                165                 170                 175

Gln Trp Tyr Asp Leu Asp Ile Asn His Ala Ala Gly Arg Val Leu Lys
                180                 185                 190

Lys Thr Thr Pro Met Lys Pro Cys Tyr Gly Ser Tyr Ala Lys Pro Thr
            195                 200                 205

Asn Glu Asn Gly Gly Gln Gly Ile Leu Val Lys Asn Ser Glu Pro Ser
            210                 215                 220

Ser Glu Lys Ile Glu Ser Gln Val Glu Met Gln Phe Phe Ser Asn Ser
225                 230                 235                 240

Ser Gln Arg Thr Asn Phe Ser Pro Lys Val Val Leu Tyr Ser Glu Asp
                245                 250                 255

Val Asp Ile Glu Thr Pro Asp Thr His Ile Ser Tyr Met Pro Thr Thr
                260                 265                 270

Glu Asp Gly Asn Ser Arg Glu Leu Met Gly Gln Gln Ser Met Pro Asn
            275                 280                 285

Arg Pro Asn Tyr Ile Ala Phe Arg Asp Asn Phe Ile Gly Leu Met Tyr
            290                 295                 300

Tyr Asn Ser Thr Gly Asn Met Gly Val Leu Ala Gly Gln Ala Ser Gln
305                 310                 315                 320

Leu Asn Ala Val Val Asp Leu Gln Asp Arg Asn Thr Glu Leu Ser Tyr
                325                 330                 335

Gln Leu Leu Leu Asp Ser Ile Gly Asp Arg Thr Arg Tyr Phe Ser Met
            340                 345                 350

Trp Asn Gln Ala Val Asp Ser Tyr Asp Pro Asp Val Arg Ile Ile Glu
            355                 360                 365

Asn His Gly Thr Glu Asp Glu Leu Pro Asn Tyr Cys Phe Pro Leu Gly
            370                 375                 380

Gly Val Ile Asn Thr Glu Thr Leu Thr Lys Val Lys Pro Asn Gly Glu
385                 390                 395                 400

Asp Asn Asn Asn Trp Lys Glu Pro Glu Phe Ser Asp Lys Asn Glu Ile
                405                 410                 415
```

-continued

```
Arg Val Gly Asn Asn Phe Ala Met Glu Ile Asn Leu Asn Ala Asn Leu
                420                 425                 430
Trp Arg Asn Phe Leu Tyr Ser Asn Ile Ala Leu Tyr Leu Pro Asp Lys
            435                 440                 445
Leu Lys Tyr Ser Pro Ser Asn Val Lys Ile Ser Asp Asn Pro Asn Thr
450                 455                 460
Tyr Asp Tyr Met Asn Lys Arg Val Val Ala Pro Gly Leu Val Asp Cys
465                 470                 475                 480
Tyr Ile Asn Leu Gly Ala Arg Trp Ser Leu Asp Tyr Met Asp Asn Val
                485                 490                 495
Asn Pro Phe Asn His His Arg Asn Ala Gly Leu Arg Tyr Arg Ser Met
                500                 505                 510
Leu Leu Gly Asn Gly Arg Tyr Val Pro Phe His Ile Gln Val Pro Gln
            515                 520                 525
Lys Phe Phe Ala Ile Lys Asn Leu Leu Leu Pro Gly Ser Tyr Thr
530                 535                 540
Tyr Glu Trp Asn Phe Arg Lys Asp Val Asn Met Val Leu Gln Ser Ser
545                 550                 555                 560
Leu Gly Asn Asp Leu Arg Val Asp Gly Ala Ser Ile Lys Phe Asp Ser
                565                 570                 575
Ile Cys Leu Tyr Ala Thr Phe Phe Pro Met Ala His Asn Thr Ala Ser
                580                 585                 590
Thr Leu Glu Ala Met Leu Arg Asn Asp Thr Asn Asp Gln Ser Phe Asn
            595                 600                 605
Asp Tyr Leu Ser Ala Ala Asn Met Leu Tyr Pro Ile Pro Ala Asn Ala
            610                 615                 620
Thr Asn Val Pro Ile Ser Ile Pro Ser Arg Asn Trp Ala Ala Phe Arg
625                 630                 635                 640
Gly Trp Ala Phe Thr Arg Leu Lys Thr Lys Glu Thr Pro Ser Leu Gly
                645                 650                 655
Ser Gly Tyr Asp Pro Tyr Tyr Thr Tyr Ser Gly Ser Ile Pro Tyr Leu
                660                 665                 670
Asp Gly Thr Phe Tyr Leu Asn His Thr Phe Lys Lys Val Ala Ile Thr
            675                 680                 685
Phe Asp Ser Ser Val Ser Trp Pro Gly Asn Asp Arg Leu Leu Thr Pro
690                 695                 700
Asn Glu Phe Glu Ile Lys Arg Ser Val Asp Gly Glu Gly Tyr Asn Val
705                 710                 715                 720
Ala Gln Cys Asn Met Thr Lys Asp Trp Phe Leu Val Gln Met Leu Ala
                725                 730                 735
Asn Tyr Asn Ile Gly Tyr Gln Gly Phe Tyr Ile Pro Glu Ser Tyr Lys
                740                 745                 750
Asp Arg Met Tyr Ser Phe Phe Arg Asn Phe Gln Pro Met Ser Arg Gln
            755                 760                 765
Val Val Asp Asp Thr Lys Tyr Lys Asp Tyr Gln Gln Val Gly Ile Leu
            770                 775                 780
His Gln His Asn Asn Ser Gly Phe Val Gly Tyr Leu Ala Pro Thr Met
785                 790                 795                 800
Arg Glu Gly Gln Ala Tyr Pro Ala Asn Phe Pro Tyr Pro Leu Ile Gly
                805                 810                 815
Lys Thr Ala Val Asp Ser Ile Thr Gln Lys Lys Phe Leu Cys Asp Arg
            820                 825                 830
Thr Leu Trp Arg Ile Pro Phe Ser Ser Asn Phe Met Ser Met Gly Ala
```

```
                835                 840                 845
Leu Thr Asp Leu Gly Gln Asn Leu Leu Tyr Ala Asn Ser Ala His Ala
    850                 855                 860
Leu Asp Met Thr Phe Glu Val Asp Pro Met Asp Glu Pro Thr Leu Leu
865                 870                 875                 880
Tyr Val Leu Phe Glu Val Phe Asp Val Val Arg Val His Arg Pro His
                885                 890                 895
Arg Gly Val Ile Glu Thr Val Tyr Leu Arg Thr Pro Phe Ser Ala Gly
                900                 905                 910
Asn Ala Thr Thr
        915

<210> SEQ ID NO 84
<211> LENGTH: 928
<212> TYPE: PRT
<213> ORGANISM: Artificial
<220> FEATURE:
<223> OTHER INFORMATION: Chimeric Ad5HVR26(1-7)* hexon protein

<400> SEQUENCE: 84

Met Ala Thr Pro Ser Met Met Pro Gln Trp Ser Tyr Met His Ile Ser
1               5                   10                  15
Gly Gln Asp Ala Ser Glu Tyr Leu Ser Pro Gly Leu Val Gln Phe Ala
            20                  25                  30
Arg Ala Thr Glu Thr Tyr Phe Ser Leu Asn Asn Lys Phe Arg Asn Pro
        35                  40                  45
Thr Val Ala Pro Thr His Asp Val Thr Thr Asp Arg Ser Gln Arg Leu
    50                  55                  60
Thr Leu Arg Phe Ile Pro Val Asp Arg Glu Asp Thr Ala Tyr Ser Tyr
65                  70                  75                  80
Lys Ala Arg Phe Thr Leu Ala Val Gly Asp Asn Arg Val Leu Asp Met
                85                  90                  95
Ala Ser Thr Tyr Phe Asp Ile Arg Gly Val Leu Asp Arg Gly Pro Thr
            100                 105                 110
Phe Lys Pro Tyr Ser Gly Thr Ala Tyr Asn Ala Leu Ala Pro Lys Gly
        115                 120                 125
Ala Pro Asn Pro Cys Glu Trp Asp Thr His Val Phe Gly Gln Ala Pro
    130                 135                 140
Tyr Ser Gly Ile Asn Ile Thr Lys Glu Gly Ile Gln Ile Gly Gln Gly
145                 150                 155                 160
Lys Tyr Ala Asp Lys Thr Phe Gln Pro Glu Pro Gln Ile Gly Glu Ser
                165                 170                 175
Gln Trp Tyr Glu Asn Glu Ile Asn His Ala Ala Gly Arg Val Leu Lys
            180                 185                 190
Lys Thr Thr Pro Met Lys Pro Cys Tyr Gly Ser Tyr Ala Lys Pro Thr
        195                 200                 205
Asn Glu Asn Gly Gly Gln Gly Ile Leu Val Lys Pro Val Asn Glu Gly
    210                 215                 220
Glu Gln Pro Lys Glu Ser Gln Val Glu Met Gln Phe Phe Ser Val Pro
225                 230                 235                 240
Gly Gly Ser Pro Pro Ala Gly Gly Ser Gly Glu Glu Tyr Lys Pro Lys
                245                 250                 255
Val Val Leu Tyr Ser Glu Asp Val Asp Ile Glu Thr Pro Asp Thr His
            260                 265                 270
Ile Ser Tyr Met Pro Thr Thr Ser Asp Gly Asn Ser Arg Glu Leu Met
```

```
            275                 280                 285
Gly Gln Gln Ser Met Pro Asn Arg Pro Asn Tyr Ile Ala Phe Arg Asp
    290                 295                 300
Asn Phe Ile Gly Leu Met Tyr Tyr Asn Ser Thr Gly Asn Met Gly Val
305                 310                 315                 320
Leu Ala Gly Gln Ala Ser Gln Leu Asn Ala Val Val Asp Leu Gln Asp
                325                 330                 335
Arg Asn Thr Glu Leu Ser Tyr Gln Leu Leu Asp Ser Ile Gly Asp
                340                 345                 350
Arg Thr Arg Tyr Phe Ser Met Trp Asn Gln Ala Val Asp Ser Tyr Asp
                355                 360                 365
Pro Asp Val Arg Ile Ile Glu Asn His Gly Thr Glu Asp Glu Leu Pro
    370                 375                 380
Asn Tyr Cys Phe Pro Leu Gly Gly Val Ile Asn Thr Glu Thr Leu Thr
385                 390                 395                 400
Lys Val Lys Pro Thr Asn Gly Asn Asp Gly Ala Glu Glu Ser Glu Trp
                405                 410                 415
Glu Lys Asp Asp Ala Phe Ser Asp Lys Asn Glu Ile Arg Val Gly Asn
                420                 425                 430
Asn Phe Ala Met Glu Ile Asn Leu Asn Ala Asn Leu Trp Arg Asn Phe
                435                 440                 445
Leu Tyr Ser Asn Ile Ala Leu Tyr Leu Pro Asp Lys Leu Lys Tyr Ser
    450                 455                 460
Pro Ser Asn Val Lys Ile Ser Asp Asn Pro Asn Thr Tyr Asp Tyr Met
465                 470                 475                 480
Asn Lys Arg Val Val Ala Pro Gly Leu Val Asp Cys Tyr Ile Asn Leu
                485                 490                 495
Gly Ala Arg Trp Ser Leu Asp Tyr Met Asp Asn Val Asn Pro Phe Asn
                500                 505                 510
His His Arg Asn Ala Gly Leu Arg Tyr Arg Ser Met Leu Leu Gly Asn
                515                 520                 525
Gly Arg Tyr Val Pro Phe His Ile Gln Val Pro Gln Lys Phe Phe Ala
    530                 535                 540
Ile Lys Asn Leu Leu Leu Pro Gly Ser Tyr Thr Tyr Glu Trp Asn
545                 550                 555                 560
Phe Arg Lys Asp Val Asn Met Val Leu Gln Ser Ser Leu Gly Asn Asp
                565                 570                 575
Leu Arg Val Asp Gly Ala Ser Ile Lys Phe Asp Ser Ile Cys Leu Tyr
                580                 585                 590
Ala Thr Phe Phe Pro Met Ala His Asn Thr Ala Ser Thr Leu Glu Ala
                595                 600                 605
Met Leu Arg Asn Asp Thr Asn Asp Gln Ser Phe Asn Asp Tyr Leu Ser
    610                 615                 620
Ala Ala Asn Met Leu Tyr Pro Ile Pro Ala Asn Ala Thr Asn Val Pro
625                 630                 635                 640
Ile Ser Ile Pro Ser Arg Asn Trp Ala Ala Phe Arg Gly Trp Ala Phe
                645                 650                 655
Thr Arg Leu Lys Thr Lys Glu Thr Pro Ser Leu Gly Ser Gly Tyr Asp
                660                 665                 670
Pro Tyr Tyr Thr Tyr Ser Gly Ser Ile Pro Tyr Leu Asp Gly Thr Phe
    675                 680                 685
Tyr Leu Asn His Thr Phe Lys Lys Val Ala Ile Thr Phe Asp Ser Ser
    690                 695                 700
```

```
Val Ser Trp Pro Gly Asn Asp Arg Leu Leu Thr Pro Asn Glu Phe Glu
705                 710                 715                 720

Ile Lys Arg Ser Val Asp Gly Glu Gly Tyr Asn Val Ala Gln Cys Asn
                725                 730                 735

Met Thr Lys Asp Trp Phe Leu Val Gln Met Leu Ala Asn Tyr Asn Ile
            740                 745                 750

Gly Tyr Gln Gly Phe Tyr Ile Pro Glu Ser Tyr Lys Asp Arg Met Tyr
        755                 760                 765

Ser Phe Phe Arg Asn Phe Gln Pro Met Ser Arg Gln Val Val Asp Asp
    770                 775                 780

Thr Lys Tyr Lys Asp Tyr Gln Gln Val Gly Ile Leu His Gln His Asn
785                 790                 795                 800

Asn Ser Gly Phe Val Gly Tyr Leu Ala Pro Thr Met Arg Glu Gly Gln
                805                 810                 815

Ala Tyr Pro Ala Asn Phe Pro Tyr Pro Leu Ile Gly Lys Thr Ala Val
                820                 825                 830

Asp Ser Ile Thr Gln Lys Lys Phe Leu Cys Asp Arg Thr Leu Trp Arg
                835                 840                 845

Ile Pro Phe Ser Ser Asn Phe Met Ser Met Gly Ala Leu Thr Asp Leu
            850                 855                 860

Gly Gln Asn Leu Leu Tyr Ala Asn Ser Ala His Ala Leu Asp Met Thr
865                 870                 875                 880

Phe Glu Val Asp Pro Met Asp Glu Pro Thr Leu Leu Tyr Val Leu Phe
                885                 890                 895

Glu Val Phe Asp Val Val Arg Val His Arg Pro His Arg Gly Val Ile
                900                 905                 910

Glu Thr Val Tyr Leu Arg Thr Pro Phe Ser Ala Gly Asn Ala Thr Thr
            915                 920                 925

<210> SEQ ID NO 85
<211> LENGTH: 923
<212> TYPE: PRT
<213> ORGANISM: Artificial
<220> FEATURE:
<223> OTHER INFORMATION: Chimeric Ad5HVR49(1-7)* hexon protein

<400> SEQUENCE: 85

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Thr His Val Phe Gly Gln Ala Pro
    130                 135                 140
```

```
Tyr Ser Gly Ile Asn Ile Thr Lys Glu Gly Ile Gln Ile Gly Gln Gly
145                 150                 155                 160

Lys Tyr Ala Asp Lys Thr Phe Gln Pro Glu Pro Gln Ile Gly Glu Ser
            165                 170                 175

Gln Trp Tyr Asn Thr Glu Ile Asn His Ala Ala Gly Arg Val Leu Lys
            180                 185                 190

Lys Thr Thr Pro Met Lys Pro Cys Tyr Gly Ser Tyr Ala Lys Pro Thr
            195                 200                 205

Asn Glu Asn Gly Gly Gln Gly Ile Leu Val Lys Thr Gly Glu Asn Gly
        210                 215                 220

Lys Pro Thr Glu Glu Ser Gln Val Glu Met Gln Phe Phe Ser Leu Arg
225                 230                 235                 240

Gln Asn Asp Thr Gly Asn Asn Gln Pro Lys Val Val Leu Tyr
                245                 250                 255

Ser Glu Asp Val Asp Ile Glu Thr Pro Asp Thr His Ile Ser Tyr Met
                260                 265                 270

Pro Thr Thr Ser Asp Gly Asn Ser Arg Glu Leu Met Gly Gln Gln Ser
            275                 280                 285

Met Pro Asn Arg Pro Asn Tyr Ile Ala Phe Arg Asp Asn Phe Ile Gly
            290                 295                 300

Leu Met Tyr Tyr Asn Ser Thr Gly Asn Met Gly Val Leu Ala Gly Gln
305                 310                 315                 320

Ala Ser Gln Leu Asn Ala Val Val Asp Leu Gln Asp Arg Asn Thr Glu
            325                 330                 335

Leu Ser Tyr Gln Leu Leu Leu Asp Ser Ile Gly Asp Arg Thr Arg Tyr
            340                 345                 350

Phe Ser Met Trp Asn Gln Ala Val Asp Ser Tyr Asp Pro Asp Val Arg
            355                 360                 365

Ile Ile Glu Asn His Gly Thr Glu Asp Glu Leu Pro Asn Tyr Cys Phe
370                 375                 380

Pro Leu Gly Gly Val Ile Asn Thr Glu Thr Leu Thr Lys Val Lys Pro
385                 390                 395                 400

Asp Thr Thr Val Ala Gly Thr Asn Asp Lys Trp Lys Val Asn Ala Lys
            405                 410                 415

Phe Ser Asp Lys Asn Glu Ile Arg Val Gly Asn Asn Phe Ala Met Glu
            420                 425                 430

Ile Asn Leu Asn Ala Asn Leu Trp Arg Asn Phe Leu Tyr Ser Asn Ile
            435                 440                 445

Ala Leu Tyr Leu Pro Asp Lys Leu Lys Tyr Ser Pro Ser Asn Val Lys
450                 455                 460

Ile Ser Asp Asn Pro Asn Thr Tyr Asp Tyr Met Asn Lys Arg Val Val
465                 470                 475                 480

Ala Pro Gly Leu Val Asp Cys Tyr Ile Asn Leu Gly Ala Arg Trp Ser
            485                 490                 495

Leu Asp Tyr Met Asp Asn Val Asn Pro Phe Asn His Arg Asn Ala
            500                 505                 510

Gly Leu Arg Tyr Arg Ser Met Leu Leu Gly Asn Gly Arg Tyr Val Pro
            515                 520                 525

Phe His Ile Gln Val Pro Gln Lys Phe Ala Ile Lys Asn Leu Leu
            530                 535                 540

Leu Leu Pro Gly Ser Tyr Thr Tyr Glu Trp Asn Phe Arg Lys Asp Val
545                 550                 555                 560
```

Asn Met Val Leu Gln Ser Ser Leu Gly Asn Asp Leu Arg Val Asp Gly
            565                 570                 575

Ala Ser Ile Lys Phe Asp Ser Ile Cys Leu Tyr Ala Thr Phe Phe Pro
            580                 585                 590

Met Ala His Asn Thr Ala Ser Thr Leu Glu Ala Met Leu Arg Asn Asp
            595                 600                 605

Thr Asn Asp Gln Ser Phe Asn Asp Tyr Leu Ser Ala Ala Asn Met Leu
            610                 615                 620

Tyr Pro Ile Pro Ala Asn Ala Thr Asn Val Pro Ile Ser Ile Pro Ser
625                 630                 635                 640

Arg Asn Trp Ala Ala Phe Arg Gly Trp Ala Phe Thr Arg Leu Lys Thr
                645                 650                 655

Lys Glu Thr Pro Ser Leu Gly Ser Gly Tyr Asp Pro Tyr Tyr Thr Tyr
            660                 665                 670

Ser Gly Ser Ile Pro Tyr Leu Asp Gly Thr Phe Tyr Leu Asn His Thr
            675                 680                 685

Phe Lys Lys Val Ala Ile Thr Phe Asp Ser Ser Val Ser Trp Pro Gly
            690                 695                 700

Asn Asp Arg Leu Leu Thr Pro Asn Glu Phe Glu Ile Lys Arg Ser Val
705                 710                 715                 720

Asp Gly Glu Gly Tyr Asn Val Ala Gln Cys Asn Met Thr Lys Asp Trp
                725                 730                 735

Phe Leu Val Gln Met Leu Ala Asn Tyr Asn Ile Gly Tyr Gln Gly Phe
            740                 745                 750

Tyr Ile Pro Glu Ser Tyr Lys Asp Arg Met Tyr Ser Phe Phe Arg Asn
            755                 760                 765

Phe Gln Pro Met Ser Arg Gln Val Val Asp Asp Thr Lys Tyr Lys Asp
            770                 775                 780

Tyr Gln Gln Val Gly Ile Leu His Gln His Asn Asn Ser Gly Phe Val
785                 790                 795                 800

Gly Tyr Leu Ala Pro Thr Met Arg Glu Gly Gln Ala Tyr Pro Ala Asn
                805                 810                 815

Phe Pro Tyr Pro Leu Ile Gly Lys Thr Ala Val Asp Ser Ile Thr Gln
            820                 825                 830

Lys Lys Phe Leu Cys Asp Arg Thr Leu Trp Arg Ile Pro Phe Ser Ser
            835                 840                 845

Asn Phe Met Ser Met Gly Ala Leu Thr Asp Leu Gly Gln Asn Leu Leu
850                 855                 860

Tyr Ala Asn Ser Ala His Ala Leu Asp Met Thr Phe Glu Val Asp Pro
865                 870                 875                 880

Met Asp Glu Pro Thr Leu Leu Tyr Val Leu Phe Glu Val Phe Asp Val
                885                 890                 895

Val Arg Val His Arg Pro His Arg Gly Val Ile Glu Thr Val Tyr Leu
            900                 905                 910

Arg Thr Pro Phe Ser Ala Gly Asn Ala Thr Thr
            915                 920

<210> SEQ ID NO 86
<211> LENGTH: 331
<212> TYPE: PRT
<213> ORGANISM: Artificial
<220> FEATURE:
<223> OTHER INFORMATION: Chimeric Ad35k49 fiber protein

<400> SEQUENCE: 86

-continued

```
Met Thr Lys Arg Val Arg Leu Ser Asp Ser Phe Asn Pro Val Tyr Pro
1               5                   10                  15

Tyr Glu Asp Glu Ser Thr Ser Gln His Pro Phe Ile Asn Pro Gly Phe
            20                  25                  30

Ile Ser Pro Asn Gly Phe Thr Gln Ser Pro Asp Gly Val Leu Thr Leu
        35                  40                  45

Lys Cys Leu Thr Pro Leu Thr Thr Thr Gly Gly Ser Leu Gln Leu Lys
50                  55                      60

Val Gly Gly Gly Leu Thr Val Asp Asp Thr Asp Gly Thr Leu Gln Glu
65                  70                  75                  80

Asn Ile Arg Ala Thr Ala Pro Ile Thr Lys Asn Asn His Ser Val Glu
                85                  90                  95

Leu Ser Ile Gly Asn Gly Leu Glu Thr Gln Asn Asn Lys Leu Cys Ala
            100                 105                 110

Lys Leu Gly Asn Gly Leu Lys Phe Asn Asn Gly Asp Ile Cys Ile Lys
        115                 120                 125

Asp Ser Ile Asn Thr Leu Trp Thr Thr Pro Asp Pro Ser Pro Asn Cys
130                 135                     140

Lys Val Ser Glu Glu Lys Asp Ser Lys Leu Thr Leu Val Leu Thr Lys
145                 150                 155                 160

Cys Gly Ser Gln Ile Leu Ala Ser Val Ser Leu Leu Val Val Lys Gly
                165                 170                 175

Lys Phe Ala Asn Ile Asn Asn Lys Thr Asn Pro Gly Glu Asp Tyr Lys
            180                 185                 190

Lys Phe Ser Val Lys Leu Leu Phe Asp Ala Asn Gly Lys Leu Leu Thr
        195                 200                 205

Gly Ser Ser Leu Asp Gly Asn Tyr Trp Asn Tyr Lys Asn Lys Asp Ser
210                 215                 220

Val Ile Gly Ser Pro Tyr Glu Asn Ala Val Pro Phe Met Pro Asn Ser
225                 230                 235                 240

Thr Ala Tyr Pro Lys Ile Ile Asn Asn Gly Thr Ala Asn Pro Glu Asp
                245                 250                 255

Lys Lys Ser Ala Ala Lys Lys Thr Ile Val Thr Asn Val Tyr Leu Gly
            260                 265                 270

Gly Asp Ala Ala Lys Pro Val Ala Thr Thr Ile Ser Phe Asn Lys Glu
        275                 280                 285

Thr Glu Ser Asn Cys Val Tyr Ser Ile Thr Phe Asp Phe Ala Trp Asn
290                 295                 300

Lys Thr Tyr Lys Asn Val Pro Phe Asp Ser Ser Ser Leu Thr Phe Ser
305                 310                 315                 320

Tyr Ile Ala Gln Asp Ala Glu Asp Lys Asn Glu
                325                 330
```

<210> SEQ ID NO 87
<211> LENGTH: 925
<212> TYPE: PRT
<213> ORGANISM: Artificial
<220> FEATURE:
<223> OTHER INFORMATION: Chimeric Ad5HVR48(1-7)* hexon protein

<400> SEQUENCE: 87

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30
```

```
Arg Ala Thr Glu Thr Tyr Phe Ser Leu Asn Asn Lys Phe Arg Asn Pro
            35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Thr His Val Phe Gly Gln Ala Pro
    130                 135                 140

Tyr Ser Gly Ile Asn Ile Thr Lys Glu Gly Ile Gln Ile Gly Gln Gly
145                 150                 155                 160

Lys Tyr Ala Asp Lys Thr Phe Gln Pro Glu Pro Gln Ile Gly Glu Ser
                165                 170                 175

Gln Trp Tyr Asp Ser Asp Ile Asn His Ala Ala Gly Arg Val Leu Lys
            180                 185                 190

Lys Thr Thr Pro Met Lys Pro Cys Tyr Gly Ser Tyr Ala Lys Pro Thr
        195                 200                 205

Asn Glu Asn Gly Gly Gln Gly Ile Leu Val Lys Thr Pro Glu Lys Glu
    210                 215                 220

Gly Glu Glu Pro Lys Glu Ser Gln Val Glu Met Gln Phe Phe Ser Ile
225                 230                 235                 240

Pro Ser Thr Gly Thr Gly Gly Asn Gly Thr Asn Val Asn Phe Lys Pro
                245                 250                 255

Lys Val Val Leu Tyr Ser Glu Asp Val Asp Ile Glu Thr Pro Asp Thr
            260                 265                 270

His Ile Ser Tyr Met Pro Thr Lys Glu Asp Gly Asn Ser Arg Glu Leu
        275                 280                 285

Met Gly Gln Gln Ser Met Pro Asn Arg Pro Asn Tyr Ile Ala Phe Arg
    290                 295                 300

Asp Asn Phe Ile Gly Leu Met Tyr Tyr Asn Ser Thr Gly Asn Met Gly
305                 310                 315                 320

Val Leu Ala Gly Gln Ala Ser Gln Leu Asn Ala Val Val Asp Leu Gln
                325                 330                 335

Asp Arg Asn Thr Glu Leu Ser Tyr Gln Leu Leu Leu Asp Ser Ile Gly
            340                 345                 350

Asp Arg Thr Arg Tyr Phe Ser Met Trp Asn Gln Ala Val Asp Ser Tyr
        355                 360                 365

Asp Pro Asp Val Arg Ile Ile Glu Asn His Gly Thr Glu Asp Glu Leu
    370                 375                 380

Pro Asn Tyr Cys Phe Pro Leu Gly Gly Val Ile Asn Thr Glu Thr Leu
385                 390                 395                 400

Thr Lys Val Lys Pro Lys Thr Asn Asn Thr Glu Trp Glu Lys Asp
                405                 410                 415

Thr Ala Phe Ser Asp Lys Asn Glu Ile Arg Val Gly Asn Asn Phe Ala
            420                 425                 430

Met Glu Ile Asn Leu Asn Ala Asn Leu Trp Arg Asn Phe Leu Tyr Ser
        435                 440                 445

Asn Ile Ala Leu Tyr Leu Pro Asp Lys Leu Lys Tyr Ser Pro Ser Asn
```

```
            450                 455                 460
Val Lys Ile Ser Asp Asn Pro Asn Thr Tyr Asp Tyr Met Asn Lys Arg
465                 470                 475                 480

Val Val Ala Pro Gly Leu Val Asp Cys Tyr Ile Asn Leu Gly Ala Arg
                485                 490                 495

Trp Ser Leu Asp Tyr Met Asp Asn Val Asn Pro Phe Asn His His Arg
                500                 505                 510

Asn Ala Gly Leu Arg Tyr Arg Ser Met Leu Leu Gly Asn Gly Arg Tyr
                515                 520                 525

Val Pro Phe His Ile Gln Val Pro Gln Lys Phe Phe Ala Ile Lys Asn
530                 535                 540

Leu Leu Leu Leu Pro Gly Ser Tyr Thr Tyr Glu Trp Asn Phe Arg Lys
545                 550                 555                 560

Asp Val Asn Met Val Leu Gln Ser Ser Leu Gly Asn Asp Leu Arg Val
                565                 570                 575

Asp Gly Ala Ser Ile Lys Phe Asp Ser Ile Cys Leu Tyr Ala Thr Phe
                580                 585                 590

Phe Pro Met Ala His Asn Thr Ala Ser Thr Leu Glu Ala Met Leu Arg
                595                 600                 605

Asn Asp Thr Asn Asp Gln Ser Phe Asn Asp Tyr Leu Ser Ala Ala Asn
                610                 615                 620

Met Leu Tyr Pro Ile Pro Ala Asn Ala Thr Asn Val Pro Ile Ser Ile
625                 630                 635                 640

Pro Ser Arg Asn Trp Ala Ala Phe Arg Gly Trp Ala Phe Thr Arg Leu
                645                 650                 655

Lys Thr Lys Glu Thr Pro Ser Leu Gly Ser Gly Tyr Asp Pro Tyr Tyr
                660                 665                 670

Thr Tyr Ser Gly Ser Ile Pro Tyr Leu Asp Gly Thr Phe Tyr Leu Asn
                675                 680                 685

His Thr Phe Lys Lys Val Ala Ile Thr Phe Asp Ser Ser Val Ser Trp
    690                 695                 700

Pro Gly Asn Asp Arg Leu Leu Thr Pro Asn Glu Phe Glu Ile Lys Arg
705                 710                 715                 720

Ser Val Asp Gly Glu Gly Tyr Asn Val Ala Gln Cys Asn Met Thr Lys
                725                 730                 735

Asp Trp Phe Leu Val Gln Met Leu Ala Asn Tyr Asn Ile Gly Tyr Gln
                740                 745                 750

Gly Phe Tyr Ile Pro Glu Ser Tyr Lys Asp Arg Met Tyr Ser Phe Phe
                755                 760                 765

Arg Asn Phe Gln Pro Met Ser Arg Gln Val Val Asp Asp Thr Lys Tyr
                770                 775                 780

Lys Asp Tyr Gln Gln Val Gly Ile Leu His Gln His Asn Asn Ser Gly
785                 790                 795                 800

Phe Val Gly Tyr Leu Ala Pro Thr Met Arg Glu Gly Gln Ala Tyr Pro
                805                 810                 815

Ala Asn Phe Pro Tyr Pro Leu Ile Gly Lys Thr Ala Val Asp Ser Ile
                820                 825                 830

Thr Gln Lys Lys Phe Leu Cys Asp Arg Thr Leu Trp Arg Ile Pro Phe
                835                 840                 845

Ser Ser Asn Phe Met Ser Met Gly Ala Leu Thr Asp Leu Gly Gln Asn
                850                 855                 860

Leu Leu Tyr Ala Asn Ser Ala His Ala Leu Asp Met Thr Phe Glu Val
865                 870                 875                 880
```

-continued

```
Asp Pro Met Asp Glu Pro Thr Leu Leu Tyr Val Leu Phe Glu Val Phe
            885                 890                 895
Asp Val Val Arg Val His Arg Pro His Arg Gly Val Ile Glu Thr Val
        900                 905                 910
Tyr Leu Arg Thr Pro Phe Ser Ala Gly Asn Ala Thr
    915                 920                 925

<210> SEQ ID NO 88
<211> LENGTH: 29
<212> TYPE: PRT
<213> ORGANISM: Adenovirus serotype 5

<400> SEQUENCE: 88

Glu Ala Ala Thr Ala Leu Glu Ile Asn Leu Glu Glu Glu Asp Asp
1               5                   10                  15
Asn Glu Asp Glu Val Asp Glu Gln Ala Glu Gln Gln Lys
            20                  25

<210> SEQ ID NO 89
<211> LENGTH: 6
<212> TYPE: PRT
<213> ORGANISM: Adenovirus serotype 5

<400> SEQUENCE: 89

Val Glu Gly Gln Thr Pro
1               5

<210> SEQ ID NO 90
<211> LENGTH: 3
<212> TYPE: PRT
<213> ORGANISM: Adenovirus serotype 5

<400> SEQUENCE: 90

Glu Thr Glu
1

<210> SEQ ID NO 91
<211> LENGTH: 7
<212> TYPE: PRT
<213> ORGANISM: Adenovirus serotype 5

<400> SEQUENCE: 91

Lys Gln Gln Asn Gly Lys Leu
1               5

<210> SEQ ID NO 92
<211> LENGTH: 13
<212> TYPE: PRT
<213> ORGANISM: Adenovirus serotype 5

<400> SEQUENCE: 92

Thr Thr Glu Ala Thr Ala Gly Asn Gly Asp Asn Leu Thr
1               5                   10

<210> SEQ ID NO 93
<211> LENGTH: 3
<212> TYPE: PRT
<213> ORGANISM: Adenovirus serotype 5

<400> SEQUENCE: 93

Ile Lys Glu
1
```

<210> SEQ ID NO 94
<211> LENGTH: 14
<212> TYPE: PRT
<213> ORGANISM: Adenovirus serotype 5

<400> SEQUENCE: 94

Lys Thr Gly Gln Glu Asn Gly Trp Glu Lys Asp Ala Thr Glu
1               5                   10

<210> SEQ ID NO 95
<211> LENGTH: 14
<212> TYPE: PRT
<213> ORGANISM: Adenovirus serotype 48

<400> SEQUENCE: 95

Glu Lys Lys Asn Gly Gly Gly Ser Asp Ala Asn Gln Met Gln
1               5                   10

<210> SEQ ID NO 96
<211> LENGTH: 12
<212> TYPE: PRT
<213> ORGANISM: Adenovirus serotype 48

<400> SEQUENCE: 96

Ile Asp Ala Thr Lys Glu Glu Asp Asn Gly Lys Glu
1               5                   10

<210> SEQ ID NO 97
<211> LENGTH: 3
<212> TYPE: PRT
<213> ORGANISM: Adenovirus serotype 48

<400> SEQUENCE: 97

Asp Ser Asp
1

<210> SEQ ID NO 98
<211> LENGTH: 11
<212> TYPE: PRT
<213> ORGANISM: Adenovirus serotype 48

<400> SEQUENCE: 98

Lys Thr Pro Glu Lys Glu Gly Glu Glu Pro Lys
1               5                   10

<210> SEQ ID NO 99
<211> LENGTH: 16
<212> TYPE: PRT
<213> ORGANISM: Adenovirus serotype 48

<400> SEQUENCE: 99

Ile Pro Ser Thr Gly Thr Gly Gly Asn Gly Thr Asn Val Asn Phe Lys
1               5                   10                  15

<210> SEQ ID NO 100
<211> LENGTH: 3
<212> TYPE: PRT
<213> ORGANISM: Adenovirus serotype 48

<400> SEQUENCE: 100

Lys Glu Asp
1

<210> SEQ ID NO 101

```
<211> LENGTH: 13
<212> TYPE: PRT
<213> ORGANISM: Adenovirus serotype 48

<400> SEQUENCE: 101

Lys Thr Thr Asn Asn Thr Glu Trp Glu Lys Asp Thr Ala
1               5                   10

<210> SEQ ID NO 102
<211> LENGTH: 24
<212> TYPE: PRT
<213> ORGANISM: Adenovirus serotype 35

<400> SEQUENCE: 102

Ala Lys Gly Val Pro Thr Ala Ala Ala Gly Asn Gly Glu Glu
1               5                   10                  15

His Glu Thr Glu Glu Lys Thr Ala
            20

<210> SEQ ID NO 103
<211> LENGTH: 11
<212> TYPE: PRT
<213> ORGANISM: Adenovirus serotype 35

<400> SEQUENCE: 103

Leu Glu Ile Ser Ala Glu Asn Glu Ser Lys Pro
1               5                   10

<210> SEQ ID NO 104
<211> LENGTH: 3
<212> TYPE: PRT
<213> ORGANISM: Adenovirus serotype 35

<400> SEQUENCE: 104

Asp Leu Asp
1

<210> SEQ ID NO 105
<211> LENGTH: 10
<212> TYPE: PRT
<213> ORGANISM: Adenovirus serotype 35

<400> SEQUENCE: 105

Lys Asn Ser Glu Pro Ser Ser Glu Lys Ile
1               5                   10

<210> SEQ ID NO 106
<211> LENGTH: 9
<212> TYPE: PRT
<213> ORGANISM: Adenovirus serotype 35

<400> SEQUENCE: 106

Asn Ser Ser Gln Arg Thr Asn Phe Ser
1               5

<210> SEQ ID NO 107
<211> LENGTH: 3
<212> TYPE: PRT
<213> ORGANISM: Adenovirus serotype 35

<400> SEQUENCE: 107

Thr Glu Asp
1
```

```
<210> SEQ ID NO 108
<211> LENGTH: 12
<212> TYPE: PRT
<213> ORGANISM: Adenovirus serotype 35

<400> SEQUENCE: 108

Asn Gly Glu Asp Asn Asn Asn Trp Lys Glu Pro Glu
1               5                   10

<210> SEQ ID NO 109
<211> LENGTH: 21
<212> TYPE: PRT
<213> ORGANISM: Adenovirus serotype 11

<400> SEQUENCE: 109

Ala Glu Gly Val Lys Asn Thr Thr Gly Glu Glu His Val Thr Glu Glu
1               5                   10                  15

Glu Thr Asn Thr Thr
            20

<210> SEQ ID NO 110
<211> LENGTH: 10
<212> TYPE: PRT
<213> ORGANISM: Adenovirus serotype 11

<400> SEQUENCE: 110

Leu Glu Val Ser Asp Glu Glu Ser Lys Pro
1               5                   10

<210> SEQ ID NO 111
<211> LENGTH: 3
<212> TYPE: PRT
<213> ORGANISM: Adenovirus serotype 11

<400> SEQUENCE: 111

Asp Leu Asp
1

<210> SEQ ID NO 112
<211> LENGTH: 10
<212> TYPE: PRT
<213> ORGANISM: Adenovirus serotype 11

<400> SEQUENCE: 112

Lys Thr Thr Glu Gln Pro Asn Gln Lys Val
1               5                   10

<210> SEQ ID NO 113
<211> LENGTH: 9
<212> TYPE: PRT
<213> ORGANISM: Adenovirus serotype 11

<400> SEQUENCE: 113

Ala Ala Ser Gln Lys Thr Asn Leu Ser
1               5

<210> SEQ ID NO 114
<211> LENGTH: 3
<212> TYPE: PRT
<213> ORGANISM: Adenovirus serotype 11

<400> SEQUENCE: 114

Thr Glu Asp
1
```

```
<210> SEQ ID NO 115
<211> LENGTH: 12
<212> TYPE: PRT
<213> ORGANISM: Adenovirus serotype 11

<400> SEQUENCE: 115

Asn Gly Asp Asn Ala Pro Asn Trp Lys Glu Pro Glu
1               5                   10

<210> SEQ ID NO 116
<211> LENGTH: 17
<212> TYPE: PRT
<213> ORGANISM: Adenovirus serotype 26

<400> SEQUENCE: 116

Thr Lys Glu Lys Gln Gly Thr Thr Gly Gly Val Gln Gln Glu Lys Asp
1               5                   10                  15

Val

<210> SEQ ID NO 117
<211> LENGTH: 11
<212> TYPE: PRT
<213> ORGANISM: Adenovirus serotype 26

<400> SEQUENCE: 117

Thr Asp Glu Thr Ala Glu Asn Gly Lys Lys Asp
1               5                   10

<210> SEQ ID NO 118
<211> LENGTH: 3
<212> TYPE: PRT
<213> ORGANISM: Adenovirus serotype 26

<400> SEQUENCE: 118

Glu Asn Glu
1

<210> SEQ ID NO 119
<211> LENGTH: 10
<212> TYPE: PRT
<213> ORGANISM: Adenovirus serotype 26

<400> SEQUENCE: 119

Lys Pro Val Asn Glu Gly Glu Gln Pro Lys
1               5                   10

<210> SEQ ID NO 120
<211> LENGTH: 16
<212> TYPE: PRT
<213> ORGANISM: Adenovirus serotype 26

<400> SEQUENCE: 120

Val Pro Gly Gly Ser Pro Pro Ala Gly Gly Ser Gly Glu Glu Tyr Lys
1               5                   10                  15

<210> SEQ ID NO 121
<211> LENGTH: 3
<212> TYPE: PRT
<213> ORGANISM: Adenovirus serotype 26

<400> SEQUENCE: 121

Thr Ser Asp
1
```

```
<210> SEQ ID NO 122
<211> LENGTH: 17
<212> TYPE: PRT
<213> ORGANISM: Adenovirus serotype 26

<400> SEQUENCE: 122

Thr Asn Gly Asn Asp Gly Ala Glu Glu Ser Glu Trp Glu Lys Asp Asp
1               5                   10                  15
Ala

<210> SEQ ID NO 123
<211> LENGTH: 11
<212> TYPE: PRT
<213> ORGANISM: Adenovirus serotype pan9

<400> SEQUENCE: 123

Tyr Lys Ala Asp Gly Glu Thr Ala Thr Glu Lys
1               5                   10

<210> SEQ ID NO 124
<211> LENGTH: 7
<212> TYPE: PRT
<213> ORGANISM: Adenovirus serotype pan9

<400> SEQUENCE: 124

Thr Asp Thr Asp Asp Gln Pro
1               5

<210> SEQ ID NO 125
<211> LENGTH: 3
<212> TYPE: PRT
<213> ORGANISM: Adenovirus serotype pan9

<400> SEQUENCE: 125

Asp Ile Thr
1

<210> SEQ ID NO 126
<211> LENGTH: 8
<212> TYPE: PRT
<213> ORGANISM: Adenovirus serotype pan9

<400> SEQUENCE: 126

Lys Thr Gly Thr Gly Thr Thr Lys
1               5

<210> SEQ ID NO 127
<211> LENGTH: 10
<212> TYPE: PRT
<213> ORGANISM: Adenovirus serotype pan9

<400> SEQUENCE: 127

Asn Arg Ser Ala Ala Ala Ala Gly Leu Ala
1               5                   10

<210> SEQ ID NO 128
<211> LENGTH: 3
<212> TYPE: PRT
<213> ORGANISM: Adenovirus serotype pan9

<400> SEQUENCE: 128

Thr Asp Asp
1
```

-continued

```
<210> SEQ ID NO 129
<211> LENGTH: 13
<212> TYPE: PRT
<213> ORGANISM: Adenovirus serotype pan9

<400> SEQUENCE: 129

Asn Gly Thr Asp Gln Thr Thr Trp Thr Lys Asp Asp Ser
1               5                   10

<210> SEQ ID NO 130
<211> LENGTH: 24
<212> TYPE: PRT
<213> ORGANISM: Adenovirus serotype 34

<400> SEQUENCE: 130

Asp Lys Gly Val Thr Ser Thr Gly Leu Val Asp Gly Asn Thr Asp
1               5                   10                  15

Asp Gly Glu Glu Ala Lys Lys Ala
            20

<210> SEQ ID NO 131
<211> LENGTH: 10
<212> TYPE: PRT
<213> ORGANISM: Adenovirus serotype 34

<400> SEQUENCE: 131

Leu Glu Val Ser Thr Glu Gly Pro Lys Pro
1               5                   10

<210> SEQ ID NO 132
<211> LENGTH: 3
<212> TYPE: PRT
<213> ORGANISM: Adenovirus serotype 34

<400> SEQUENCE: 132

Asp Leu Asp
1

<210> SEQ ID NO 133
<211> LENGTH: 11
<212> TYPE: PRT
<213> ORGANISM: Adenovirus serotype 34

<400> SEQUENCE: 133

Lys Pro Lys Glu Asp Asp Gly Thr Asn Asn Ile
1               5                   10

<210> SEQ ID NO 134
<211> LENGTH: 9
<212> TYPE: PRT
<213> ORGANISM: Adenovirus serotype 34

<400> SEQUENCE: 134

Leu Arg Ser Gln Arg Ser Glu Leu Lys
1               5

<210> SEQ ID NO 135
<211> LENGTH: 3
<212> TYPE: PRT
<213> ORGANISM: Adenovirus serotype 34

<400> SEQUENCE: 135

Val Ser Asp
1
```

```
<210> SEQ ID NO 136
<211> LENGTH: 11
<212> TYPE: PRT
<213> ORGANISM: Adenovirus serotype 34

<400> SEQUENCE: 136

Asn Gly Asp Gln Ser Thr Trp Thr Asn Val Asp
1               5                   10

<210> SEQ ID NO 137
<211> LENGTH: 11
<212> TYPE: PRT
<213> ORGANISM: Adenovirus serotype 49

<400> SEQUENCE: 137

Ala Lys Glu Asn Asn Gly Gln Gly Glu Ala Lys
1               5                   10

<210> SEQ ID NO 138
<211> LENGTH: 13
<212> TYPE: PRT
<213> ORGANISM: Adenovirus serotype 49

<400> SEQUENCE: 138

Ile Asp Glu Asn Lys Glu Glu Asp Glu Glu Gly Arg Glu
1               5                   10

<210> SEQ ID NO 139
<211> LENGTH: 3
<212> TYPE: PRT
<213> ORGANISM: Adenovirus serotype 49

<400> SEQUENCE: 139

Asn Thr Glu
1

<210> SEQ ID NO 140
<211> LENGTH: 10
<212> TYPE: PRT
<213> ORGANISM: Adenovirus serotype 49

<400> SEQUENCE: 140

Lys Thr Gly Glu Asn Gly Lys Pro Thr Glu
1               5                   10

<210> SEQ ID NO 141
<211> LENGTH: 12
<212> TYPE: PRT
<213> ORGANISM: Adenovirus serotype 49

<400> SEQUENCE: 141

Leu Arg Gln Asn Asp Thr Gly Gly Asn Asn Asn Gln
1               5                   10

<210> SEQ ID NO 142
<211> LENGTH: 3
<212> TYPE: PRT
<213> ORGANISM: Adenovirus serotype 49

<400> SEQUENCE: 142

Thr Ser Asp
1
```

```
<210> SEQ ID NO 143
<211> LENGTH: 16
<212> TYPE: PRT
<213> ORGANISM: Adenovirus serotype 49

<400> SEQUENCE: 143

Asp Thr Thr Val Ala Gly Thr Asn Asp Lys Trp Lys Val Asn Ala Lys
1               5                   10                  15

<210> SEQ ID NO 144
<211> LENGTH: 14
<212> TYPE: PRT
<213> ORGANISM: Adenovirus serotype 50

<400> SEQUENCE: 144

Asn Lys Gly Asp Glu Glu Asp Gly Glu Asp Asp Gln Gln Ala
1               5                   10

<210> SEQ ID NO 145
<211> LENGTH: 11
<212> TYPE: PRT
<213> ORGANISM: Adenovirus serotype 50

<400> SEQUENCE: 145

Leu Glu Val Pro Ser Glu Gly Gly Pro Lys Pro
1               5                   10

<210> SEQ ID NO 146
<211> LENGTH: 3
<212> TYPE: PRT
<213> ORGANISM: Adenovirus serotype 50

<400> SEQUENCE: 146

Asp Thr Asp
1

<210> SEQ ID NO 147
<211> LENGTH: 8
<212> TYPE: PRT
<213> ORGANISM: Adenovirus serotype 50

<400> SEQUENCE: 147

Lys Lys Glu Glu Glu Gly Lys Val
1               5

<210> SEQ ID NO 148
<211> LENGTH: 9
<212> TYPE: PRT
<213> ORGANISM: Adenovirus serotype 50

<400> SEQUENCE: 148

Leu Arg Ser Gln Met Thr Gly Leu Lys
1               5

<210> SEQ ID NO 149
<211> LENGTH: 3
<212> TYPE: PRT
<213> ORGANISM: Adenovirus serotype 50

<400> SEQUENCE: 149

Ala Ser Asp
1

<210> SEQ ID NO 150
<211> LENGTH: 12
```

```
<212> TYPE: PRT
<213> ORGANISM: Adenovirus serotype 50

<400> SEQUENCE: 150

Asn Gly Asp Glu Thr Thr Thr Trp Lys Asp Leu Glu
1               5                   10
```